US011311496B2

(12) United States Patent
Edelson

(10) Patent No.: US 11,311,496 B2
(45) Date of Patent: Apr. 26, 2022

(54) TRANSDERMAL DELIVERY OF LARGE AGENTS

(71) Applicant: Eirion Therapeutics, Inc., Woburn, MA (US)

(72) Inventor: Jonathan Edelson, Nashua, NH (US)

(73) Assignee: Eirion Therapeutics, Inc., Woburn, MA (US)

( * ) Notice: Subject to any disclaimer, the term of this patent is extended or adjusted under 35 U.S.C. 154(b) by 0 days.

(21) Appl. No.: 16/462,485

(22) PCT Filed: Sep. 25, 2017

(86) PCT No.: PCT/US2017/053333
§ 371 (c)(1),
(2) Date: May 20, 2019

(87) PCT Pub. No.: WO2018/093465
PCT Pub. Date: May 24, 2018

(65) Prior Publication Data
US 2019/0343773 A1 Nov. 14, 2019

Related U.S. Application Data

(60) Provisional application No. 62/424,937, filed on Nov. 21, 2016.

(51) Int. Cl.
| | |
|---|---|
| *A61K 9/70* | (2006.01) |
| *A61K 9/00* | (2006.01) |
| *A61K 9/107* | (2006.01) |
| *A61K 8/64* | (2006.01) |
| *A61Q 15/00* | (2006.01) |
| *A61Q 19/08* | (2006.01) |

(52) U.S. Cl.
CPC .......... *A61K 9/7038* (2013.01); *A61K 9/0014* (2013.01); *A61K 9/0021* (2013.01); *A61K 9/1075* (2013.01); *A61K 8/64* (2013.01); *A61K 2800/91* (2013.01); *A61Q 15/00* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 3,725,540 A | 4/1973 | Wahl | |
| 3,964,482 A * | 6/1976 | Gerstel | A61K 9/0021 |
| | | | 604/890.1 |
| 4,075,096 A | 2/1978 | Kawakami et al. | |
| 4,075,196 A | 2/1978 | Badertscher et al. | |
| 4,152,170 A | 5/1979 | Nagase et al. | |
| 4,172,149 A | 10/1979 | Pinto et al. | |
| 4,373,526 A | 2/1983 | Kling | |
| 4,526,938 A | 7/1985 | Churchill et al. | |
| 4,533,254 A | 8/1985 | Cook et al. | |
| 4,618,664 A | 10/1986 | Ohnishi | |
| 4,908,154 A | 3/1990 | Cook et al. | |
| 5,008,110 A | 4/1991 | Benecke et al. | |
| 5,152,923 A | 10/1992 | Weder et al. | |
| 5,302,401 A | 4/1994 | Liversidge et al. | |
| 5,374,614 A | 12/1994 | Behan et al. | |
| 5,401,243 A | 3/1995 | Borodic | |
| 5,470,577 A | 11/1995 | Gilchrest et al. | |
| 5,502,045 A | 3/1996 | Miettinen et al. | |
| 5,510,118 A | 4/1996 | Bosch et al. | |
| 5,554,372 A | 9/1996 | Hunter | |
| 5,576,016 A | 11/1996 | Amselem et al. | |
| 5,591,767 A | 1/1997 | Mohr et al. | |
| 5,613,952 A | 3/1997 | Pressly, Sr. et al. | |
| 5,629,021 A | 5/1997 | Wright | |
| 5,651,991 A | 7/1997 | Sugiyama et al. | |
| 5,652,274 A | 7/1997 | Martin | |
| 5,660,858 A | 8/1997 | Parikh et al. | |
| 5,670,484 A | 9/1997 | Binder | |
| 5,672,358 A | 9/1997 | Tabibi et al. | |
| 5,683,712 A | 11/1997 | Cavazza | |
| 5,753,241 A | 5/1998 | Ribier et al. | |
| 5,766,605 A | 6/1998 | Sanders et al. | |
| 5,851,452 A | 12/1998 | Vallet Mas et al. | |
| 5,858,410 A | 1/1999 | Muller et al. | |
| 5,925,341 A | 7/1999 | Cervantes et al. | |
| 5,932,562 A | 8/1999 | Ostlund, Jr. | |
| 5,948,433 A | 9/1999 | Burton et al. | |
| 5,965,154 A | 10/1999 | Haralambopoulos | |
| 5,993,852 A | 11/1999 | Foldvari et al. | |
| 5,994,414 A | 11/1999 | Franco et al. | |
| 6,007,803 A | 12/1999 | Mandeville, III et al. | |
| 6,007,856 A | 12/1999 | Cox et al. | |
| 6,010,715 A | 1/2000 | Wick et al. | |
| 6,039,936 A | 3/2000 | Restle et al. | |
| 6,087,327 A | 7/2000 | Pearce et al. | |
| 6,117,454 A | 9/2000 | Kreuter et al. | |
| 6,165,500 A | 12/2000 | Cevc | |
| 6,203,802 B1 | 3/2001 | Handjani et al. | |
| 6,224,853 B1 | 5/2001 | Steel et al. | |
| 6,265,180 B1 | 7/2001 | Zuelli et al. | |
| 6,274,150 B1 | 8/2001 | Simonnet et al. | |
| 6,312,708 B1 | 11/2001 | Donovan | |

(Continued)

FOREIGN PATENT DOCUMENTS

| | | |
|---|---|---|
| CA | 02067754 A1 | 2/1992 |
| CA | 2442660 A1 | 10/2002 |
| CA | 2465123 A1 | 5/2003 |
| CA | 2543722 A1 | 5/2005 |
| CA | 2554052 A1 | 8/2005 |

(Continued)

OTHER PUBLICATIONS

Davis et al., J. Biomech. 37 (2004) 1155-1163 (Year: 2004).*
•Martanto et al., Pharm. Res. 21/6 (2004) 947-952 (Year: 2004).*
McAllister et al., PNAS 100/24 (2003) 13755-13760 (Year: 2003).*
Park, J. Controlled Release 104/1 (2005) 51-66 Available online: Apr. 1, 2005 (Year: 2005).*

(Continued)

*Primary Examiner* — Nita M. Minnifield
(74) *Attorney, Agent, or Firm* — Choate, Hall & Stewart LLP; Brenda Herschbach Jarrell; Sowmya Subramanian

(57) ABSTRACT

Methods, compositions, and devices for enhancing transdermal delivery of large agents.

50 Claims, 2 Drawing Sheets

Specification includes a Sequence Listing.

(56) References Cited

U.S. PATENT DOCUMENTS

| | | | |
|---|---|---|---|
| 6,334,856 B1 * | 1/2002 | Allen | A61B 5/14514 604/191 |
| 6,358,917 B1 | 3/2002 | Carruthers et al. | |
| 6,387,411 B2 | 5/2002 | Bruce et al. | |
| 6,395,029 B1 | 5/2002 | Levy | |
| 6,429,189 B1 | 8/2002 | Borodic | |
| 6,455,058 B1 | 9/2002 | Sun et al. | |
| 6,458,373 B1 | 10/2002 | Lambert et al. | |
| 6,461,596 B1 | 10/2002 | Taylor | |
| 6,503,231 B1 * | 1/2003 | Prausnitz | A61B 5/14514 604/272 |
| 6,558,941 B2 | 5/2003 | Zuelli et al. | |
| 6,573,241 B1 | 6/2003 | Bigalke et al. | |
| 6,589,588 B1 | 7/2003 | Wester et al. | |
| 6,611,707 B1 * | 8/2003 | Prausnitz | A61B 5/14514 604/21 |
| 6,620,419 B1 | 9/2003 | Lintner | |
| 6,623,780 B1 | 9/2003 | Stevens et al. | |
| 6,632,440 B1 | 10/2003 | Quinn et al. | |
| 6,670,322 B2 | 12/2003 | Goodnough et al. | |
| 6,688,311 B2 | 2/2004 | Hanin | |
| 6,720,001 B2 | 4/2004 | Chen et al. | |
| 6,745,211 B2 * | 6/2004 | Kabasakalian | G06F 16/2365 707/690 |
| 6,765,001 B2 | 7/2004 | Gans et al. | |
| 6,835,395 B1 | 12/2004 | Semple et al. | |
| 6,835,895 B1 | 12/2004 | Asai et al. | |
| 6,861,066 B2 | 3/2005 | Van de Casteele | |
| 6,869,610 B2 | 3/2005 | Aoki et al. | |
| 6,875,438 B2 | 4/2005 | Kraemer et al. | |
| 6,890,560 B2 | 5/2005 | Seo et al. | |
| 6,902,737 B2 | 6/2005 | Quemin | |
| 6,939,852 B2 | 9/2005 | Graham | |
| 6,974,578 B1 | 12/2005 | Aoki et al. | |
| 6,974,579 B2 | 12/2005 | Brin et al. | |
| 7,001,602 B2 | 2/2006 | Schmidt | |
| RE39,086 E | 5/2006 | Carruthers et al. | |
| 7,063,860 B2 | 6/2006 | Chancellor et al. | |
| 7,125,858 B2 | 10/2006 | Filion | |
| 7,226,605 B2 | 6/2007 | Suskind et al. | |
| 7,228,259 B2 | 6/2007 | Freund | |
| 7,255,865 B2 | 8/2007 | Walker | |
| 7,384,918 B2 | 6/2008 | Graham | |
| 7,419,996 B2 | 9/2008 | Chow et al. | |
| 7,507,419 B2 | 3/2009 | Coleman, III | |
| 7,531,193 B2 | 5/2009 | Demarne et al. | |
| 7,727,537 B2 | 6/2010 | Modi | |
| 7,758,871 B2 | 7/2010 | Donovan | |
| 7,763,663 B2 | 7/2010 | McCarthy et al. | |
| 7,838,011 B2 | 11/2010 | Modi | |
| 8,318,181 B2 | 11/2012 | Edelson et al. | |
| 8,623,811 B2 * | 1/2014 | Stone | A61P 11/00 514/1.1 |
| 8,658,391 B2 | 2/2014 | Edelson | |
| 8,710,010 B2 | 4/2014 | Van Den Nest et al. | |
| 8,710,011 B2 | 4/2014 | Garcia Sanz et al. | |
| 9,314,431 B2 | 4/2016 | Modi | |
| 9,340,587 B2 * | 5/2016 | Thompson | C07K 14/33 |
| 9,458,194 B2 | 10/2016 | Ferrer Montiel et al. | |
| 9,486,408 B2 | 11/2016 | Edelson et al. | |
| 9,486,409 B2 | 11/2016 | Edelson et al. | |
| 9,649,266 B2 | 5/2017 | Edelson | |
| 9,724,299 B2 | 8/2017 | Kotyla | |
| 9,725,483 B2 | 8/2017 | Garcia Anton et al. | |
| 9,770,400 B2 | 9/2017 | Courtois et al. | |
| 9,771,392 B2 | 9/2017 | Ferrer Montiel et al. | |
| 9,956,435 B2 * | 5/2018 | Ruegg | A61P 13/06 |
| 10,016,364 B2 * | 7/2018 | Nicolosi | A61P 3/06 |
| 10,016,451 B2 * | 7/2018 | Edelson | A61P 17/00 |
| 10,111,939 B2 * | 10/2018 | Thompson | A61K 8/022 |
| 10,201,594 B2 * | 2/2019 | Ruegg | A61K 47/10 |
| 10,285,941 B2 * | 5/2019 | Kotyla | A61P 17/00 |
| 10,485,855 B2 * | 11/2019 | Edelson | A61B 5/4842 |
| 10,532,019 B2 * | 1/2020 | Edelson | A61K 47/02 |
| 10,576,034 B2 * | 3/2020 | Edelson | A61K 8/062 |
| 10,758,485 B2 * | 9/2020 | Kotyla | A61P 17/16 |
| 10,905,637 B2 * | 2/2021 | Edelson | A61K 38/08 |
| 2002/0015721 A1 | 2/2002 | Simonnet et al. | |
| 2002/0034474 A1 | 3/2002 | Sabel et al. | |
| 2002/0048596 A1 | 4/2002 | Cevc | |
| 2002/0086036 A1 | 7/2002 | Walker | |
| 2002/0098215 A1 | 7/2002 | Douin et al. | |
| 2002/0107199 A1 | 8/2002 | Walker | |
| 2002/0155084 A1 | 10/2002 | Roessler et al. | |
| 2002/0165179 A1 | 11/2002 | Baker | |
| 2002/0187164 A1 | 12/2002 | Borodic | |
| 2002/0193754 A1 * | 12/2002 | Cho | A61B 5/14514 604/272 |
| 2003/0072801 A1 | 4/2003 | Curatolo et al. | |
| 2003/0072841 A1 | 4/2003 | Rajaiah et al. | |
| 2003/0077240 A1 | 4/2003 | LeGrow et al. | |
| 2003/0077283 A1 | 4/2003 | Ye | |
| 2003/0086888 A1 | 5/2003 | LeGrow et al. | |
| 2003/0105000 A1 | 6/2003 | Pero et al. | |
| 2003/0108597 A1 | 6/2003 | Chancellor et al. | |
| 2003/0113349 A1 | 6/2003 | Coleman | |
| 2003/0138465 A9 | 7/2003 | Douin et al. | |
| 2003/0157138 A1 | 8/2003 | Eini et al. | |
| 2003/0194412 A1 | 10/2003 | Baker et al. | |
| 2003/0206955 A1 | 11/2003 | Sonneville-Aubrun et al. | |
| 2003/0211140 A1 | 11/2003 | Mantripragada et al. | |
| 2003/0224020 A1 | 12/2003 | Zabudkin et al. | |
| 2003/0229141 A1 | 12/2003 | Yu et al. | |
| 2004/0003324 A1 | 1/2004 | Uhlig et al. | |
| 2004/0005370 A1 | 1/2004 | Breton | |
| 2004/0009180 A1 | 1/2004 | Donovan | |
| 2004/0009936 A1 | 1/2004 | Tang et al. | |
| 2004/0028635 A1 | 2/2004 | Chauvierre et al. | |
| 2004/0033202 A1 | 2/2004 | Cooper et al. | |
| 2004/0033241 A1 | 2/2004 | Donovan | |
| 2004/0037853 A1 | 2/2004 | Borodic | |
| 2004/0043026 A1 | 3/2004 | Tuan et al. | |
| 2004/0048836 A1 | 3/2004 | Wilmott | |
| 2004/0081688 A1 | 4/2004 | Del Curto et al. | |
| 2004/0106904 A1 * | 6/2004 | Gonnelli | A61B 17/205 604/173 |
| 2004/0115159 A1 | 6/2004 | Tadlock et al. | |
| 2004/0115727 A1 | 6/2004 | Steward et al. | |
| 2004/0116512 A1 | 6/2004 | Naguib et al. | |
| 2004/0126397 A1 | 7/2004 | Aoki et al. | |
| 2004/0127661 A1 | 7/2004 | Kaspar et al. | |
| 2004/0132667 A1 | 7/2004 | Lintner | |
| 2004/0151741 A1 | 8/2004 | Borodic | |
| 2004/0186419 A1 * | 9/2004 | Cho | A61B 5/14514 604/22 |
| 2004/0191330 A1 | 9/2004 | Keefe et al. | |
| 2004/0229038 A1 | 11/2004 | Cooper et al. | |
| 2004/0235770 A1 | 11/2004 | Davis et al. | |
| 2004/0258701 A1 | 12/2004 | Dominowski et al. | |
| 2004/0258747 A1 | 12/2004 | Ponzoni et al. | |
| 2004/0258758 A1 | 12/2004 | Gustow et al. | |
| 2005/0036966 A1 | 2/2005 | Heckmann | |
| 2005/0038096 A1 | 2/2005 | Chow et al. | |
| 2005/0048088 A1 | 3/2005 | Zulli et al. | |
| 2005/0065090 A1 | 3/2005 | Ludin et al. | |
| 2005/0074461 A1 | 4/2005 | Donovan | |
| 2005/0074466 A1 | 4/2005 | Suskind et al. | |
| 2005/0079131 A1 | 4/2005 | Lanza et al. | |
| 2005/0079278 A1 | 4/2005 | Jaiswal et al. | |
| 2005/0096340 A1 | 5/2005 | Zhang et al. | |
| 2005/0118254 A1 | 6/2005 | Choi et al. | |
| 2005/0123897 A1 | 6/2005 | Cevc et al. | |
| 2005/0124378 A1 | 6/2005 | Griffith et al. | |
| 2005/0136024 A1 | 6/2005 | Stockel | |
| 2005/0142175 A1 | 6/2005 | Graham | |
| 2005/0147688 A1 | 7/2005 | Russell | |
| 2005/0152923 A1 | 7/2005 | Brin et al. | |
| 2005/0175636 A1 | 8/2005 | Donovan | |
| 2005/0184275 A1 | 8/2005 | Mora-Gutierrez et al. | |
| 2005/0196414 A1 | 9/2005 | Dake et al. | |
| 2005/0196416 A1 | 9/2005 | Kipp et al. | |
| 2005/0208083 A1 | 9/2005 | Annis | |

(56) References Cited

U.S. PATENT DOCUMENTS

| | | |
|---|---|---|
| 2005/0209565 A1* | 9/2005 | Yuzhakov ............... A61N 1/30 604/173 |
| 2005/0214325 A1 | 9/2005 | David |
| 2005/0214378 A1 | 9/2005 | Hoarau et al. |
| 2005/0226842 A1 | 10/2005 | Douin et al. |
| 2005/0238668 A1 | 10/2005 | Wang et al. |
| 2005/0249686 A1 | 11/2005 | Pataut et al. |
| 2005/0261632 A1 | 11/2005 | Xu |
| 2006/0018931 A1 | 1/2006 | Taylor |
| 2006/0057165 A1 | 3/2006 | Dimitrakoudis et al. |
| 2006/0069055 A1 | 3/2006 | Dajee et al. |
| 2006/0069069 A1 | 3/2006 | Kajander et al. |
| 2006/0073208 A1 | 4/2006 | First |
| 2006/0084353 A1 | 4/2006 | Wong et al. |
| 2006/0093624 A1 | 5/2006 | Graham |
| 2006/0099227 A1 | 5/2006 | Hunt |
| 2006/0153876 A1 | 7/2006 | Sanders |
| 2006/0153877 A1 | 7/2006 | Kozaki et al. |
| 2006/0165657 A1 | 7/2006 | Bernasconi et al. |
| 2006/0182767 A1 | 8/2006 | Borodic |
| 2006/0182794 A1 | 8/2006 | Modi |
| 2006/0188525 A1 | 8/2006 | Donovan |
| 2007/0009555 A1 | 1/2007 | Borodic |
| 2007/0026019 A1 | 2/2007 | Hunt |
| 2007/0036831 A1 | 2/2007 | Baker |
| 2007/0104743 A1 | 5/2007 | Lehtola et al. |
| 2007/0116723 A1 | 5/2007 | Coleman |
| 2007/0148194 A1 | 6/2007 | Amiji et al. |
| 2007/0178121 A1 | 8/2007 | First et al. |
| 2007/0203164 A1 | 8/2007 | Chiang et al. |
| 2007/0253911 A1 | 11/2007 | Tamarkin et al. |
| 2007/0259391 A1 | 11/2007 | Edelson |
| 2007/0270732 A1 | 11/2007 | Levin |
| 2007/0287733 A1 | 12/2007 | Snorrason |
| 2007/0292359 A1 | 12/2007 | Friedman et al. |
| 2008/0050352 A1 | 2/2008 | Webb et al. |
| 2008/0081049 A1 | 4/2008 | Sanders |
| 2008/0102089 A1 | 5/2008 | Cappello |
| 2008/0108570 A1 | 5/2008 | Hunt |
| 2008/0138336 A1 | 6/2008 | Damschroder et al. |
| 2008/0206155 A1 | 8/2008 | Tamarkin et al. |
| 2008/0207737 A1 | 8/2008 | Zinger |
| 2008/0220021 A1 | 9/2008 | Modi |
| 2008/0274195 A1 | 11/2008 | Nicolosi et al. |
| 2009/0010884 A1 | 1/2009 | Chang et al. |
| 2009/0041680 A1 | 2/2009 | Tamarkin et al. |
| 2009/0291095 A1 | 11/2009 | Baker, Jr. et al. |
| 2009/0306198 A1 | 12/2009 | Nicolosi et al. |
| 2010/0040883 A1 | 2/2010 | McCarthy et al. |
| 2010/0049672 A1 | 2/2010 | Straube et al. |
| 2010/0062415 A1 | 3/2010 | Schwoebel et al. |
| 2010/0137357 A1 | 6/2010 | Koleng et al. |
| 2010/0150994 A1 | 6/2010 | Kotyla |
| 2010/0172943 A1 | 7/2010 | Edelson et al. |
| 2010/0183726 A1 | 7/2010 | Nicolosi et al. |
| 2010/0233251 A1 | 9/2010 | Von Andrian et al. |
| 2010/0280975 A1 | 11/2010 | Wischik et al. |
| 2011/0020227 A1 | 1/2011 | McCarthy et al. |
| 2011/0206736 A1 | 8/2011 | Waldman et al. |
| 2011/0206739 A1 | 8/2011 | Nicolosi et al. |
| 2011/0212157 A1 | 9/2011 | Edelson et al. |
| 2011/0213219 A1 | 9/2011 | Bilello et al. |
| 2011/0305734 A1 | 12/2011 | Edelson et al. |
| 2011/0305735 A1 | 12/2011 | Cebrian Puche et al. |
| 2012/0064136 A1 | 3/2012 | Baker, Jr. et al. |
| 2012/0107349 A1 | 5/2012 | Baker, Jr. et al. |
| 2012/0164182 A1 | 6/2012 | Edelson et al. |
| 2012/0208858 A1 | 8/2012 | Shanler et al. |
| 2012/0231034 A1 | 9/2012 | Shaari |
| 2012/0321571 A1 | 12/2012 | Edelson et al. |
| 2012/0321579 A1 | 12/2012 | Edelson et al. |
| 2012/0328525 A1 | 12/2012 | Edelson et al. |
| 2012/0328549 A1 | 12/2012 | Edelson et al. |
| 2012/0328701 A1 | 12/2012 | Edelson et al. |
| 2012/0328702 A1 | 12/2012 | Edelson et al. |
| 2013/0045238 A1 | 2/2013 | Chow et al. |
| 2013/0078295 A1 | 3/2013 | Cebrian Puche et al. |
| 2013/0224245 A1 | 8/2013 | Kommareddy et al. |
| 2013/0251770 A1 | 9/2013 | Waugh et al. |
| 2014/0017331 A1 | 1/2014 | McCarthy et al. |
| 2014/0099342 A1 | 4/2014 | Edelson et al. |
| 2014/0199300 A1 | 7/2014 | Besret et al. |
| 2014/0234382 A1 | 8/2014 | Edelson et al. |
| 2014/0294964 A1 | 10/2014 | Nicolosi et al. |
| 2014/0378384 A1 | 12/2014 | Xu et al. |
| 2015/0037402 A1 | 2/2015 | Chancellor et al. |
| 2015/0196490 A1 | 7/2015 | Edelson et al. |
| 2015/0313536 A1 | 11/2015 | Edelson |
| 2015/0313819 A1 | 11/2015 | Edelson |
| 2015/0335574 A1 | 11/2015 | Nicolosi et al. |
| 2016/0213757 A1 | 7/2016 | Edelson et al. |
| 2017/0079895 A1 | 3/2017 | Edelson et al. |
| 2017/0087088 A1 | 3/2017 | Edelson et al. |
| 2017/0157020 A1 | 6/2017 | Waugh et al. |
| 2017/0181952 A1 | 6/2017 | Edelson et al. |
| 2017/0209553 A1 | 7/2017 | Kaspar et al. |
| 2017/0290773 A1 | 10/2017 | Chancellor et al. |
| 2017/0312210 A1 | 11/2017 | Edelson et al. |
| 2017/0361130 A9 | 12/2017 | Modi |
| 2019/0183785 A1 | 6/2019 | Edelson et al. |
| 2019/0298654 A1 | 10/2019 | Kotyla |
| 2019/0343773 A1* | 11/2019 | Edelson ............... A61K 9/0014 |
| 2020/0054722 A1 | 2/2020 | Edelson |
| 2020/0214961 A1* | 7/2020 | Edelson ............... A61Q 19/08 |
| 2021/0308021 A1* | 10/2021 | Edelson ............... A61P 31/12 |

FOREIGN PATENT DOCUMENTS

| | | | |
|---|---|---|---|
| CA | 2585259 | A1 | 5/2006 |
| CA | 2494473 | C | 6/2007 |
| CA | 2631927 | A1 | 4/2008 |
| CA | 2688415 | A1 | 12/2008 |
| CN | 1130868 | A | 9/1996 |
| CN | 1237151 | A | 12/1999 |
| CN | 1316906 | A | 10/2001 |
| CN | 1946431 | A | 4/2007 |
| CN | 101374498 | A | 2/2009 |
| CN | 101588792 | A | 11/2009 |
| CN | 101765423 | A | 6/2010 |
| CN | 101848702 | A | 9/2010 |
| CN | 101917959 | A | 12/2010 |
| DE | 102004016710 | A1 | 10/2005 |
| DE | 102006046076 | A1 | 4/2007 |
| EP | 0315079 | A1 | 5/1989 |
| EP | 0406162 | A2 | 1/1991 |
| EP | 0572080 | B1 | 11/1995 |
| EP | 0696452 | A1 | 2/1996 |
| EP | 1080720 | A1 | 3/2001 |
| EP | 0770422 | B1 | 9/2002 |
| EP | 1334729 | A1 | 8/2003 |
| EP | 1430906 | A2 | 6/2004 |
| EP | 1502601 | A1 | 2/2005 |
| EP | 1586336 | A1 | 10/2005 |
| EP | 1651162 | A2 | 5/2006 |
| EP | 1652515 | A1 | 5/2006 |
| EP | 1249232 | B1 | 10/2006 |
| EP | 1784163 | A1 | 5/2007 |
| EP | 1345597 | B1 | 10/2007 |
| EP | 1917976 | A1 | 5/2008 |
| EP | 1651162 | B1 | 10/2015 |
| EP | 3689331 | A1 | 8/2020 |
| FR | 2849375 | A1 | 7/2004 |
| JP | 1990000203 | | 1/1990 |
| JP | H02-203 | | 1/1990 |
| JP | H04-198122 | A | 7/1992 |
| JP | H04-198123 | A | 7/1992 |
| JP | H04-202122 | A | 7/1992 |
| JP | H04351623 | A | 12/1992 |
| JP | H07-285863 | A | 10/1995 |
| JP | H08-507515 | A | 8/1996 |
| JP | H10-114648 | A | 5/1998 |
| JP | 2001513331 | A | 9/2001 |
| JP | 2002-534448 | A | 10/2002 |
| JP | 2002308728 | A | 10/2002 |

(56) References Cited

FOREIGN PATENT DOCUMENTS

| | | | | |
|---|---|---|---|---|
| JP | 2003-525257 A | 8/2003 | | |
| JP | 2003527411 A | 9/2003 | | |
| JP | 2004519447 A | 7/2004 | | |
| JP | 2004532214 A | 10/2004 | | |
| JP | 2004/538310 A | 12/2004 | | |
| JP | 2005-507888 A | 3/2005 | | |
| JP | 2005-538082 A | 12/2005 | | |
| JP | 2006273821 A | 10/2006 | | |
| JP | 2007-517890 A | 7/2007 | | |
| JP | 2007-519745 A | 7/2007 | | |
| JP | 2007-523689 A | 8/2007 | | |
| JP | 2007/530544 A | 11/2007 | | |
| JP | 2008/511627 A | 4/2008 | | |
| JP | 2008/514353 A | 5/2008 | | |
| JP | 2008-517890 A | 5/2008 | | |
| JP | 2008-531732 A | 8/2008 | | |
| JP | 2008-543833 A | 12/2008 | | |
| JP | 2009-518307 A | 5/2009 | | |
| JP | 2010-513363 A | 4/2010 | | |
| JP | 2010-528981 A | 8/2010 | | |
| JP | 2010-531298 A | 9/2010 | | |
| KR | 2002-0079150 A | 10/2002 | | |
| KR | 10-2004-0062602 A | 7/2004 | | |
| KR | 2009-0106493 A | 10/2009 | | |
| WO | WO-90/11364 A1 | 10/1990 | | |
| WO | WO-93/18752 A1 | 9/1993 | | |
| WO | WO-9400481 A1 * | 1/1994 | ......... | A61K 38/4893 |
| WO | WO-94/20072 A1 | 9/1994 | | |
| WO | WO-95/22973 A1 | 8/1995 | | |
| WO | WO-95/35157 A1 | 12/1995 | | |
| WO | WO-96/23409 A1 | 8/1996 | | |
| WO | WO-96/39167 A1 | 12/1996 | | |
| WO | WO-98/20834 A2 | 5/1998 | | |
| WO | WO-98/51278 A2 | 11/1998 | | |
| WO | WO-99/07238 A2 | 2/1999 | | |
| WO | WO-99/27918 A1 | 6/1999 | | |
| WO | WO-99/44594 A1 | 9/1999 | | |
| WO | WO-00/07621 A2 | 2/2000 | | |
| WO | WO-0015245 A2 | 3/2000 | | |
| WO | WO-00/38653 A1 | 7/2000 | | |
| WO | WO-00/41528 A2 | 7/2000 | | |
| WO | WO-00/74658 A1 | 12/2000 | | |
| WO | WO-01/10413 A2 | 2/2001 | | |
| WO | WO-01/064328 A1 | 9/2001 | | |
| WO | WO-01/70197 A2 | 9/2001 | | |
| WO | WO-01/88019 A1 | 11/2001 | | |
| WO | WO-02/39979 A1 | 5/2002 | | |
| WO | WO-02/051390 A2 | 7/2002 | | |
| WO | WO-02/056866 A1 | 7/2002 | | |
| WO | WO-02/064112 A2 | 8/2002 | | |
| WO | WO-02/076441 A1 | 10/2002 | | |
| WO | WO-02/080864 A1 | 10/2002 | | |
| WO | WO-2003/000243 A1 | 1/2003 | | |
| WO | WO-03/011333 A1 | 2/2003 | | |
| WO | WO-03/037933 A2 | 5/2003 | | |
| WO | WO-03/071267 A1 | 8/2003 | | |
| WO | WO-03/092585 A2 | 11/2003 | | |
| WO | WO-03/101483 A1 | 12/2003 | | |
| WO | WO-2004/006954 A2 | 1/2004 | | |
| WO | WO-2004/076634 A2 | 9/2004 | | |
| WO | WO-2004/084839 A2 | 10/2004 | | |
| WO | WO-2004/103272 A2 | 12/2004 | | |
| WO | WO-2005/007225 A1 | 1/2005 | | |
| WO | WO-2005/013938 A1 | 2/2005 | | |
| WO | WO-2005/020962 A1 | 3/2005 | | |
| WO | WO-2005/023282 A1 | 3/2005 | | |
| WO | WO-2005/027872 A2 | 3/2005 | | |
| WO | WO-2005/042539 A1 | 5/2005 | | |
| WO | WO-2005/058370 A1 | 6/2005 | | |
| WO | WO-2005/063377 A1 | 7/2005 | | |
| WO | WO-2005/070394 A2 | 8/2005 | | |
| WO | WO-2005/074894 A1 | 8/2005 | | |
| WO | WO-2005/082514 A2 | 9/2005 | | |
| WO | WO-2005/084361 A2 | 9/2005 | | |
| WO | WO-2005/084410 A2 | 9/2005 | | |
| WO | WO-2005/091991 A2 | 10/2005 | | |
| WO | WO-2005/102285 A1 | 11/2005 | | |
| WO | WO-2006/005910 A2 | 1/2006 | | |
| WO | WO-2006/025976 A1 | 3/2006 | | |
| WO | WO-2006/028339 A1 | 3/2006 | | |
| WO | WO-2006/039014 A1 | 4/2006 | | |
| WO | WO-2006/045170 A2 | 5/2006 | | |
| WO | WO-2006/050926 A2 | 5/2006 | | |
| WO | WO-2006/084353 A1 | 8/2006 | | |
| WO | WO-2006/094263 A2 | 9/2006 | | |
| WO | WO-2006/123354 A2 | 11/2006 | | |
| WO | WO-2006/138059 A2 | 12/2006 | | |
| WO | WO-2006/138127 A2 | 12/2006 | | |
| WO | WO-2007/046102 A2 | 4/2007 | | |
| WO | WO-2007041664 A1 | 4/2007 | | |
| WO | WO-2007/089454 A2 | 8/2007 | | |
| WO | WO-2007/103555 A2 | 9/2007 | | |
| WO | WO-2007/149868 A2 | 12/2007 | | |
| WO | WO-2008/010788 A2 | 1/2008 | | |
| WO | WO-2008/038147 A2 | 4/2008 | | |
| WO | WO-2008/045107 A2 | 4/2008 | | |
| WO | WO-2008054362 A2 * | 5/2008 | ........... | A61B 17/205 |
| WO | WO-2008/070538 A2 | 6/2008 | | |
| WO | WO-2008/074885 A2 | 6/2008 | | |
| WO | WO-2008/077641 A1 | 7/2008 | | |
| WO | WO-2008/140594 A2 | 11/2008 | | |
| WO | WO-2008/151022 A2 | 12/2008 | | |
| WO | WO-2008/156446 A1 | 12/2008 | | |
| WO | WO-2008/156646 A1 | 12/2008 | | |
| WO | WO-2009/073569 A2 | 6/2009 | | |
| WO | WO-2009/158687 A1 | 12/2009 | | |
| WO | WO-2010/040271 A1 | 4/2010 | | |
| WO | WO-2010/056922 A2 | 5/2010 | | |
| WO | WO-2010/087964 A2 | 8/2010 | | |
| WO | WO-2010/128087 A2 | 11/2010 | | |
| WO | WO-2011/041483 A2 | 4/2011 | | |
| WO | WO-2011/050180 A1 | 4/2011 | | |
| WO | WO-2012/103035 A1 | 8/2012 | | |
| WO | WO-2012/103039 A1 | 8/2012 | | |
| WO | WO-2012103038 A2 | 8/2012 | | |
| WO | WO-2013/013042 A1 | 1/2013 | | |
| WO | WO-2013/097704 A1 | 7/2013 | | |
| WO | WO-2014/186134 A1 | 11/2014 | | |
| WO | WO-2015/020982 A2 | 2/2015 | | |
| WO | WO-2016/065426 A1 | 5/2016 | | |
| WO | WO-2017/075468 A1 | 5/2017 | | |
| WO | WO-2018/093465 A1 | 5/2018 | | |
| WO | WO-2020/056160 A1 | 3/2020 | | |
| WO | WO-2020/056191 A1 | 3/2020 | | |
| WO | WO-2020/117564 A1 | 6/2020 | | |
| WO | WO-2020117564 A1 * | 6/2020 | ........... | A61K 9/0021 |
| WO | WO-2020/231983 A1 | 11/2020 | | |

OTHER PUBLICATIONS

Prausnitz, Advanced Drug Delivery Reviews 56 (2004) 581-587 (Year: 2004).*
Shirkhandeh J. Materials Sci. 16 (2005) 37-45 (Year: 2005).*
•Remington: The Science Practice of Pharmacy 21st ed., Lippincott Williams & Wilkins 2005 (Year: 2005).*
•Zahn et al., Biomed. Microdevices 6 (2004) 183-190 (Year: 2004).*
Kavanagh et al, J. Am. Acad. Dermatol. Nov. 2006. 55/(5):S115-S117 (Year: 2006).*
Lowe et al., j. Am Acad. Dermatol., 2007, 56:604-611. published online:Feb. 20, 2007 (Year: 2007).*
International Search Report for PCT/US2019/050849, 4 pages (dated Dec. 10, 2019).
International Search Report for PCT/US2019/050890, 5 pages (dated Dec. 13, 2019).
International Search Report for PCT/US2019/063351, 5 pages (dated Mar. 5, 2020).
Lee, S-H. et al., Therapeutic efficacy of autologous platelet-rich plasma and polydeoxyribonucleotide on female pattern hair loss, Wound Repair and Regeneration, 23:30-36 (2015).
Mason, T.G. et al., Topical Review; Nanoemulsions: formation, structure, and physical properties, Journal of Physics: Condensed Matter, Institute of Physics Publishing, 18(41): R635-R666 (2006).

(56) References Cited

OTHER PUBLICATIONS

Ranieri, G. et al., Defibrotide in the treatment of Rayaud's phenomenon in patients with progressive systemic sclerosis or essential mixed cryoglobulinemia, Current Therapeutic Research, 53(1):48-58 (1993).
Siwu, F. et al., Effects of Various Agents on the Potency of Botulinum Toxin Type C, Progress in Microbiology and Immunology, 3: Abstract Only, 1 page (1996).
Syed, F. et al., Ex vivo evaluation of antifibrotic compounds in skin scarring: EGCG and silencing of PAI-1 independently inhibit growth and induce keloid shrinkage, Laboratory Investigation, 93(8):946-690 (2013).
Written Opinion for PCT/US2019/063351, 9 pages (dated Mar. 5, 2020).
Written Opinion for PCT/US2019/050849, 7 pages (dated Dec. 10, 2019).
Written Opinion for PCT/US2019/050890, 11 pages (dated Dec. 13, 2019).
Devani, M. et al., The emulsification and solubilisation properties of polyglycolysed oils in self-emulsifying formulations, Journal of Pharmacy and Pharmacology, 56(3):307-316 (2004).
International Search Report for PCT/US2020/032458, 5 pages (dated Aug. 17, 2020).
Labrafills, Supplementary information on excipients, The Royal Society of Chemistry, 5 pages (2018). URL: <http://www.rsc.org/suppdata/c7/nr/c7nr08488a/c7nr08488a1.pdf> [Retrieved on Jun. 4, 2020].
Santos-Magalhaes, N.S. et al., Colloidal carriers for benzathine penicillin G: Nanoemulsions and nanocapsules, Intl. Jrnl. Pharm., 208:71-80 (2000).
Sato, F. and Yukio, M., Botulinum Toxin and the Management of Spasticity, Jpn J Rehabil Med., 37(7):475-482 (2000).
Tadros et al., Formation and stability of nanoemulsions, Advances in Colloid and Interface Science, 108-109:303-318 (2004).
Written Opinion for PCT/US2020/032458, 7 pages (dated Aug. 17, 2020).
Alves, P.M. et al., Semisolid topical formulations containing nimesulide-loaded nanocapsules, nanospheres or nanoemulsion: development and rheological characterization, Pharmazie, 60:900-904 (2005).
Aoki K.R., Botulinum neurotoxin serotype A and B preparations have different safety margins in preclinical models of muscle weakening efficacy and systemic safety, Toxicon 40:923-928 (2002).
Badea, I. et al., In vivo cutaneous interferon-γ gene delivery using novel dicationic (gemini) surfactant-plasmid complexes, The Journal of Gene Medicine, 7:1200-1214 (2005).
Bauerova et al., Chemical enhancers for transdermal drug transport, European J Drug Metabolism and Pharmacokinetics 26(1/2):85-94 (2001).
Bhartiya et al., Enhanced Wound Healing in Animal Models by Interferon and an Interferon Inducer, J Cell Physiol 150:312-319 (1992).
Bos and Meinardi, The 500 Dalton rule for the skin penetration of chemical compounds and drugs, Exp Dermatol 9:165-169 (2000).
Brewster, Delivering Anti-aging Actives, Cosmetics and Toiletries, 120(6):30, 32-34 (2005).
Cappel et al., Effect of Nanoparticles on Transdermal Drug Delivery, J. Microencapsulation, (3):369-374, 1991.
Carruthers et al., Botulinum A exotoxin use in clinical dermatology, J. Am. Acad. Dermatol. 34(5):788 (1996).
CAS Registry No. 144-68-3, Zeaxanthin, 5 pages (Nov. 16, 1984).
Chajchir, I. et al., Novel topical BoNTA (CosmeTox, Toxin Type A) cream used to treat hyperfunctional wrinkles of the face, mouth, and neck, Aesthetic Plastic Surgery, 32:715-722 (2008).
Chen et al., Transdermal protein delivery by a coadministered peptide identified via phage display, Nature Biotechnology 24(4):455-459 (2006).
Chien, Y.W., Novel drug delivery systems, Second Edition, Marcel Dekker, Inc., New York, Chapter 7, pp. 301-380 (1992).

Choi et al, Percutaneous Absorption, Fourth Edition Bronaugh and Maibach ed., Taylor and Francis, Boca Ratonm Florida, Index and Table of contents only 155:33 (2005).
Cocconi et al., Treatment of Metastatic Malignant Melanoma with Dacarbazine Plux Tamoxifen, New England J Medicine 327(8):516-23 (1992).
Collins, A. and Nasir, A., Topical Botulinum Toxin, Journal of Clinical Aesthetic Dermatology, 3(3):35-39 (2010).
CRODA Inc., Pharmaceutical Technology, 3 pages (2005), Retrieved online: http://www.pharmtech.com/pharmtech/Corporate=Capabilities/Croda-Inc/ArticleStandard/Article/detail/399061.
Dalgleish et al., The characterization of small emulsion droplets made from milk proteins and triglyceride oil, Colloids and Surfaces, 123-124:145-153 (May 15, 1997).
De Campo et al., Five-component food-grade microemulsions: Structural characterization by SANS, J Colloid and Interface Science, 274:251-267 (2004).
De Paiva and Dolly, Light chain of botulinum nerotoxin is active in mammalian motor nerve terminals when delivered via liposomes, FEBS 277(1,2):171-174 (1990).
Delgado-Charro et al., Delivery of a hydrophilic solute through the skin from novel microemulsion systems, Eur J Pharmaceutics and Biopharmaceutics 43[1]:37-42 (1997).
Devani, M. et al., The development and characterization of triglyceride-based 'spontaneous' multiple emulsions, International Journal of Pharmaceutics, 300:76-88 (2005).
Dittgen et al., Acrylic Polymers, A Review of Pharmaceutical Applications, S. T.P. Pharma Sciences, 7(6):403-437, 1997.
Forster et al., Micellization of Strongly Segregated Block Copolymers, J. Chem. Physics, 104(24):9956-9970, 1996.
Fujinaga, Interaction of Botulinum Toxin With the Epitheliol Barrier, J. Biomedicine and Biotechnology, 2010: Article 974943 (2010).
Galioglu et al., Block/graft copolymer synthesis via eerie salt, Die Angewandte makromolekulare chemie, 19-28 (1994).
Gunniss, I., Microfluidics Webinar Series." "Principles of Particle Size Reduction and Characterization, 42 pages (Retrieved by Examiner Mar. 24, 2017). URL: http://www.horiba.com/fileadmin/uploads/Scientific/Documents/PSA/Webinar_Slides/TE007.pdf.
Guo, L. et al., Enhanced transcutaneous immunization via dissolving microneedle array loaded with liposome encapsulated antigen and adjuvant, International Journal of Pharmaceutics, 447: 22-30 (2013).
Hamouda, T. et al., A novel surfactant nanoemulsion with broad-spectrum sporicidal activity against *bacillus* species, The Journal of Infectious Diseases, 180:1939-1949 (1999).
Hancock et al., An Antioxidant Formulation that Induces Differentiation of Neuroblastoma in Culture, Neuroscience Research Communications, 33(1): 73-76 (2003).
Hardas, B. and Brin, M.F., Topical botulinum toxin type A, Procedures in Cosmetic Dermatology, Botulinum Toxin, Fourth Edition, Edited by J. Carruthers et al., Chapt 12: 81-84 (2018).
Helene et al., Control of Gene Expression by Triple Helix-Forming Oligonucleotides, Ann N.Y. Acad Sci 660:27-36 (1992).
Helene, The anti-gene strategy: control of gene expression by triplex-forming-oligonucleotides, Anti-Cancer Drug Des 6:569-584 (1991).
Heurtault et al., A Novel Phase Inversion-Based Process for the Preparation of Lipid Nanocarriers, Pharmaceutical Research 19(6):875-880 (2002).
Hickerson et al., SiRNA-Mediated Selective Inhibition of Mutant Keratin mRNAs Responsible for the Skin Disorder Pachyonychia Congenita, Ann. N.Y. Acad. Sci. 1082:56-61 (2006).
Hiraishi Y, Hirobe S, Iioka H, Quan YS, Kamiyama F, Asada H, et al. Development of a novel therapeutic approach using a retinoic acid loaded microneedle patch for seborrheic keratosis treatment and safety study in humans. J Control Release 2013;171:93-103.
International Search Report for PCT/US2006/026918, 4 pages (dated Jun. 19, 2008).
International Search Report for PCT/US2006/035343, 1 page (dated Aug. 15, 2007).
International Search Report for PCT/US2006/046236, 3 pages (dated Jun. 17, 2008).

(56) References Cited

OTHER PUBLICATIONS

International Search Report for PCT/US2007/010253, 2 pages (dated Mar. 14, 2008).
International Search Report for PCT/US2007/086018, 5 pages (dated Sep. 17, 2008).
International Search Report for PCT/US2007/086040, 7 pages (dated Feb. 9, 2010).
International Search Report for PCT/US2008/065329, 5 pages (dated Mar. 12, 2009).
International Search Report for PCT/US2009/048972, 5 pages (dated Dec. 1, 2009).
International Search Report for PCT/US2012/022276, 6 pages (dated Jul. 19, 2012).
International Search Report for PCT/US2012/022277, 4 pages (dated Jul. 6, 2012).
International Search Report for PCT/US2012/022278, 4 pages (dated Mar. 23, 2012).
International Search Report for PCT/US2012/022279, 7 pages (dated Nov. 29, 2012).
International Search Report for PCT/US2012/022280, 4 pages (dated Apr. 27, 2012).
International Search Report for PCT/US2012/022281, 4 pages (dated Apr. 24, 2012).
International Search Report for PCT/US2015/028806, 2 pages (dated Jun. 17, 2015).
International Search Report for PCT/US2017/053333, 5 pages (dated Jan. 25, 2018).
Izquierdo et al., The influence of surfactant mixing ration on nano-emulsion formation by the pit method, J Colloid and Interface Sci. 285:388-394 (2004).
Johnson et al., Clostridium botulinum neurotoxins—Applications in Medicine and Potential Agents of Bioterrorism, Clinical Microbiology Newsletter, 27(19):147-151 (2005).
Kakumanu et al., A Nanoemulsion Formulation of Dacarbazine Reduces Tumor Size in a Xenograft Mouse Epidermoid Carcinoma Model Compared to Dacarbazine Suspension, Nanomedicine: NBM 7(3):277-283 (2011).
Kalb et al., Different Substrate Recognition Requirements for cleavage of Synaptobrevin-2 by Clostridium baratii and Clostridium botulinum, Applied and Environmental Microbiology p. 1301-1308, 2011.
Katayama et al., A Pentapeptide from Type I Procollagen Promotes Extracellular Matrix Production, J Biol Chem 268(14):9941-9944 (1993).
Keen et al., Botulinum Toxin A for Hyperkinetic Facial Lines: Results of a Double-Blind, Placebo-Controlled Study, Plastic and Reconstructive Surgery, 94(1):94-9 (1994).
Khare et al., In: Microencapsulation in the Food Industry, editors Gaonkar et al., 151-155 (2014).
Kim YC, Song JM, Lipatov AS, Choi SO, Lee JW, Donis RO, et al. Increased immunogenicity of avian influenza DNA vaccine delivered to the skin using a microneedle patch. Eur J Pharm Biopharm 2012;81:239-47.
Kitson, Drugs Used for Skin Diseases, Published in Dermatologic, Cosmeceutic, and Cosmetic Development Therapeutic and Novel Approaches, Ed Walters and Roberts 11-20 (2008).
Kotyla et al., Increased bioavailability of a transdermal application of a nano-sized emulsion preparation, International Journal of Pharmaceutics 347:144-148 (2008).
Kronberg et al., Preparation and Evaluation of Sterically Stabilized Liposomes: Colloidal Stability, Serum Stability, Macrophage Uptake, and Toxicity, J Pharmaceutical Sciences 79(8):667-671 (1990).
Kuo et al., Nanomulsions of an Anti-Oxidant Synergy Formulation Containing Gamma Tocopherol Have Enhanced Bioavailability and Anti-Inflammatory Properties, Int'l J Pharmaceutics 363:206-213 (2008).
Kwon et al., Enhanced Tumor Accumulation and Prolonged Circulation Time of Micelle forming poly , J. Controlled Release, 29: 17-23, 1994.

Langbein, K. et al., Antiwrinkle and antiperspirant effects of botulinum toxin, Biological fear-wars of Century 21, Zhejiang Literary Press, (Jul. 31, 2005). English Translation.
Lee et al., Biomedical Applications of Collagen, Int'l J. of Pharmaceuticals, 221:1-22, 2001.
Leyden et al., Journal of the American Academy of Dermatology, 49(3): 5200-5210 (2003).
Lin et al., Delivery of plasmid DNA expression vector for keratinocyte growth factor-1 using electroporation to improve cutaneous wound healing in a septic rat model, Wound Repair and Regeneration 14:618-624 (2006).
Ling MH, Chen MC. Dissolving polymer microneedle patches for rapid and efficient transdermal delivery of insulin to diabetic rats. Acta Biomater 2013;9:8952-61.
Liu, W. et al., Preparation of cream and emulsion type cosmetics, Skin Science and Cosmetics Efficacy Evaluation, Chemical Industry Press, p. 46 (Nov. 2004). English Translation, 2 pages.
Ludewig and Hoffmann, Adoptive Immunotherapy Methods and Protocols, Humana Press Inc., NJ 393 (2005).
Lupo, Cosmeceutical Peptides, Dermatologic Surgery 31:832-836 (2005).
Ma et al., Two-Dimensional, Shell-Cross-linked Nanoparticle Arrays, J. Am. Chem. Soc., 123:4627-4628,2001.
Maher, DNA Triple-Helix Formation: An Approach to Artificial Gene Repressors?, BioEssays 14:807-815 (1992).
Montecucco et al., Effect of pH on the interaction of botulinum neurotoxins A, B and E with liposomes, Biochem J 259:47-53 (1989).
Morel et al., Incorporation in lipospheres of {D-Trp-6}LHRH, Int'l J Pharmaceutics 105(2):R01-R03 (1994).
Munster, U. et al., RU 58841-myristate—prodrug development for topical treatment of acne and androgenetic alopecia, Pharmazie, 60:8-12 (2005).
Müller, R.H. et al., Solid lipid nanoparticles (SLN) for controlled drug delivery—a review of the state of the art. European Journal of Pharmaceutics and Biopharmaceutics, 50(1):161-77 (2000).
Nakayama, H. et al., Composition and function of base for external agent, Recent Skin External Agent, 1:149-155, 3: 160-166 (First Edition Publication Jul. 10, 1991). English Translation.
Pearce et al., Pharmacologic Characterization of Botulinum Toxin for Basic Science and Medicine, Toxicon 35(9):1373-1412 (1997).
Pickett, A. and Perrow, K., Formulation composition of botulinum toxins in clinical use, Journal of Drugs in Dermatology, 9(9):1085-1091 (2010).
Pinnamaneni, S. et al., Comparison of oil-in-water emulsions manufactured by microfluidization and homogenization, Pharmazie, 58(8): 554-558 (2003).
Poste et al., Lipid Vesicles as Carriers for Introducing Biologically Active Materials into Cells, Methods in cell biology 14:34-35 (1976).
Preti, et al., Genetic influences on human body odor: from genes to the axillae, J. Invest, Dermatol., 130: 344-345 (2010).
Qin, G. et al., Simultaneous basal-bolus delivery of fast-acting insulin and its significance in diabetes management, Nanomedicine: Nanotechnology, Biology, and Medicine, 8: 221-227 (2012).
Robinson, et al., Topical palmitoyl pentapeptide provides improvement in photoaged human facial skin, Int'l J Cosmetic Science 24:155-160 (2005).
Ruland et al., Influence of Various Penetration Enhancers on the In Vitro Permeation of Amino Acids Across Hairless Mouse Skin, Int'l J of Pharmaceutics, 85:7-17, 1992.
Santiago et al., Topical Application of a Peptide Inhibitor of Transforming Growth Factor-β1 Ameliorates Bleomycin-Induced Skin Fibrosis, J Investigative Dermatorlogy 125:450-455 (2005).
Sarver et al., Ribozymes as Potential Anti-HIV-1 Therapeutic Agents, Science 247:1222-1225 (1990).
Saulnier et al., Liquid Crystals and Emulsions in the Formulation of Drug Carriers, Comptes Rendus Chimie, 11(3): 221-228 (2008).
Schantz et al., Properties and use of botulinum toxin and other microbial neurotoxins in medicine, Microbiol. Mol. Biol. Rev., 80-99 (1992).

(56) References Cited

OTHER PUBLICATIONS

Schmalfuss, U. et al., Modification of drug penetration into human skin using microemulsions, J Controlled Release 46(3):279-285 (1997).
Shea et al., Efficacy of Vitamin E, Phosphatidyl Choline, and Pyruvate on Buffering Neuronal Degeneration and Oxidative Stress in Cultured Cortical Neurons and in Central Nervous Tissue of Apolipoprotein E-Deficient Mice, Free Radical Biology & Medicine 33:(2):276-282 (2002).
Shone et al., A 50-kDa fragment from the $NH_2$-terminus of the heavy subunit of Clostridium botulinum type A neurotoxin forms channels in lipid vesicles, Eur J Biochem 167:175-180 (1987).
Sonoda et al., Effects of Emulsifiers on Crystallization Behavior of Lipid Crystals in Nanometer-Size Oil-in-Water Emulsion Droplets, Crystal Growth & Design, 6(1): 306-312 (2006).
Stolnik et al., Long circulating microparticulate drug carriers, Advanced Drug Delivery Reviews, 16:195-214, 1995.
Tadros et al.. Formulation and stability of nanoemulsions, Advances in Colloid and Interface Science, 108-109:303-318 (2004).
Tagne et al., Nanoemulsion Preparations of the Anticancer Drug Dacarbazine Significantly Increase Its Efficacy in Xenograft Mouse Melanoma Model, Molecular Pharmaceutics 5(6):1055-1063 (2008).
Takano, M., Ointment, Today's Skin External Agent, 6: 163-184 (First Edition Publication May 15, 1981, Second Edition Publication Apr. 20, 1982). English Translation.
Talingting et al., "Onion-Type Micelles from polystyrene-block-poly (2-vinylpyridine) and Poly (2-vinylpyridine)-block-poly(ethylene oxide)", Macromolecules, 32:1593-1601, 1999.
Tang, H. et al., Theoretical Description of Transdermal Transport of Hydrophilic Permeants: Application to Low-Frequency Sonophoresis, Journal of Pharmaceutical Sciences, 90(5): 545-568 (2001).
The Harley Medical Group, Excessive Sweating—Causes and Treatment, <http://www.harleymedical.co.uk/non-surgical-solutions/causes/excessive-sweating/> 1 page [last accessed Aug. 26, 2013].
Trotta et al., Elastic Liposomes for Skin Delivery of Dipotassium Glycyrrhizinate, Int'l J Pharmaceutics 241:319-327 (2002).
Verbaan FJ, Bal SM, van den Berg DJ, Groenink WH, Verpoorten H, Lüttge R, et al. Assembled microneedle arrays enhance the transport of compounds varying over a large range of molecular weight across human dermatomed skin. J Control Release 2007;117:238-45.
Verma et al., Particle size of liposomes influences dermal delivery of substances into skin, Int'l J Pharmaceutics 141-151 (2003).
Wang et al., Enhancing effect of Labrafac Lipophile WL 1349 on oral bioavailability of hydroxysafflor yellow A in rats, International Journal of Pharmaceutics 358:198-204 (2008).
Written Opinion for PCT/US2006/026918, 8 pages (dated Jun. 19, 2008).
Written Opinion for PCT/US2006/035343, 4 pages (dated Aug. 15, 2007).
Written Opinion for PCT/US2006/046236, 12 pages (dated Jun. 17, 2008).
Written Opinion for PCT/US2007/010253, 4 pages (dated Mar. 14, 2008).
Written Opinion for PCT/US2007/086018, 6 pages (dated Sep. 17, 2008).
Written Opinion for PCT/US2007/086040, 12 pages (dated Feb. 9, 2010).
Written Opinion for PCT/US2008/065329, 7 pages (dated Mar. 12, 2009).
Written Opinion for PCT/US2009/048972, 5 pages (dated Dec. 1, 2009).
Written Opinion for PCT/US2012/022276, 9 pages (dated Jul. 19, 2012).
Written Opinion for PCT/US2012/022277, 6 pages (dated Jul. 6, 2012).
Written Opinion for PCT/US2012/022279, 7 pages (dated Nov. 29, 2012).
Written Opinion for PCT/US2012/022280, 7 pages (dated Apr. 27, 2012).
Written Opinion for PCT/US2012/022281, 6 pages (dated Apr. 24, 2012).
Written Opinion for PCT/US20120/22278, 7 pages (dated Mar. 23, 2012).
Written Opinion for PCT/US2015/028806, 7 pages (dated Jun. 17, 2015).
Written Opinion for PCT/US2017/053333, 5 pages (dated Jan. 25, 2018).
Wu et al., Topical Transfection Using Plasmid DNA in a Water-in-Oil Nanoemulsion, Int J Pharmaceutics 221(1/02):23-34 (2001).
Wu et al., Topical Transport of Hydrophilic Compounds Using Water-in-Oil Nanoemulsions, Int. J. Pharmaceutics, 220:63-75 (2001).
Wu XM, Todo H, Sugibayashi K. Effects of pretreatment of needle puncture and sandpaper abrasion on the in vitro skin permeation of fluorescein isothiocyanate (FITC)-dextran. Int J Pharm 2006;316:102-8.
Yan, S. et al., Microemulsion cosmetics, Cosmetics Science Book II, Science and Technology Literature Press, p. 321 (Oct. 1998). English Translation, 3 pages.
Zhang and Liu, Study on the Formation and Properties of Liquid Crystal Emulsion in Cosmetic, Journal of Cosmetics, Dermatological Sciences and Applications, 3: 139-144 (2013).
Bansal, C. et al., Novel cutaneous uses for botulinum toxin type A, Journal of Cosmetic Dermatology, 5:268-272 (2006).
Freitas, C. and Muller, R. H., Spray-drying of solid lipid nanoparticles (SLN TM), Eur. J. Pharm. Biopharm., 46(2):145-151 (1998).
Garcion et al., A new generation of anticancer, drug-loaded, colloidal vectors reverses multidrug resistance in glioma and reduces tumor progression in rats, Mol. Cancer Ther., 5(7):1710-1722 (2006).
Jiten, I., Pharmaceutical Excipient Encyclopedia, Edited by Japan Pharmaceutical Excipients Council, Yakuji Nippo (Ed.): 123 (1994). English Translation.
Salopek, B. et al., Measurement and Application of Zeta-Potential, Rudarsko-geolosko-naflni zbomik, 4:147-151 (1992).
Schneider, M. et al., Nanoparticles and their interactions with the dermal barrier, Dermatoendocrinol., 4:197-206 (2009).
Yu, S. et al., Biological warfare prevention medicine, p. 339 (Sep. 1986).
Heymann, W.R. et al.. Hyperhidrosis and botulinum toxin: expanding horizons, J. Am. Acad. Dermotal., 59(2):332-333 (2008).
Siwu, F. et al., Stability study of Clostridium botulinum toxin type C, Progress in Microbiology and Immunology, 3(24):6-9 (1996).

* cited by examiner

The Survival Rates of Control rats who had no skin preconditioning with microneedles and MN rats who had skin preconditioning with microneedles ("MN")

SEQUENCE LISTING

```
<160> NUMBER OF SEQ ID NOS: 1

<210> SEQ ID NO 1
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Arg Lys Lys Arg Arg Gln Arg Arg Arg Gly Lys Lys Lys Lys Lys Lys
1               5                   10                  15

Lys Lys Lys Lys Lys Lys Lys Lys Lys Gly Arg Lys Lys Arg Arg Gln
            20                  25                  30

Arg Arg Arg
        35
```

TRANSDERMAL DELIVERY OF LARGE AGENTS

CROSS-REFERENCE TO RELATED APPLICATIONS

This application claims priority to United States Provisional Application No. 62/424,937, filed Nov. 21, 2016, the entirety of which is incorporated herein by reference.

SEQUENCE LISTING

The present specification makes reference to a Sequence Listing (submitted electronically as a .txt file named "2012317-0207_ST25.txt" on Nov. 18, 2020). The .txt file was generated on Nov. 16, 2017, and is 759 bytes in size. The entire contents of the Sequence Listing are herein incorporated by reference.

BACKGROUND

Significant resources are invested in development of effective transdermal delivery technologies. Those skilled in the art are well aware of challenges associated with achieving effective transdermal delivery, particularly for large agents. As molecular size increases, transdermal penetration decreases, to the point where it is de minimis and even non-existent. Even in those cases where there is some penetration, the large agents tend to become degraded and biologically inactive. There remains a need for novel, effective technologies for effective transdermal administration of such agents, in particular, botulinum toxin and antibody agents, which are large agents, and, as well, are sensitive to degradation.

SUMMARY

Transdermal administration generally has been the subject of research in an attempt to provide an alternative route of administration of agents without undesirable consequences associated with injections and oral delivery. For example, needles often cause localized pain, bleeding and bruising, and potentially expose patients to transmissible diseases; oral administration can suffer from poor bioavailability of medications due to the extremely acidic environment of the patient's stomach. In some embodiments, transdermal delivery has a more even, regular, and/or consistent pharmacokinetic profile as compared with other routes of administration.

While having many advantages, transdermal drug delivery poses a number of logistical problems. Only a limited number of drugs have been shown to be administerable by this route. It has been difficult to transdermally deliver active agents including, but not limited to, hydrophilic molecules, large molecular structures (e.g., greater than a few hundred Daltons), genetic treatments, vaccines, etc. Prausnitz, M. R. & Langer, R. "Transdermal drug delivery," Nat Biotechnol. 26(11): 1261-1268 (2008).

The present disclosure provides improved technologies for transdermal delivery of agents of interest. Among other things, the present disclosure provides an insight that certain advantages may be achieved when microneedling technologies are combined with emulsion technologies for transdermal delivery of agents of interest. Alternatively or additionally, in some embodiments, the present disclosure demonstrates that surprising enhancements can be achieved for transdermal delivery of large molecular structures when microneedling technologies are utilized.

A variety of microneedling technologies have been developed that can be useful for administration of certain agents of interest. Microneedling can avoid certain disadvantages (e.g., amount of pain and/or bleeding) that often associated with use of larger needles (e.g., with standard injection technologies). Microneedling technologies may utilize one or more (e.g., an array of) hollow or solid microneedles. An agent of interest may be disposed in (e.g., if the microneedle is hollow and/or if the agent is incorporated into the microneedle material) or on (i.e., on a surface of) microneedle(s), and/or may be applied to a skin site prior to, during, or after microneedling of the site. An agent that is in or on a microneedle may be released, for example, by diffusion or ejection from the microneedle, or by breakage and/or disintegration of the microneedle material after application to a site.

In some embodiments, the present disclosure provides strategies in which microneedling is used to "condition" skin (and specifically to pre-condition skin prior to administration of the large agent) to which a transdermal product has been, is being, or will be applied. The present disclosure provides an insight that such microneedle conditioning, surprisingly, can provide significant benefit in enhancing transdermal delivery of large agents (e.g., having molecular weights above about 100 KDa or more), notwithstanding prior reports that such strategies are only likely to be useful for small molecular weight agents because studies analyzing transdermal delivery of small molecules (specifically, short, hydrophilic peptides having molecular weights in the range of 400-1000 Da) found "[t]he skin permeation of peptides depends on their molecular weight and decreases as the molecular weight increases." Zhang, S., et al., "Enhanced delivery of hydrophilic peptides in vitro by transdermal microneedle pretreatment." Acta Pharmaceutica Sinica B. 4(1):100-104 (2014).

Thus, prior to the present disclosure, those skilled in the art would have understood from the literature that microneedle conditioning of skin would not be expected to enhance transdermal delivery of large agents. The present disclosure surprisingly demonstrates that microneedle conditioning of skin can significantly enhance transdermal delivery of agents such as botulinum toxin, which has a molecular weight of about 150,000 KDa. Standard antibodies also have a similar molecular weight.

The present disclosure particularly demonstrates that microneedling technologies (e.g., microneedle conditioning of skin) can significantly enhance transdermal delivery of large agents in emulsion compositions (e.g., macroemulsion compositions and/or nanoemulsion compositions). As exemplified, for example, pre-conditioning of skin via application of microneedles prior to any administration of a relevant large agent (botulinum toxin), surprisingly enhanced delivery of the large agent across the skin. Specific examples included herein document such enhanced delivery under various conditions and/or circumstances (e.g., different skin sites, number of applications, etc). Those skilled in the art will be aware of other variations (e.g., to site of application, number of doses, etc) that fall within the scope of the present disclosure.

Particular nanoemulsion compositions of interest include water-in-oil and oil-in-water nanoemulsions characterized by droplet sizes ranging from about 10 nm to about 300 nm in diameter, a ratio of aqueous dispersion media to oil ranging between about 0.01:1 to about 20:1; oil-to-surfactant ratio in a range that spans about 0.1 to about 40 and/or zeta potential in a range that spans about −80 mV to about +80 mV (see e.g., descriptions of nanoemulsion compositions in one or more of PCT/US2006/26918; PCT US06/46236; PCT/US2012/22276; and PCT/US2012/22279, the disclosures of each of which are herein incorporated by reference in their entireties).

Findings presented herein are particularly surprising given reports that transdermal delivery of solid nanoparticles of a size (e.g., 105±2.92 nm) comparable to that of the droplets in the nanoemulsion composition utilized herein do not effectively deliver (or enhance delivery of) even small molecule agents transdermally across skin. For example, Gomaa et al described a study in which a solution of rhodamine dye (molecular weight 479 Da) encapsulated in PLGA nanoparticles was applied to skin that had been preconditioned by microneedling, and skin penetration was assessed. See Gomaa, Y., et al, "Effect of microneedle treatment on the skin permeation of a nanoencapsulated dye." J Pharm Pharmacol. 2012 November; 64(11): 1592-1602. The data showed that very small amounts of dye began to permeate the skin after 6 hours of continuous application; no significant increase in permeation was observed until skin had been treated continuously for 24 hours. The researchers explained that "there is an emerging consensus that NPs [nanoparticles] cannot usually penetrate the stratum corneum, although they may well deposit in hair follicles." Thus, prior to the present disclosure, those skilled in the art would expect that use of microneedling technologies with nano-sized vehicles could not effectively deliver even small molecule agents (e.g., rhodamine dye) transdermally; certainly delivery of large agents would have been considered impossible. The present disclosure, however, demonstrates that microneedling can significantly enhance transdermal delivery of large agents, particularly when utilized in conjunction with a nanoemulsion system.

Among other things, the present disclosure demonstrates that microneedling technologies can enhance transdermal delivery (e.g., of large agents, particularly from macroemulsion or nanoemulsion compositions), when no other disrupting agent (i.e., no chemical penetration enhancing agent and no other technology that disrupts or punctures skin structure) is utilized. Prior studies of transdermal delivery of an agent as large as botulinum toxin (i.e., about 150 kDa) using microneedles have reported that delivery is unsuccessful unless additional treatment is applied to disrupt skin. For example, U.S. Patent Publication No. 2010/0196445 reports that botulinum toxin is not delivered effectively from pre-coated microneedles unless a skin-digesting enzyme is also applied, so that skin structure is disrupted at the site of microneedling.

In some embodiments, the present disclosure provides technologies that achieve enhanced transdermal delivery of large agents (e.g., botulinum toxin, antibodies, etc) by utilizing microneedling technologies without the additional use of a penetration enhancing agent. Alternatively or additionally, in some embodiments, the present disclosure provides technologies that achieve enhanced transdermal delivery of large agents (e.g., botulinum toxin, antibodies, etc.) by utilizing microneedling technologies without any other disrupting strategy. Provided technologies therefore can achieve effective delivery without inflammation, irritation, and/or allergic reaction that often accompanies use of skin disrupting agents.

Alternatively or additionally, the present disclosure identifies the source of a problem with certain prior approaches to associating large agents, and particularly large protein agents (e.g., botulinum toxin, antibodies, etc.), in or on microneedle structures. Typically, such conventional association strategies utilize a liquid solution of the relevant agent, that is applied to a microneedle and allowed to air dry. Such a strategy was utilized to coat microneedles with botulinum toxin in above-noted U.S. Patent Publication No. 2010/0228225. US Patent Publication No. 2017/0209553 describes a microneedle array that is loaded with botulinum into the needles. The present disclosure appreciates that the botulinum coating or loaded material thereby produced is not stable and therefore not commercially viable when used to make a product. Indeed, even if such a liquid is prepared from a powder material, the present disclosure appreciates that, for many large agents (e.g., botulinum toxin), powders and other solid materials that are not formed through a lyophilization process can be highly unstable. For example, per Johnson, E., et al., "Botulinum toxin is very susceptible to denaturation due to surface denaturation, heat, and alkaline conditions. Lyophilization or freeze-drying of botulinum toxin is the most economically sound and practical method of distributing the product in a form that is stable and readily used by the clinician." U.S. Pat. No. 5,512,547. Similarly, such an approach would not work for the administration of therapeutic antibodies which have their own stability and storage challenges. The present disclosure provides the insight that use of an emulsion composition (e.g., in some embodiments, a nanoemulsion composition, and/or in some embodiments a macroemulsion composition) as described herein can protect or otherwise improve stability of large agents, particularly large protein agents, and specifically including botulinum toxin and/or antibody agents, for association with microneedles.

The present disclosure provides surprisingly effective technologies for transdermal delivery of large agents. In particular, the present disclosure teaches that transdermal delivery of such agents can be significantly enhanced through use of certain microneedling technologies. In some embodiments, the present disclosure teaches that particularly advantageous results are achieved when microneedling technologies are combined with emulsion compositions (e.g., in some embodiments, nanoemulsion compositions, and/or in some embodiments macroemulsion compositions). In some embodiments, microneedling technologies are combined with lotion, cream, or liquid compositions, which in turn may be or comprise emulsion compositions (e.g., in some embodiments with nanoemulsion embodiments and/or, in some embodiments with macroemulsion compositions). In some embodiments, provided technologies do not utilize skin disrupting technologies, such as chemical penetration enhancing agents.

DEFINITIONS

Figure 1:
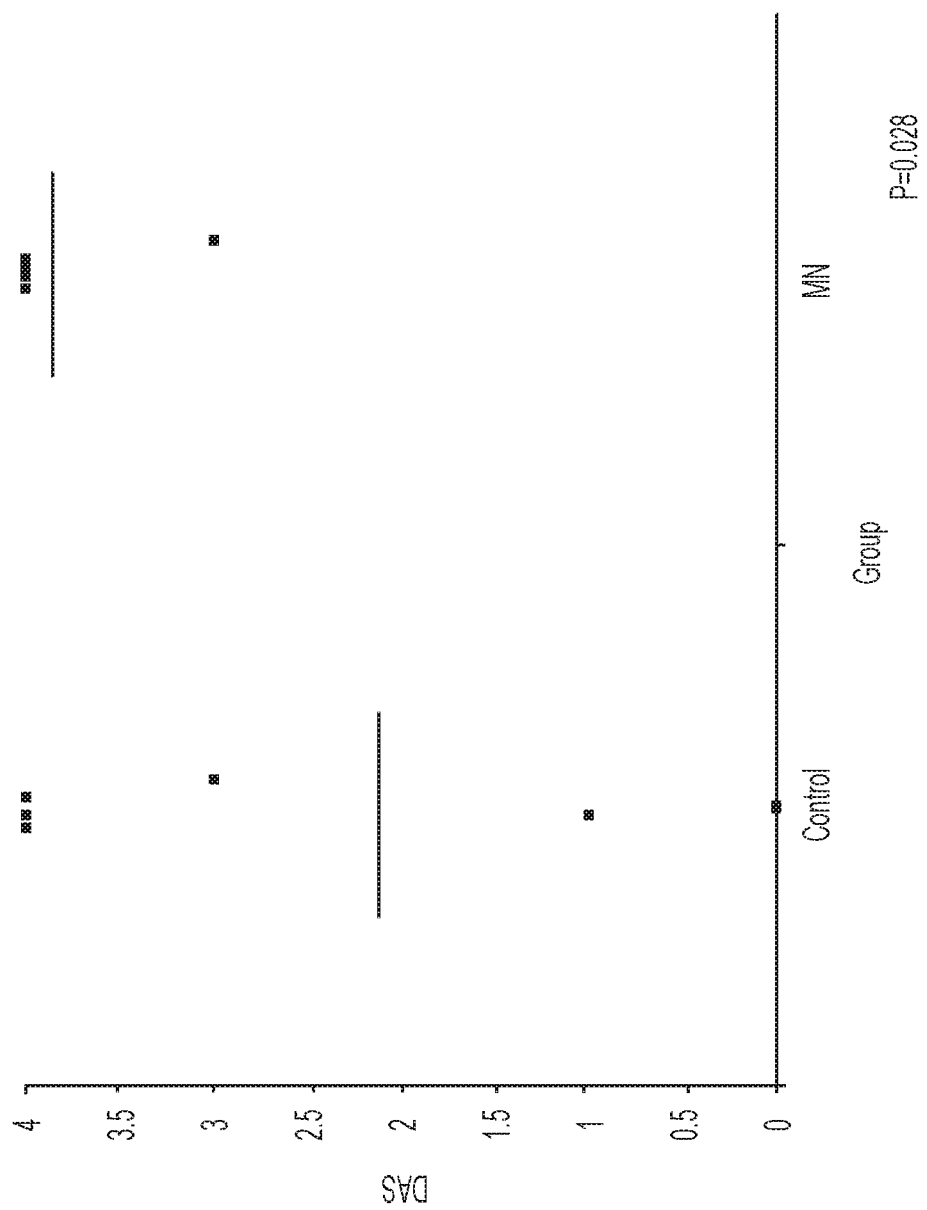
FIG. 1 depicts the digital abduction scoring results of a rat study of the effect of MSC ("microneedle skin conditioning") on the bioavailability of a botulinum nanoemulsion formulation.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Abrasion: The term "abrasion," as used herein refers to any means of altering, disrupting, removing, or destroying the top layer of the skin. In some embodiments, abrasion refers to a mechanical means of altering, disrupting, removing, or destroying the top layer of the skin. In some embodiments, abrasion refers to a chemical means of altering, disrupting, removing, or destroying the top layer of skin. To give but a few examples, agents such as exfoliants, fine particles (e.g. magnesium or aluminum particles), acids (e.g. alpha-hydroxy acids or beta-hydroxy acids), alcohols, may cause abrasion. In general, permeation enhancers such as those described, for example, by Donovan (e.g. US Publications 2004/009180 and 2005/175636, and PCT Publication WO 04/06954), and Graham (e.g. U.S. Pat. No. 6,939,852 and US Publication 2006/093624), etc., are expected to cause abrasion. Of course, those of ordinary skill in the art will appreciate that a particular agent may cause abrasion when present at one concentration, or in association with one or more other agents, but may not cause abrasion under different circumstances. Thus, whether or not a particular material is an "abrasive agent" depends on context. Abrasion can readily be assessed by those of ordinary skill in the art, for example by observation of redness or irritation of the skin and/or histologic examination of skin showing alteration, disruption, removal, or erosion of the stratum corneum.

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety. In some embodiments, the term may refer to a molecular complex.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kDa tetrameric agents comprised of two identical heavy chain polypeptides (about 50 kDa each) and two identical light chain polypeptides (about 25 kDa each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in some embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgG, IgE and IgM, bi- or multi-specific antibodies (e.g., Zybodies®, etc), single chain Fvs, polypeptide-Fc fusions, Fabs, cameloid antibodies, masked antibodies (e.g., Probodies®), Small Modular ImmunoPharmaceuticals ("SMIPs™"), single chain or Tandem diabodies (TandAb®), VHHs, Anticalins®, Nanobodies®, minibodies, BiTE®s, ankyrin repeat proteins or DARPINs®, Avimers®, a DART, a TCR-like antibody, Adnectins®, Affilins®, Trans-Bodies®, Affibodies®, a TrimerX®, MicroProteins, Fynomers®, Centyrins®, and a KALBITOR®. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]

Antibody agent: As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments. As used herein, the term "antibody agent" also includes intact monoclonal antibodies, polyclonal antibodies, single domain antibodies (e.g., shark single domain antibodies (e.g., IgNAR or fragments thereof)), multispecific antibodies (e.g. bi-specific antibodies) formed from at least two intact antibodies, and antibody fragments so long as they exhibit the desired biological activity. In some embodiments, the term encompasses stapled peptides. In some embodiments, the term encompasses one or more antibody-like binding peptidomimetics. In some embodiments, the term encompasses one or more antibody-like binding scaffold proteins. In come embodiments, the term encompasses monobodies or adnectins. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain. In some embodiments, an antibody agent is or comprises an antibody-drug conjugate.

Antibody component: as used herein, refers to a polypeptide element (that may be a complete polypeptide, or a portion of a larger polypeptide, such as for example a fusion polypeptide as described herein) that specifically binds to an epitope or antigen and includes one or more immunoglobulin structural features. In general, an antibody component is any polypeptide whose amino acid sequence includes elements characteristic of an antibody-binding region (e.g., an antibody light chain or variable region or one or more complementarity determining regions ("CDRs") thereof, or an antibody heavy chain or variable region or one more CDRs thereof, optionally in presence of one or more framework regions). In some embodiments, an antibody component is or comprises a full-length antibody. In some embodiments, an antibody component is less than full-length but includes at least one binding site (comprising at least one, and preferably at least two sequences with structure of known antibody "variable regions"). In some embodiments, the term "antibody component" encompasses any protein having a binding domain, which is homologous or largely homologous to an immunoglobulin-binding domain. In particular embodiments, an included "antibody component"

encompasses polypeptides having a binding domain that shows at least 99% identity with an immunoglobulin binding domain. In some embodiments, an included "antibody component" is any polypeptide having a binding domain that shows at least 70%, 75%, 80%, 85%, 90%, 95% or 98% identity with an immunoglobulin binding domain, for example a reference immunoglobulin binding domain. An included "antibody component" may have an amino acid sequence identical to that of an antibody (or a portion thereof, e.g., an antigen-binding portion thereof) that is found in a natural source. An antibody component may be monospecific, bi-specific, or multi-specific. An antibody component may include structural elements characteristic of any immunoglobulin class, including any of the human classes: IgG, IgM, IgA, IgD, and IgE. It has been shown that the antigen-binding function of an antibody can be performed by fragments of a full-length antibody. Such antibody embodiments may also be bispecific, dual specific, or multi-specific formats specifically binding to two or more different antigens. Examples of binding fragments encompassed within the term "antigen-binding portion" of an antibody include (i) a Fab fragment, a monovalent fragment consisting of the $V_H$, $V_L$, $C_H1$ and $C_L$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_H$ and $V_L$ domains of a single arm of an antibody, (v) a dAb fragment (Ward et al., (1989) Nature 341:544-546), which comprises a single variable domain; and (vi) an isolated complementarity determining region (CDR). Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). In some embodiments, an "antibody component", as described herein, is or comprises such a single chain antibody. In some embodiments, an "antibody component" is or comprises a diabody. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., (1993) Proc. Natl. Acad. Sci. USA 90:6444-6448; Poljak, R. J., (1994) Structure 2(12):1121-1123). Such antibody binding portions are known in the art (Kontermann and Dubel eds., Antibody Engineering (2001) Springer-Verlag. New York. 790 pp. (ISBN 3-540-41354-5). In some embodiments, an antibody component is or comprises a single chain "linear antibody" comprising a pair of tandem Fv segments ($V_H$-$C_H1$-$V_H$-$C_H1$) which, together with complementary light chain polypeptides, form a pair of antigen binding regions (Zapata et al., (1995) Protein Eng. 8(10): 1057-1062; and U.S. Pat. No. 5,641,870). In some embodiments, an antibody component may have structural elements characteristic of chimeric or humanized antibodies. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some embodiments, an antibody component may have structural elements characteristic of a human antibody.

Antibody fragment: As used herein, an "antibody fragment" includes a portion of an intact antibody, such as, for example, the antigen-binding or variable region of an antibody. Examples of antibody fragments include Fab, Fab', F(ab')$_2$, and Fv fragments; triabodies; tetrabodies; linear antibodies; single-chain antibody molecules; and multi specific antibodies formed from antibody fragments. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In many embodiments, an antibody fragment contains sufficient sequence of the parent antibody of which it is a fragment that it binds to the same antigen as does the parent antibody; in some embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')$_2$ fragment, scFv fragment, Fv fragment, dsFv diabody, dAb fragment, Fd' fragment, Fd fragment, and an isolated complementarity determining region (CDR) region. An antigen binding fragment of an antibody may be produced by any means. For example, an antigen binding fragment of an antibody may be enzymatically or chemically produced by fragmentation of an intact antibody and/or it may be recombinantly produced from a gene encoding the partial antibody sequence. Alternatively or additionally, antigen binding fragment of an antibody may be wholly or partially synthetically produced. An antigen binding fragment of an antibody may optionally comprise a single chain antibody fragment. Alternatively or additionally, an antigen binding fragment of an antibody may comprise multiple chains which are linked together, for example, by disulfide linkages. An antigen binding fragment of an antibody may optionally comprise a multimolecular complex. A functional antibody fragment typically comprises at least about 50 amino acids and more typically comprises at least about 200 amino acids.

Approximately: As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (for example when the one or more values of interest define a sufficiently narrow range that application of such a percentage variance would obviate the stated range).

Associated with: Two events or entities are "associated" with one another, as that term is used herein, if the presence, level and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biocompatible: The term "biocompatible", as used herein, refers to materials that do not cause significant harm to living tissue when placed in contact with such tissue, e.g., in vivo. In some embodiments, materials are "biocompatible" if they are not toxic to cells. In some embodiments, materials are "biocompatible" if their addition to cells in vitro results in less than or equal to 20% cell death, and/or their administration in vivo does not induce significant inflammation or other such adverse effects.

Biodegradable: As used herein, the term "biodegradable" refers to materials that, when introduced into cells, are broken down (e.g., by cellular machinery, such as by enzymatic degradation, by hydrolysis, and/or by combinations thereof) into components that cells can either reuse or dispose of without significant toxic effects on the cells. In some embodiments, components generated by breakdown of a biodegradable material are biocompatible and therefore do not induce significant inflammation and/or other adverse effects in vivo. In some embodiments, biodegradable polymer materials break down into their component monomers. In some embodiments, breakdown of biodegradable materials (including, for example, biodegradable polymer materials) involves hydrolysis of ester bonds. Alternatively or additionally, in some embodiments, breakdown of biodegradable materials (including, for example, biodegradable polymer materials) involves cleavage of urethane linkages. Exemplary biodegradable polymers include, for example, polymers of hydroxy acids such as lactic acid and glycolic acid, including but not limited to poly(hydroxyl acids), poly(lactic acid)(PLA), poly(glycolic acid)(PGA), poly(lactic-co-glycolic acid)(PLGA), and copolymers with PEG, polyanhydrides, poly(ortho)esters, polyesters, polyurethanes, poly(butyric acid), poly(valeric acid), poly(caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

Biologically active agent: As used herein, the term "biologically active agent" refers to an agent that has a particular biological effect when administered to a subject, e.g., a human. In some embodiments, a biologically active agent may be a therapeutically active agent, a cosmetically active agent, and/or a diagnostically active agent. In some embodiments, a biologically active agent may be or comprise an entity or moiety that would be classified as an "Active Pharmaceutical Ingredient" by the United States Food and Drug Administration. In some embodiments, a biologically active agent is a large agent. In some embodiments, a biologically active agent may be or comprise an agent whose presence correlates with a desired pharmacologic and/or therapeutic, cosmetic, and/or diagnostic effect. In some embodiments, a biologically active agent is characterized in that its biological effect is dose-dependent (e.g., increases with increasing dose, optionally in a linear manner over at least a first range of concentrations). In some embodiments, an agent is not considered to be a "biologically active agent" if it merely enhances delivery of a different agent that in fact achieves the desired effect.

Botulinum macroemulsion composition: The term "botulinum macroemulsion composition," as used herein, refers to any macroemulsion composition in which at least one macroemulsion includes botulinum toxin. The botulinum toxin may be present within the macroemulsion, on the macroemulsion surface and/or within a micellar membrane defining the macroemulsion.

Botulinum nanoemulsion composition: The term "botulinum nanoemulsion composition," as used herein, refers to any nanoemulsion composition in which at least one nanoemulsion includes botulinum toxin. The botulinum toxin may be present within the nanoemulsion, on the nanoemulsion surface and/or within a micellar membrane defining the nanoemulsion.

Botulinum toxin: The term "botulinum toxin," as used herein, refers to any neurotoxin produced by Clostridium botulinum. Except as otherwise indicated, the term encompasses fragments or portions (e.g., the light chain and/or the heavy chain) of such neurotoxin that retain appropriate activity (e.g., muscle relaxant activity). The phrase "botulinum toxin," as used herein, encompasses the botulinum toxin serotypes A, B, C, D, E, F, and G. Botulinum toxin, as used herein, also encompasses both a botulinum toxin complex (i.e., for example, the 300, 600, and 900 kDa complexes) as well as the purified (i.e., for example, isolated) botulinum toxin (i.e., for example, about 150 kDa). "Purified botulinum toxin" is defined as a botulinum toxin that is isolated, or substantially isolated, from other proteins, including protein that for a botulinum toxin complex. A purified toxin may be greater than 95% pure, and preferably is greater than 99% pure. Those of ordinary skill in the art will appreciate that the present invention is not limited to any particular source of botulinum toxin. For example, botulinum toxin for use in accordance with the present invention may be isolated from *Clostridium botulinum*, may be chemically synthesized, may be produced recombinantly (i.e., in a host cell or organism other than *Clostridium botulinum*), etc. The botulinum may be genetically engineered or chemically modified to act longer or shorter in duration than botulinum toxin serotype A.

Carrier: as used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Combination therapy: As used herein, the term "combination therapy" refers to those situations in which a subject is simultaneously exposed to two or more therapeutic regimens (e.g., two or more therapeutic agents, a therapeutic agent and a therapeutic modality, etc.). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agents and/or modalities to a subject receiving the other agents or modalities in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Comparable: As used herein, the term "comparable" refers to two or more agents, entities, situations, sets of conditions, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Composition: Those skilled in the art will appreciate that the term "composition", as used herein, may be used to refer to a discrete physical entity that comprises one or more specified components. In general, unless otherwise specified, a composition may be of any form—e.g., gas, gel, liquid, solid, etc.

Comprising: A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Emulsion: The term "emulsion" is used herein consistent with the understanding in the art of "a system . . . consisting of a liquid dispersed with or without an emulsifier in an immiscible liquid usually in droplets of larger than colloidal size". See, for example, definition in Medline Plus Online Medical Dictionary, Merriam Webster (2005).

Excipient: as used herein, refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Human: In some embodiments, a human is an embryo, a fetus, an infant, a child, a teenager, an adult, or a senior citizen.

Hydrophilic: As used herein, the term "hydrophilic" and/or "polar" refers to a tendency to mix with, or dissolve easily in, water.

Hydrophobic: As used herein, the term "hydrophobic" and/or "non-polar", refers to a tendency to repel, not combine with, or an inability to dissolve easily in, water.

Improve, increase or reduce: As used herein or grammatical equivalents thereof, the terms "improve", "increase" or "reduce" indicate values that are relative to a baseline measurement, such as a measurement in the same individual prior to initiation of a treatment described herein, or a measurement in a control individual (or multiple control individuals) in the absence of the treatment described herein. In some embodiments, a "control individual" is an individual afflicted with the same form of disease or injury as an individual being treated.

Large molecule: The term "large molecule" is generally used herein to describe a molecule that is greater than about 100 kilodaltons (KDa) in size. In some embodiments, a large molecule is greater than about 110 KDa, 120 KDa, 130 KDa, 140 KDa, 150 KDa, 160 KDa, 170 KDa, 180 KDa, 190 KDa, 200 KDa, 250 KDa, 300 KDa, 400 KDa, or 500 KDa. In some embodiments, a large molecule is a polymer or comprises a polymeric moiety or entity. In some embodiments, a large molecule is or comprises a polypeptide. In some embodiments, a large molecule is or comprises a nucleic acid.

Large agent: The term "large agent" as used herein generally refers to an agent having a molecular weight that is greater than about 100 kilodaltons (KDa) in size. In some embodiments, a large molecule is greater than about 110 KDa, 120 KDa, 130 KDa, 140 KDa, 150 KDa, 160 KDa, 170 KDa, 180 KDa, 190 KDa, 200 KDa, 250 KDa, 300 KDa, 400 KDa, or 500 KDa. In some embodiments, a large agent is a biologically active agent. In some embodiments, a large agent is or comprises one or more large molecules. In some embodiments, a large agent is or comprises one or more molecular complexes. In some embodiments, a large agent is or comprises a polypeptide. In some embodiments, a large agent is or comprises a complex of polypeptides. In some embodiments, a large agent is or comprises a bacterial toxin (e.g., a botulinum toxin). In some embodiments, a large agent is or comprises an antibody agent.

Macroemulsion: The term "macroemulsion," as used herein, refers to an emulsion in which at least some droplets have diameters in the several hundred nanometers to micrometers size range. As will be understood by those of ordinary skill in the art, a macroemulsion is characterized by droplets greater than 300 nm in diameter. In some embodiments, a macroemulsion composition utilized in accordance with the present disclosure includes one or more large agents or one or more biologically active agents. In some embodiments, a large agent included in a macroemulsion composition may be a biologically active agent. It will be appreciated by those of ordinary skill in the art that a macroemulsion composition for use in accordance with the present disclosure may be prepared according to any available means including, for example, chemical or mechanical means. In some embodiments, droplets in a macroemulsion have a size within a range of about 301 nm and about 1000 µm. In some embodiments, a macroemulsion has droplets in a size distribution of between about 301 nm and about 1000 µm. In some embodiments, droplets in a macroemulsion have a size within a range of about 500 nm and about 5000 µm. In some embodiments, a macroemulsion has droplets in a size distribution of between about 500 nm and about 5000 µm.

Microneedle: The term "microneedle" as used herein generally refers to an elongated structure that is of suitable length, diameter, and shape to penetrate skin. In some embodiments, a microneedle is arranged and constructured (by itself or within a device) to minimize contact with nerves when inserted into skin, while still creating efficient pathways for drug delivery. In some embodiments, a microneedle has a diameter which is consistent along the microneedle's length. In some embodiments, a microneedle has a diameter that changes along the microneedle's length. In some embodiments, a microneedle has a diameter that tapers along the microneedle's length. In some embodiments, a microneedle's diameter is narrowest at the tip that penetrates skin. In some embodiments, a microneedle may be solid. In some embodiments, a microneedle may be hollow. In some embodiments a microneedle may be tubular. In some embodiments, a microneedle may be sealed on one end. In some embodiments, a plurality of microneedles is utilized. In some embodiments, a plurality of microneedles is utilized in an array format. In some embodiments, a microneedle may have a length within a range of about 1 µm to about 4,000 µm. In some embodiments, a microneedle may have a length of between about 1 µm to about 2,000 µm. In some embodiments, a microneedle may have a length of between about 50 µm to about 400 µm. In some embodiments, a microneedle may have a length of between about 800 µm to about 1500 µm.

Nanoemulsion: The term "nanoemulsion," as used herein, refers to an emulsion in which at least some droplets have diameters in the nanometer size range. As will be understood by those of ordinary skill in the art, a nanoemulsion is characterized by droplets 300 nm or smaller in diameter. In some embodiments, a nanoemulsion composition utilized in accordance with the present disclosure includes one or more large agents or one or more biologically active agents. In some embodiments, a large agent included in a nanoemulsion composition may be a biologically active agent. It will be appreciated by those of ordinary skill in the art that a nanoemulsion composition for use in accordance with the present disclosure may be prepared according to any available means including, for example, chemical or mechanical means. In some embodiments, droplets in a nanoemulsion have a size within a range of about 1 nm and about 300 nm. In some embodiments, a nanoemulsion has droplets in a size distribution of between about 1 nm and about 300 nm.

Nanoparticle: As used herein, the term "nanoparticle" refers to a solid particle having a diameter of less than 300 nm, as defined by the National Science Foundation. In some embodiments, a nanoparticle has a diameter of less than 100 nm as defined by the National Institutes of Health.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the patient is receiving or has received certain therapy to diagnose and/or to treat a disease, disorder, or condition.

Penetration enhancing agent: As used herein, the term "penetration enhancing agent" refers to an agent whose presence or level correlates with increased penetration of an agent of interest across skin, as compared with that observed in its absence. In some embodiments, a penetration enhancing agent is characterized in that it degrades and/or disrupts skin structure. In some embodiments, a penetration enhancing agent is or comprises a chemical agent (e.g., a chemical or enzyme, for example) For example, chemical agents that that may damage, disrupt, and/or degrade one or more stratum corneum components) may include, for example, alcohols, such as short chain alcohols, long chain alcohols, or polyalcohols; amines and amides, such as urea, amino acids or their esters, amides, AZONE®, derivatives of AZONE®, pyrrolidones, or derivatives of pyrrolidones; terpenes and derivatives of terpenes; fatty acids and their esters; macrocyclic compounds; tensides; or sulfoxides (e.g., dimethylsulfoxide (DMSO), decylmethylsulfoxide, etc.); surfactants, such as anionic, cationic, and nonionic surfactants; polyols; essential oils; and/or hyaluronidase. In some embodiments, a penetration enhancing agent may be an irritant in that an inflammatory and/or allergic reaction occurs when the agent is applied to skin. In some embodiments, a penetration enhancing agent is not an irritant. In some embodiments, a penetration enhancing agent may be or comprise a chemical agent that does not damage, disrupt, or degrade skin structure but whose presence or level nonetheless correlates with increased penetration of an agent of interest across skin, as compared with that observed in its absence. In some embodiments, co-peptides, carrier molecules, and carrier peptides may be penetration enhancing agents which do not damage, disrupt, and/or degrade skin structure(s). In some embodiments, co-peptides, carrier molecules, and carrier peptides may be penetration enhancing agents which do not irritate the skin. The term "penetration enhancing agent" does not encompass mechanical devices (e.g., needles, scalpels, etc.), or equivalents thereof (e.g., other damaging treatments). Also, those skilled in the art will appreciate that a structure such as a nanoparticle or an emulsion is not a chemical agent and therefore not a chemical penetration enhancing agent even if its presence correlates with enhanced skin penetration of an agent of interest that may be associated with the structure.

Pharmaceutical composition: As used herein, the term "pharmaceutical composition" refers to a composition in which an active agent is formulated together with one or more pharmaceutically acceptable carriers. In some embodiments, an active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for topical administration, for example, a sterile solution or suspension, or sustained-release formulation, as a gel, cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the term "pharmaceutically acceptable" applied to a carrier, diluent, or excipient used to formulate a composition as disclosed herein means that the carrier, diluent, or excipient must be compatible with other ingredients of the composition and not deleterious to a recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting a subject compound from one organ, or portion of the body, to another organ, or portion of the body. Each carrier must be "acceptable" in the sense of being compatible with other ingredients of the formulation and not injurious to a subect or patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, medium chain triglycerides, and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Premix: The term "premix" as used herein, refers to any combination of components that is subsequently used to generate a nanoemulsion composition or according to the present invention. For example, a premix is any collection of ingredients that, when subjected to high shear force, generates nanoemulsions according to the present invention. In some embodiments, a premix is a collection of ingredients that, when subjected to high shear force, generates a nanoemulsion composition such as a uniform nanoemulsion composition. A premix often contains a liquid dispersion medium and other components sufficient to generate nanoemulsion within the dispersion medium. According to some embodiments of the present disclosure, one or more large agents may be included in a premix. According to some embodiments of the present disclosure, one or more biologically agents may be included in a premix. According to the present invention, botulinum toxin may be included in a premix. According to the present invention, one or more antibodies may be included in a premix. In some embodiments, a premix may contain one or more surfactants, penetrating enhancers, and/or other agents. In some embodiments, a premix comprises a solution. In some embodiments in which a premix comprises botulinum toxin, an antibody, another biologically active agent and/or penetration enhancing agent, the botulinum toxin, the antibody, another biologically active agent and/or penetration enhancing agent, is in solution before high shear force is applied to the premix.

Prevent or prevention: as used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Polypeptide: The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Reference: As used herein describes a standard or control relative to which a comparison is performed. For example, in some embodiments, an agent, animal, individual, population, sample, regimen, sequence or value of interest is compared with a reference or control agent, animal, individual, population, sample, regimen, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Self-administration: The term "self-administration," as used herein, refers to the situation where a subject has the ability to administer a composition to him or herself without requiring medical supervision. In some embodiments of the invention, self-administration may be performed outside of a clinical setting. To give but one example, in some embodiments of the invention, a facial cosmetic cream may be administered by a subject in one's own home.

Small Molecule: In general, a "small molecule" is understood in the art to be an organic molecule that is less than about 5 kilodaltons (Kd) in size. In some embodiments, a small molecule is less than about 3 Kd, 2 Kd, or 1 Kd. In some embodiments, a small molecule is less than about 800 daltons (D), 600 D, 500 D, 400 D, 300 D, 200 D, or 100 D. In some embodiments, small molecules are non-polymeric. In some embodiments, small molecules are not proteins, peptides, or amino acids. In some embodiments, small molecules are not nucleic acids or nucleotides. In some embodiments, small molecules are not saccharides or polysaccharides.

Subject: As used herein "subject" means an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, an appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans. In some embodiments, an agent is not considered to be a "therapeutic agent" if it merely enhances delivery of a different agent that in fact achieves the desired effect.

Therapeutically effective amount: As used herein, is meant an amount that produces a desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of a disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by a disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Therapeutic regimen: A "therapeutic regimen", as that term is used herein, refers to a dosing regimen whose administration across a relevant population may be correlated with a desired or beneficial therapeutic outcome.

Treatment: As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Uniform: The term "uniform," when used herein in reference to a nanoemulsion composition, refers to a nanoemulsion composition in which individual droplets have a specified range of droplet diameter sizes. For example, in some embodiments, a uniform nanoemulsion composition is one in which the difference between the minimum diameter and maximum diameter does not exceed approximately 300, 250, 200, 150, 100, 90, 80, 70, 60, 50, or fewer nm. In some embodiments, droplets (e.g., large agent-containing droplets) within inventive uniform large agent nanoemulsion compositions have diameters that are smaller than about 300, 250, 200, 150, 130, 120, 115, 110, 100, 90, 80 nm, or less. In some embodiments, droplets (e.g., large agent-containing droplets) within inventive uniform large agent nanoemulsion compositions have diameters within a range of about 10 and about 300 nanometers. In some embodiments, droplets within inventive uniform large agent nanoemulsion compositions have diameters within a range of about 10-300, 10-200, 10-150, 10-130, 10-120, 10-115, 10-110, 10-100, or 10-90 nm. In some embodiments, droplets (e.g., large agent-containing droplets) within inventive large agent nanoemulsion compositions have an average droplet size that is under about 300, 250, 200, 150, 130, 120, or 115, 110, 100, or 90 nm. In some embodiments, the average droplet size is within a range of about 10-300, 50-250, 60-200, 65-150, 70-130 nm. In some embodiments, the average droplet size is about 80-110 nm. In some embodiments, the average droplet size is about 90-100 nm. In some embodiments, a majority of droplets (e.g., large agent-containing droplets) within inventive uniform nanoemulsion compositions have diameters below a specified size or within a specified range. In some embodiments, a majority is more than 50%, 60%, 70%, 75%, 80%, 85%, 90%, 95%, 96%, 97%, 98%, 99%, 99.5%, 99.6%, 99.7%, 99.8%, 99.9% or more of the droplets in the composition. In some embodiments of the invention, a uniform nanoemulsion composition is achieved by microfluidization of a sample.

Detailed Description of Certain Embodiments

Transdermal Drug Delivery

In some embodiments, the present invention provides technologies for administering large agents (e.g., botulinum toxin, antibodies) transdermally. In some embodiments, the present disclosure teaches that particularly advantageous results are achieved when microneedling technologies are combined with emulsion compositions. In some embodiments, microneedling technologies are combined with lotion, cream, or liquid compositions, which in turn may be or comprise emulsion compositions (e.g., macroemulsion compositions and/or nanoemulsion compositions). In some embodiments, provided technologies do not utilize penetration enhancing agents. In some embodiments, provided technologies do not utilize chemical penetration enhancing agents which damage, disrupt, and/or degrade the skin. In some embodiments, provided technologies do not utilize chemical penetration enhancing agents.

Human skin comprises the dermis and the epidermis. The epidermis has several layers of tissue, namely, stratum corneum, stratum lucidum, stratum granulosum, stratum spinosum, and stratum basale (identified in order from the outer surface of the skin inward).

The stratum corneum presents the most significant hurdle in transdermal delivery generally, and presumably of large agents in particular. The stratum corneum is typically about 10-15 μm thick, and it consists of flattened, keratised cells (corneocytes) arranged in several layers. The intercellular space between the corneocytes is filled with lipidic structures, and may play an important role in the permeation of substances through skin (Bauerova et al., 2001, *European Journal of Drug Metabolism and Pharmacokinetics,* 26:85).

The rest of the epidermis below the stratum corneum is approximately 150 μm thick. The dermis is about 1-2 mm thick and is located below the epidermis. The dermis is innervated by various capillaries as well as neuronal processes.

Transdermal administration generally has been the subject of research in attempts to provide an alternative route of administration without undesirable consequences associated with injections and oral delivery. For example, needles often cause localized pain, and potentially expose patients receiving injections to blood borne diseases. Oral administration often suffers from poor bioavailability of medications due to the extremely acidic environment of the patient's stomach.

Efforts have been made to develop transdermal administration techniques for certain pharmaceuticals in an attempt to overcome these shortcomings by providing noninvasive administration. It is generally desirable with transdermal administration to minimize damage to a patient's skin. Thus, transdermal administration may reduce or eliminate pain associated with injections, reduce the likelihood of blood contamination, and improve the bioavailability of drugs once they are incorporated systemically.

Traditionally, attempts at transdermal administration have been focused on disruption and/or degradation of the stratum corneum. Some attempts have included using chemical penetration enhancing agents. Penetration enhancing agents may function to degrade and/or disrupt skin structure. In some embodiments, a penetration enhancing agent is or comprises a chemical agent (e.g., a chemical or enzyme, for example that may disrupt and/or degrade one or more stratum corneum components). In some embodiments, a penetration enhancing agent may be an irritant in that an inflammatory and/or allergic reaction occurs when the agent is applied to skin.

"However, the major limitation for penetration enhancers is that their efficacy is often closely correlated with the occurrence of skin irritation." Alkilani, A. Z., et al., "Transdermal drug delivery: Innovative pharmaceutical developments based on disruption of the barrier properties of the stratum corneum." Pharmaceutics. 7:438-470 (2015). Penetration enhancing agents tend to have poor efficacy and safety profiles. "They do not achieve the desired skin disruption and their ability to increase transport across the skin is low and variable." Id.

Some attempts have included using mechanical apparatus to bypass or ablate portions of the stratum corneum. In addition, attempts have included use of ultrasound or iontophoresis to facilitate the penetration of pharmaceuticals through the skin. In most cases, the goal has been to enable a pharmaceutical agent, typically a small molecule, so that the agent may pass to the capillary bed in the dermis where the agent may be systemically incorporated into the subject to achieve a therapeutic effect. These methods are limited by the amount of energy that may be applied to the skin without causing discomfort and/or skin damage.

Transdermal Delivery of Large Molecules

Microneedling technologies have been shown to enhance transdermal delivery of a variety of small agents, such as calcein (~623 Da), desmopressin (~1070 Da), diclofenac (~270 Da), methyl nicotinate (~40 Da), bischloroethyl nitrosourea (~214 Da), insulin (~5.8 KDa), bovine serum albumin (~66.5 KDa) and ovalbumin (~45 KDa), however until the present disclosure, delivery of large agents, particularly those of 100 KDa or greater, remained problematic.

Transdermal delivery of large molecules is recognized to pose a major challenge. Until the present disclosure, microneedling, and in particular microneedle skin preconditioning, had not been considered to impact or effect transdermal administration of large agents. For example, a study of the use of solid microneedles for delivery of four hydrophilic peptides of low molecular weight tetrapeptide-3 (456.6 Da); hexapeptide (498.6 Da); acetyl hexapeptide-3 (889 Da); and oxytocin (1007.2 Da), as well as L-carnitine (161.2 Da), showed that while microneedle pretreatment significantly enhanced the penetration of each of these peptides, the skin permeation of the peptides depends on their molecular weight and decreases as the molecular weight increases. Zhang, S., et al., "Enhanced delivery of hydrophilic peptides in vitro by transdermal microneedle pretreatment." Acta Pharmaceutica Sinica B. 4(1):100-104 (2014).

When sandpaper abrasion, tape stripping, and a single puncture hypodermic needle model of MSC were compared in a study of the effect of molecular size of larger FITC (fluorescein isothiocyanate) conjugated molecules on transdermal delivery, it was found that for all methods, as well as when tested on untreated skin, transdermal drug delivery was again shown to be reduced as the size of the test molecules increased (4.3, 9.6 and 42.0 KDa FITC conjugates). Tape stripping was the most effective technique, while sandpaper abrasion was found to be the most skin damaging. Wu, X., et al., "Effects of pretreatment of needle puncture and sandpaper abrasion on the in vitro skin permeation of fluorescein isothiocyanate (FITC)-dextran." International Journal of Pharmaceutics. 316:102-108 (2006).

Other studies attempted delivery of even larger molecules: Cascade Blue (CB, Mw 538), Dextran-Cascade Blue (DCB, Mw 10 kDa), and FITC coupled Dextran (FITC-Dex, Mw 72 kDa). In that study, microneedles of varying lengths (300, 550, 700 or 900 μm) were used to puncture dermatomed human skin and the diffusion of each of the aforementioned compounds was assessed. While transportation of each of the compounds was seen with all but the 300 μm microneedle array, degradation of the DCB and FITC-Dex was observed.

As the prior art demonstrates, as molecular size increases, transdermal penetration using MSC ("microneedle skin conditioning") decreases, to the point where it is de minimis and even non-existent. Even in those cases where some de minimis penetration was observed, the larger molecules were observed to become degraded and biologically inactive. Accordingly, until the present invention, one of skill would have predicted that even with the use of mechanical or chemical permeation enhancers a large agent such as botulinum which, at approximately 150 KDa, is more than twice the size of FITC-Dex, would have no permeation at all, let alone bioavailability of the intact active agent. Botulinum is a complex protein, requiring three regions or functional moieties to be intact in order for the protein to be biologically active. Thus, damage to any one of the three regions of the protein make the protein inactive biologically. Per Johnson, E., et al., "Botulinum toxin is very susceptible to denaturation due to surface denaturation, heat, and alkaline conditions." US Patent Publication No. 5512547. Thus, under the microneedling conditions described by Wu, one would expect a significant level of degradation and inactivation of the botulinum.

Among other things, the present disclosure demonstrates that microneedling technologies can enhance transdermal delivery (e.g., of large agents, particularly from macroemulsion or nanoemulsion compositions), when no other penetration enhancing agent, particularly, a disrupting agent (e.g., no chemical penetration enhancing agent and no other technology that disrupts or punctures skin structure) is utilized.

Microneedling

The present disclosure provides the surprising finding that MSC can surprisingly improve transdermal delivery of large agents. In some embodiments, a large agent may be formulated as a cream and/or lotion. In some embodiments a large agent may be combined with one or more biologically active agents. In some embodiments, a large agent may be formulated as or in an emulsion (e.g., as a macroemulsion or as a nanoemulsion) composition. In some embodiments, an emulsion comprising one or more large agents may be formulated as a cream and/or lotion.

In some embodiments, microneedle (MN) arrays for use in accordance with the present disclosure are or share features with minimally invasive systems, developed to overcome some of the disadvantages commonly associated with the use of hypodermic and subcutaneous needles, as well as improve patient comfort and compliance. Such disadvantages include, for example, potential for needle tip misplacement with a hypodermic needle because a health professional cannot visualize where exactly the needle is going; such needle misplacement can result in adverse reactions such as a drooping eyelid ("ptosis") when botulinum is injected incorrectly in the face. MN would be less prone to such a problem. Other advantages of MN are that they may not cause bleeding, minimize introduction of pathogens through MN produced holes, and eliminate transdermal dosing variability. Other advantages are the possibility of self-administration, reduce risk of accidental needle stick injuries, reduce risk of transmitting infection, and ease of disposal. In some embodiments, MN are multiple microscopic projections assembled on one side of a support, such as a patch or a device (e.g., stamp, roller, array, applicator, pen).

In some embodiments, MN for use in accordance with the present disclosure may be designed and/or constructed in arrays in order to improve skin contact and facilitate penetration into the skin. In some embodiments, utilized MN are of suitable length, width, and shape to minimize contact with nerves when inserted into the skin, while still creating efficient pathways for drug delivery. Alkilani, A. Z., et al., "Transdermal drug delivery: Innovative pharmaceutical developments based on disruption of the barrier properties of the stratum corneum." Pharmaceutics. 7:438-470 (2015).

In some embodiments, a suitable MN may be solid, coated, porous, dissolvable, hollow, or hydrogel MN. Solid MN create microholes in the skin, thereby increasing transport of a drug formulation (e.g., "poke and patch" methods). Coated MN allow for rapid dissolution of a coated drug into the skin (e.g., "coat and poke" methods). Dissolvable MN allow for rapid and/or controlled release of a drug incorporated within the microneedles. Hollow MN may be used to puncture the skin and enable release of a composition following active infusion or diffusion of a formulation through a microneedle's bores (e.g., "poke and flow" methods"). In the case of dissolvable MN, MN can act as a drug depot, holding a drug composition until released by dissolution in the case of dissolvable MN or swelling in the case of hydrogel MN (e.g., "poke and release" methods). However, as already described herein, in many embodiments, the large agent is not delivered by injection via one or more microneedles. That is, in many embodiments, any microneedle utilized in accordance with such embodiments is not coated, loaded, or fabricated with the large agent in any way that would achieve delivery of the large agent. Alternatively, in some embodiments, as described herein, a MN, utilized in accordance with the present disclosure (whether in MSC or otherwise), may comprise and/or deliver a large agent, if the large agent is formulated in a macro- or nano-emulsion composition as described herein. Thus, as will be appreciated by those skilled in the art reading the specification described herein, treatment of skin with microneedle(s) that deliver the large agent (e.g., by injection through a microneedle, by the release of a microneedle coating or by the release from a dissolving microneedle) is not microneedle skin conditioning.

In some embodiments, a microneedle has a diameter which is consistent throughout the microneedle's length. In some embodiments, the diameter of a microneedle is greatest at the microneedle's base end. In some embodiments, a microneedle tapers to a point at the end distal to the microneedle's base. In some embodiments, a microneedle may be solid. In some embodiments, a microneedle may be hollow. In some embodiments a microneedle may be tubular. In some embodiments, a microneedle may be sealed on one end. In some embodiments, a microneedle is part of an array of microneedles. In some embodiments, a microneedle may have a length of between about 1 µm to about 4,000 µm. In some embodiments, a microneedle may have a length of between about 1 µm to about 2,000 µm. In some embodiments, a microneedle may have a length of between about 50 µm to about 400 µm. In some embodiments, a microneedle may have a length of between about 800 µm to about 1500 µm.

In some embodiments, MN for use in accordance with the present disclosure may be fabricated from different materials, using technologies including, but not limited to micromolding processes or lasers. In some embodiments, MN may be manufactured using various types of biocompatible materials including polymers, metal, ceramics, semiconductors, organics, composites, or silicon. Unless they are designed to break off into the skin and dissolve, in some embodiments, microneedles have the mechanical strength to remain intact and to deliver drugs, or collect biological fluid, while being inserted into the skin and/or removed from the skin after insertion. In some embodiments MN are capable of remaining in place for up to a number of days before intact removal. In some embodiments, microneedles may be sterilizable using standard technologies. In some embodiments, MN are biodegradable. In some embodiments, MN comprise a polymeric material. In some embodiments the polymeric material comprises poly-L-lactic acid, poly-glycolic acid, poly-carbonate, poly-lactic-co-glycolic acid (PLGA), polydimethylsiloxane, polyvinylpyrrolidone (PVP), a copolymer of methyl vinyl ether and maleic anhydride, sodium hyaluronate, carboxymethyl cellulose, maltose, dextrin, galactose, starch, gelatin, or a combination thereof.

Suitable MN arrays and MSC devices for use in combination with compositions comprising large agents for transdermal delivery of large agents include devices such as those described in e.g., U.S. Pat. Nos. 6,334,856; 6,503,231; 6,908,453; 8,257,324; and 9,144,671.

Large Agents

In some embodiments, compositions provided and/or utilized as described herein comprise one or more large agents. In some embodiments, utilized large agents are biologically active agents (e.g., therapeutically active agents). Among other things, the present disclosure provides strategies for topical administration of compositions comprising a large agent in combination with MSC.

1. Protein Agents

Any of a variety of protein agents may be incorporated in provided compositions and administered in combination with MSC. In some embodiments, protein agents may be peptide agents. In some embodiments, a peptide has a molecular weight greater than 100 KDa. In some embodiments, a peptide agent has a molecular weight of at least 150 KDa. In some embodiments, a peptide agent is comprised solely of naturally occurring amino acids. In some embodiments, a peptide agent comprises one or more non-naturally occurring amino acid.

(i) Botulinum Toxin

In some embodiments, a large agent may be a botulinum toxin. Botulinum toxin (BTX) BTX is produced in nature by the anaerobic, gram positive bacillus *Clostridium botulinum* and is a potent polypeptide neurotoxin. Most notably, BTX causes a neuroparalytic illness in humans and animals referred to as botulism. BTX can apparently pass through the lining of the gut and attack peripheral motor neurons. Symptoms of botulinum toxin intoxication can progress from difficulty walking, swallowing, and speaking to paralysis of the respiratory muscles, and death.

The molecular weight of a botulinum toxin protein molecule, for all seven known botulinum toxin serotypes, is about 150 kDa. Botulinum toxins are released by the Clostridium bacterium as complexes comprising a 150 kDa botulinum toxin protein molecule along with associated non-toxin proteins. Thus, a BTX-A complex can be produced by *Clostridium* bacterium as 900 kDa, 500 kDa and 360 kDa forms. Botulinum toxin types B and $C_1$ are apparently produced as only a 500 kDa complex. Botulinum toxin type D is produced as both 300 kDa and 500 kDa complexes. Finally, botulinum toxin types E and F are produced as only approximately 300 kDa complexes.

BTX complexes (i.e., those compositions having molecular weights greater than about 150 kDa) are believed to contain a non-toxin hemagglutinin protein and a non-toxin and non-toxic non-hemagglutinin protein. These two non-toxin proteins (which along with the botulinum toxin molecule comprise the relevant neurotoxin complex) may act to provide stability against denaturation to the botulinum toxin molecule and protection against digestive acids when toxin is ingested.

Either BTX proteins or BTX complexes may be utilized as known therapeutic agents and/or independently active biologically active agents in accordance with the present invention. Indeed, it will be appreciated by those of ordinary skill in the art that any portion or fragment of a BTX protein or complex that retains the appropriate activity may be utilized as described herein.

In some embodiments, botulinum toxin may be selected from the group consisting of type A, type Ab, type Af, type B, type Bf, type C1, type C2, type D, type E, type F, and type G; mutants thereof; variants thereof; fragments thereof; characteristic portions thereof; and/or fusions thereof. In some embodiments, botulinum toxin is present as any of the subtypes described in Sakaguchi, 1982, *Pharmacol. Ther.*, 19:165; and/or Smith et al., 2005, *Infect. Immun.*, 73:5450; both of which are incorporated herein by reference.

In some embodiments, the present invention provides botulinum toxin compositions. In some embodiments, the present invention provides nanoemulsion botulinum toxin compositions. Commercially available sources of botulinum toxin that may be utilized in accordance with the present invention include, but are not limited to, BOTOX®, DYSPORT® (*Clostridium botulinum* type A toxin hemagglutinin complex with human serum albumin and lactose; Ispen Limited, Berkshire U.K.), Xeomin®, PurTox®, Medy-Tox, NT-201 (Merz Pharmaceuticals), and/or MYOBLOC® (an injectable solution consisting of botulinum toxin type B, human serum albumin, sodium succinate, and sodium chloride, pH 5.6, Elan Pharmaceuticals, Dublin, Ireland), NEURONOX (Medytox), HENGLI (Lanzhou Institute), etc. Those skilled in the art are aware of standard and/or approved administration regimens for such commercially available botulinum toxin compositions and will appreciate that any relevant such compositions and/or regimens may be utilized together with microneedling technologies (e.g., specifically with MSC), as described herein.

In some embodiments, a provided composition comprising a botulinum toxin composition and formulated as a cream and/or lotion comprises between about 1 to about 50,000 Units botulinum toxin per mL. In some embodiments, a provided composition comprising a botulinum toxin composition and formulated as a cream and/or lotion comprises between 500 to about 20,000 Units botulinum toxin per mL. In some embodiments, a provided composition comprising a botulinum toxin composition and formulated as a cream and/or lotion comprises between about 100 to about 2,000 Units botulinum toxin per mL. In some embodiments, a provided composition comprising a botulinum toxin composition and formulated as a cream and/or lotion comprises between about 50 to about 500 Units botulinum toxin per mL. In some embodiments, a provided composition comprising a botulinum toxin composition formulated as a cream and/or lotion comprises between about 25 to about 400 Units botulinum toxin per mL.

In some embodiments, a botulinum toxin composition comprises between about 2 to about 40,000 Units botulinum toxin per mL. In some embodiments, a botulinum toxin composition comprises between about 2 to about 12,000 Units botulinum toxin per mL. In some embodiments, a botulinum toxin composition comprises between about 100 to about 2,000 Units botulinum toxin per mL. In some embodiments, a botulinum toxin composition comprises between about 50 to about 1,000 Units botulinum toxin per mL.

In some embodiments, a botulinum toxin composition includes at least one biologically active agent other than botulinum toxin. Alternatively or additionally, in some embodiments, a botulinum composition is administered in combination with at least one other composition that comprises such a biologically active agent. In some embodiments, a botulinum composition is administered in combination with a penetration enhancing agent. In some embodiments, a botulinum composition is administered in combination with another biologically active agent. In some embodiments, a botulinum composition is administered in combination with another biologically active agent and a penetration enhancing agent.

In some embodiments, biologically active agents utilized in combination with botulinum toxin as described herein may be an agent that acts on or in skin and/or that imparts a therapeutic and/or cosmetic effect. For example, in some embodiments, such a biologically active agent may be selected from therapeutic agents such as anesthetics (e.g, lidocaine), steroids (e.g., hydrocortisone), and/or retinoids (e.g., retin A), cosmetic agents such as dermal fillers, collagen, and/or silicone. In some embodiments, a botulinum composition is administered in combination with delivery modifying agents such as penetration enhancing agents (in some embodiments that are not irritants and/or do not degrade, disrupt and/or damage skin structure(s) and/or skin).

In some embodiments, a non-irritating penetration enhancing agent may be selected from, for example, co-peptides, carrier molecules, and carrier peptides. In some embodiments a carrier molecule is positively charged. In some embodiments, a carrier molecule may be a co-peptide. In some embodiments, a carrier molecule may be a long-chain positively charged polypeptide or a positively charged nonpeptidyl polymer, for example, a polyalkyleneimine. In some embodiments a carrier peptide may be a cationic peptide. In some embodiments, a carrier peptide is a positively charged carrier with the sequence RKKRRQRRRG-$(K)_{15}$-GRKKRRQRRR (SEQ ID NO: 1). In some embodiments, a carrier molecule may be one disclosed in U.S. Patent Publication 2010/0168023 or U.S. Patent Publication 2009/0247464 the contents of which are herein incorporated by reference in their entireties.

In some embodiments, a provided composition comprising both a botulinum toxin nanoemulsion composition and a cream and/or lotion formulation comprises between about 1 to about 50,000 Units botulinum toxin per mL. In some embodiments, a provided composition comprising both a nanoemulsion composition and a cream and/or lotion formulation comprises between about 500 to about 20,000 Units botulinum toxin per mL. In some embodiments, a provided composition comprising both a nanoemulsion composition and a cream and/or lotion formulation comprises between about 100 to about 2,000 Units botulinum toxin per mL. In some embodiments, a provided composition comprising both a botulinum toxin nanoemulsion composition and a cream and/or lotion formulation comprises between about 50 to about 500 Units botulinum toxin per mL. In some embodiments, a provided composition comprising both a botulinum toxin nanoemulsion composition and a cream and/or lotion formulation comprises between about 25 to about 400 Units botulinum toxin per mL.

In some embodiments, a botulinum toxin nanoemulsion composition comprises between about 2 to about 40,000 Units botulinum toxin per mL. In some embodiments, a botulinum toxin nanoemulsion composition comprises between about 2 to about 12,000 Units botulinum toxin per mL. In some embodiments, a botulinum toxin nanoemulsion composition comprises between about 100 to about 2,000 Units botulinum toxin per mL. In some embodiments, a botulinum toxin nanoemulsion composition comprises between about 50 to about 1,000 Units botulinum toxin per mL.

(ii) Antibody Agents

In some embodiments, the present disclosure relates to delivery of antibody agents. In some embodiments, a large agent may be an antibody or a fragment or derivative thereof. Among other things, the present disclosure provides certain compositions comprising antibody agents, and also provides technologies for administration of compositions comprising antibody agents, such administration being in combination with MSC.

In some embodiments, an antibody agent may be suitable for treating a dermatological condition. In some embodiments an antibody agent may be a fusion protein. In some embodiments an antibody agent may be conjugated to another moiety. In some embodiments, an antibody agent may be conjugated to polyethylene glycol.

In some embodiments, an antibody agent targets TNFα (e.g., includes epitope binding elements found in an anti-TNFα antibody such as infliximab, adalimumab, golimumab, etanercept, etanercept-szzs, and/or certolizumab pegol). In some embodiments, an antibody agent targets CD2 (e.g., includes epitope binding elements found in an anti-CD2 antibody such as siplizumab). In some embodiments, an antibody agent targets CD4 (e.g., includes epitope binding elements found in an anti-CD4 antibody such as zanolimumab).

In some embodiments, an antibody agent targets IL-12 (e.g., includes epitope binding elements found in an anti-IL-12 antibody such as briakinumab). In some embodiments, an antibody agent targets IL-17 (e.g., includes epitope binding elements found in an anti-IL-17 antibody such as secukinumab and/or brodalumab). In some embodiments, an antibody agent targets IL-22 (e.g., includes epitope binding elements found in an anti-IL-22 antibody such as fezakinumab). In some embodiments, an antibody agent targets IL-23 (e.g., includes epitope binding elements found in ustekinumab and/or guselkumab).

In some embodiments, an antibody agent composition includes at least one biologically active agent other than an antibody agent. Alternatively or additionally, in some embodiments, an antibody agent composition is administered in combination with at least one other composition that comprises such a biologically active agent. In some embodiments, an antibody agent composition is administered in combination with a penetration enhancing agent. In some embodiments, an antibody agent composition is administered in combination with another biologically active agent. In some embodiments, an antibody agent composition is administered in combination with another biologically active agent and a penetration enhancing agent. In some embodiments, an antibody agent composition is a nanoemulsion. In some embodiments, an antibody agent composition is a cream and/or lotion formulation.

In some embodiments, biologically active agents utilized in combination with an antibody agent as described herein may be an agent that acts on or in skin and/or that imparts a therapeutic and/or cosmetic effect. For example, in some embodiments, such a biologically active agent may be selected from therapeutic agents such as anesthetics (e.g., lidocaine), steroids (e.g., hydrocortisone), and/or retinoids (e.g., retin A), cosmetic agents such as dermal fillers, collagen, and/or silicone. In some embodiments, an antibody agent composition is administered in combination with delivery modifying agents such as penetration enhancing agents (in some embodiments that are not irritants and/or do not degrade, disrupt and/or damage skin structure(s) and/or skin).

In some embodiments, a non-irritating penetration enhancing agent may be selected from, for example, co-peptides, carrier molecules, and carrier peptides. In some embodiments a carrier molecule is positively charged. In some embodiments, a carrier molecule may be a co-peptide. In some embodiments, a carrier molecule may be a long-chain positively charged polypeptide or a positively charged nonpeptidyl polymer, for example, a polyalkyleneimine. In some embodiments a carrier peptide may be a cationic peptide. In some embodiments, a carrier peptide is a positively charged carrier with the sequence RKKRRQRRRG-(K)$_{15}$-GRKKRRQRRR (SEQ ID NO: 1). In some embodiments, a carrier molecule may be one disclosed in U.S. Patent Publication 2010/0168023 or U.S. Patent Publication 2009/0247464 the contents of which are herein incorporated by reference in their entireties.

2. Prophylactic Agents

Any of a variety of prophylactic agents may be incorporated in provided compositions and administered in combination with MSC according to the present invention. In some embodiments, prophylactic agents include, but are not limited to, vaccines. In some embodiments, vaccines may comprise isolated proteins or peptides, inactivated organisms and viruses, dead organisms and virus, genetically altered organisms or viruses, and cell extracts. In some embodiments, prophylactic agents may be combined with interleukins, interferon, cytokines, and adjuvants such as cholera toxin, alum, Freund's adjuvant, etc. In some embodiments, prophylactic agents may include antigens of such bacterial organisms as *Streptococcus pnuemoniae, Haemophilus influenzae, Staphylococcus aureus, Streptococcus pyrogenes, Corynebacterium diphtheriae, Listeria monocytogenes, Bacillus anthraces, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. In some embodiments, these antigens may be in the form of whole killed organisms, peptides, proteins, glycoproteins, carbohydrates, or combinations thereof.

Those skilled in the art will recognize that the preceding paragraphs provide an exemplary, not comprehensive, list of agents that can be delivered using technologies in accordance with the present invention. Any agent may be associated with provided compositions in accordance with the present invention.

Topical Formulations

Compositions as described herein are particularly useful in that they can be used for delivery of large agents to a subject in need thereof via topical and/or transdermal (e.g., by lotions, creams, powders, ointments, liniments, gels, drops, etc.) administration. In some embodiments, provided cream and/or lotion formulations comprising large agents are administered to a subject in need thereof via topical and/or transdermal (e.g., by lotions, creams, powders, ointments, liniments, gels, drops, etc.) administration.

In some embodiments, cream and/or lotion formulations comprise purified water, methylparaben, mineral oil, isopropyl myristate, white petrolatum, emulsifying wax, and propylparaben. In some embodiments, cream and/or lotion formulations comprise purified water, mineral oil, isopropyl myristate, white petrolatum, and emulsifying wax.

In some embodiments, the present invention provides particular cream and/or lotion formulations as described herein. In some embodiments, provided cream and/or lotion formulations comprise water. In some embodiments, provided cream and/or lotion formulations comprise methylparaben. In some embodiments, provided cream and/or lotion formulations comprise mineral oil. In some embodiments, provided cream and/or lotion formulations comprise isopropyl myristate. In some embodiments, provided cream and/or lotion formulations comprise white petrolatum. In some embodiments, provided cream and/or lotion formulations comprise emulsifying wax. In some embodiments, provided cream and/or lotion formulations comprise propylparaben. In some embodiments, provided cream and/or lotion formulations do not comprise any parabens. In some embodiments, provided cream and/or lotion formulations do not comprise methylparaben. In some embodiments, provided cream and/or lotion formulations do not comprise propylparaben. An exemplary lotion formulation is provided in Table 1.

TABLE 1

Exemplary Cream and/or Lotion Formulation

| % w/w | Ingredient |
| --- | --- |
| 72.00 | Purified Water |
| 0.200 | Methylparaben |
| 5.00 | Mineral Oil |

TABLE 1-continued

Exemplary Cream and/or Lotion Formulation

| % w/w | Ingredient |
| --- | --- |
| 5.00 | Isopropyl Myristate |
| 2.000 | White Petrolatum |
| 15.00 | Emulsifying Wax |
| 0.800 | Propylparaben |
| 100 | TOTAL |

In some embodiments, cream and/or lotion formulations may be useful for topical and/or transdermal administration. The present invention encompasses the recognition that provided cream and/or lotion formulations can be particularly useful for delivery of agents to the dermal layer of the skin. In some embodiments, provided cream and/or lotion formulations are formulated for topical and/or transdermal delivery to a subject in need thereof. In some embodiments, provided cream and/or lotion formulations are administered to a subject in need thereof via topical and/or transdermal delivery.

In some embodiments, provided compositions are formulated with cosmetically acceptable components. For example, in some embodiments, provided compositions are formulated with water and also any cosmetically acceptable solvent, in particular, monoalcohols, such as alkanols having 1 to 8 carbon atoms (like ethanol, isopropanol, benzyl alcohol and phenylethyl alcohol), polyalcohols, such as alkylene glycols (like glycerine, ethylene glycol and propylene glycol), and glycol ethers, such as mono-, di-, and tri-ethylene glycol monoalkyl ethers, for example, ethylene glycol monomethyl ether and diethylene glycol monomethyl ether, used singly or in a mixture. Such components can be present, for example, in proportions of up to as much as 60%, 70%, 80%, or 90% by weight, relative to the weight of the total composition.

In some embodiments, provided compositions for topical administration include one or more cosmetically acceptable components that impart appearance attributes desirable or appropriate for a subject to which the composition is to be applied (e.g., a matte appearance, which may be particularly desirable or appropriate for administration to subjects having greasy skin).

In some embodiments, provided compositions are formulated with at least one cosmetically acceptable filler material, for example, in order to obtain a matte product, which may be especially desired for individuals with greasy skin.

In some embodiments, large agents are formulated into compositions suitable for topical administration. Exemplary large agents include those described herein. In some embodiments, provided compositions may be formulated and delivered in combination with MSC so that systemic delivery is achieved; in some embodiments, provided compositions may be formulated and/or delivered so that local, but not systemic, delivery is achieved.

In some embodiments, compositions suitable for topical formulation comprise a penetration enhancing agent. In some embodiments, a penetration enhancing agent degrades, disrupts and/or damages skin structure(s) and/or skin. In some embodiments, a penetration enhancing agent does not degrade, disrupt and/or damage skin structure(s) and/or skin. In some embodiments, a penetration enhancing agent is an irritant. In some embodiments, a penetration enhancing agent is not an irritant.

The present disclosure specifically demonstrates effective and efficient delivery of a therapeutic agent (and, in particular, a large biologic agent, such as botulinum toxin and/or antibody agent) to the dermis using provided compositions in combination with MSC. For example, in some embodiments, the present invention provides methods comprising administration of a composition as described herein without clinically significant side effects. To give but one example, when topical delivery is contemplated, clinically significant side effects include, but are not limited to, unwanted systemic side effects, damage to nervous tissue underlying the dermis (e.g., neuronal paralysis), unwanted effects on muscles (e.g., muscle paralysis), and/or undesirable blood levels of therapeutic agent, etc.

Those of ordinary skill in the art will appreciate that provided compositions may be incorporated into a device such as, for example, a patch. A variety of transdermal patch structures are known in the art; those of ordinary skill will appreciate that provided compositions may readily be incorporated into any of a variety of such structures. In some embodiments, a transdermal patch may comprise a plurality of needles extending from one side of the patch that is applied to the skin, wherein needles extend from the patch to project through the stratum corneum of the skin. In some embodiments, needles do not rupture a blood vessel. In some embodiments, needles do not penetrate deeply enough to reach nerves in the dermis of the skin.

In some embodiments, a transdermal patch includes an adhesive. Some examples of adhesive patches are well known (for example, see U.S. Design Pat. 296,006; and U.S. Pat. Nos. 6,010,715; 5,591,767; 5,008,110; 5,683,712; 5,948,433; and 5,965,154; all of which are incorporated herein by reference). Adhesive patches are generally characterized as having an adhesive layer, which will be applied to a patient's skin, a depot or reservoir for holding a provided composition, and an exterior surface that prevents leakage of the provided composition from the depot. The exterior surface of a patch may be non-adhesive.

In accordance with the present invention, a provided composition is incorporated into a patch so that it remains stable for extended periods of time. For example, in some embodiments, a provided composition may be incorporated into a polymeric matrix that stabilizes an large agent, and permits the agent to diffuse from the matrix and the patch. A provided composition may also be incorporated into an adhesive layer of a patch so that once the patch is applied to the skin, the provided composition may diffuse through the skin. In some embodiments, an adhesive layer may be heat-activated where temperatures of about 37° C. cause the adhesive to slowly liquefy so that the agent diffuses through the skin. The adhesive may remain tacky when stored at less than 37° C., and once applied to the skin, the adhesive loses its tackiness as it liquefies.

In some embodiments, a provided composition can be provided in a depot in a patch so that pressure applied to the patch causes the provided composition to be directed out of the patch through microneedles and through the stratum corneum. Exemplary embodiments of microneedles are described above. Suitable devices for use in administering provided compositions intradermally include devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof.

In some embodiments, for example in order to prolong the effect of a provided composition, it may be desirable to slow absorption of a provided composition into the skin. In some embodiments, this may be accomplished by use of a liquid suspension of crystalline or amorphous material with poor water solubility. The rate of absorption of a provided composition then depends upon its rate of dissolution which, in turn, may depend upon crystal size and crystalline form. In some embodiments, depending upon the ratio of provided composition to polymer and the nature of the particular polymer employed, the rate of provided composition release can be controlled. Examples of other biodegradable polymers include poly(orthoesters) and poly(anhydrides).

Emulsions

The present disclosure encompasses the recognition that emulsion technologies can provide stabilization benefits to agents of interest, including to large agents as described herein, and specifically including botulinum toxin and/or antibody agents.

Moreover, the present disclosure appreciates that certain liquid nanoemulsion technologies have been demonstrated to provide remarkable transdermal delivery attributes, even for very large molecules, such as botulinum and/or antibody agents. See, e.g., U.S. Patent Publication No. 2012/0328701, U.S. Patent Publication No. 2012/0328702, U.S. Pat. Nos. 8,318,181, and 8,658,391, the disclosures of which are herein incorporated by reference in their entireties. These liquid nanoemulsions are far superior to solid nanoparticle drug delivery, particularly transdermal drug delivery wherein, as noted by Gomaa, the solid nanoparticles cannot penetrate the skin but merely accumulate in the hair follicles These liquid nanoemulsions are also stable for at least 34 months, making them a commercially viable from this perspective as well.

1. Macroemulsions

In some embodiments, the present disclosure provides strategies in which microneedling is used to "condition" skin to which a transdermal product has been, is being, or will be applied. The present disclosure provides an insight that such microneedle conditioning, surprisingly, can provide significant benefit in enhancing transdermal delivery of large agents (e.g., having molecular weights above about 100 KDa or more), notwithstanding prior reports that such strategies are only likely to be useful for small molecular weight agents because studies analyzing transdermal delivery of small molecules (specifically, short, hydrophilic peptides having molecular weights in the range of 400-1000 Da) found "[t]he skin permeation of peptides depends on their molecular weight and decreases as the molecular weight increases." Zhang, S., et al., "Enhanced delivery of hydrophilic peptides in vitro by transdermal microneedle pretreatment." Acta Pharmaceutica Sinica B. 4(1):100-104 (2014).

The present disclosure provides an insight that effective and rapid (i.e., administration over a few minutes) transdermal delivery of large molecules by such liquid macroemulsion compositions can surprisingly be improved by combining macroemulsion administration with microneedle skin conditioning (MSC).

The present disclosure particularly demonstrates that microneedling technologies (e.g., microneedle conditioning of skin) can significantly enhance transdermal delivery of large agents (e.g., botulinum and/or antibody agents), particularly when utilized in conjunction with macroemulsion technologies. Particular macroemulsion compositions of interest include water-in-oil and oil-in water macroemulsions characterized by droplet sizes ranging from greater than about 300 nm to about 5,000 µm in diameter, a ratio of aqueous dispersion media to oil ranging between about 0.01:1 to about 20:1; oil-to-surfactant ratio in the range of between about 0.1 to about 40 and/or zeta potential in the range of between about −80 mV to about +80 mV. The surfactant portion of the composition may contain one or more surfactants.

Macroemulsion Formulation

| Component | Weight (g) | Percent (by weight) |
|---|---|---|
| 1349 oil | 22.0 | 22 |
| Tween-80 | 1.0 | 1 |
| Span-65 | 3.0 | 3 |
| Propylparaben | 0.2 | 0.2 |
| Sodium chloride (a) | 0.63 | 0.63 |
| Sodium phosphate dibasic | 0.04 | 0.04 |
| Gelatin | 0.02 | 0.02 |
| Large Agent (e.g., botulinum toxin and/or antibody) | * | * |
| Isopropyl myristate | 0.62 | 0.62 |
| Purified water (c) | 72.49 | 72.49 |
| Total | 100.22 | 100.00 |

* A person of ordinary skill, in view of the instant specification, could make reasonable adjustments to this and other ingredients depending on the volume, weight, and/or dose of large agent to be utilized.

Macroemulsion formulations may act to stabilize large agents such as botulinum and/or antibody agents. Macroemulsion formulations would not necessarily be expected in and of themselves to achieve transdermal delivery of large agents, nonetheless, the present disclosure encompasses the insight that stabilization improvement that may be provided by incorporation into a macroemulsion composition might, when combined with microneedling technologies as described herein, achieve synergistic enhancement of transdermal delivery.

The present disclosure teaches that, notwithstanding the expectation that MSC is only helpful in facilitating transdermal delivery of small compounds, the transdermal delivery of large agents by macroemulsion compositions can be enabled by combination with microneedle technology. In addition, this disclosure is particularly surprising given that microneedle conditioning in combination with encapsulation of even small molecule agents in solid nanoparticles, as described by Gomaa, provided for small amounts of penetration only after 6 hours of administration, and no material penetration was observed until 24 hours after administration.

In some embodiments, a macroemulsion formulation comprising a large agent is administered in conjunction with microneedle conditioning with solid microneedles. In some embodiments, MSC of a site is performed before applying (e.g., before a particular application and/or before each application of) a macroemulsion formulation comprising a large agent to the site. In some embodiments, MSC of a site is performed after applying a macroemulsion formulation comprising a large agent to the site. In some embodiments, MSC of a site and applying a macroemulsion formulation comprising a large agent to the site occur at substantially the same time. In some embodiments, the macroemulsion formulation comprising a large agent is not injected via one or more microneedles. In some embodiments, a microneedle is part of an array of microneedles. In some embodiments, a microneedle may have a length of between about 1 μm to about 4,000 μm. In some embodiments, a microneedle may have a length of between about 1 μm to about 2,000 μm. In some embodiments, a microneedle may have a length of between about 50 μm to about 400 μm. In some embodiments, a microneedle may have a length of between about 800 μm to about 1500 μm.

Findings presented herein are particularly surprising given reports that transdermal delivery of solid nanoparticles of a size (e.g., 105±2.92 nm) far smaller than that of the droplets in the macroemulsion composition utilized herein do not effectively deliver (or enhance delivery of) even small molecule agents transdermally across skin. For example, Gomaa et al described a study in which a solution of rhodamine dye (molecular weight 479 Da) encapsulated in PLGA nanoparticles was applied to skin that had been preconditioned by microneedling, and skin penetration was assessed. See Gomaa, Y., et al, "Effect of microneedle treatment on the skin permeation of a nanoencapsulated dye." J Pharm Pharmacol. 2012 November; 64(11): 1592-1602. The data showed that very small amounts of dye began to permeate the skin after 6 hours of continuous application; no significant increase in permeation was observed until skin had been treated continuously for 24 hours. The researchers explained that "there is an emerging consensus that NPs [nanoparticles] cannot usually penetrate the stratum corneum, although they may well deposit in hair follicles." Thus, prior to the present disclosure, those skilled in the art would expect that use of microneedling technologies with vehicles significantly larger than 105 nm could not effectively deliver even small molecule agents (e.g., rhodamine dye) transdermally; certainly delivery of large agents would have been considered impossible. The present disclosure, however, demonstrates that microneedling can significantly enhance transdermal delivery of large agents, particularly when utilized in conjunction with macroemulsion technologies.

Among other things, the present disclosure demonstrates that microneedling technologies can enhance transdermal delivery (e.g., of large agents, particularly from macroemulsion compositions), when no other disrupting agent (i.e., no chemical penetration enhancing agent and no other technology that disrupts or punctures skin structure) is utilized. Prior studies of transdermal delivery of an agent as large as botulinum toxin (i.e., about 150 kDa) using microneedles have reported that delivery is unsuccessful unless additional treatment is applied to disrupt skin. For example, U.S. Patent Publication No. 2010/0196445 reports that botulinum toxin is not delivered effectively from pre-coated microneedles unless a skin-digesting enzyme is also applied, so that skin structure is disrupted at the site of microneedling.

The present disclosure demonstrates, among other things, that microneedling technologies can achieve transdermal delivery (e.g., of large agents, particularly from macroemulsion and nanoemulsion compositions), when no coating or loading of the microneedles is utilized and/or when the microneedles are not designed to be left in the skin. Among other things, as already noted, the present disclosure appreciates that such coating or loading of microneedles might not be commercially viable, at least due to the instability of the botulinum coating or loaded material. For example, per Johnson, E., et al., "Botulinum toxin is very susceptible to denaturation due to surface denaturation, heat, and alkaline conditions. Lyophilization or freeze-drying of botulinum toxin is the most economically sound and practical method of distributing the product in a form that is stable and readily used by the clinician." U.S. Pat. No. 5,512,547. Additionally, as will be appreciated by those skilled in the art reading the specification, technologies described herein have certain advantages including that it is not necessary that microneedles be left in or in association with tissue. For example, those skilled in the art will appreciate that leaving the microneedles in the skin can risk skin irritation, inflammation, allergic reaction, and/or cosmetically undesirable scarring. In contrast to the present ention, technologies such as that described in U.S. Patent Publication No. 2017/0209553 utilize a microneedle array that is loaded with botulinum into the needles and is designed for the microneedles to break off into the skin (per U.S. Patent No. 2017/0209553 and 2016/0263362.

The present disclosure provides surprisingly effective technologies for transdermal delivery of large agents (e.g., botulinum toxin, antibodies, etc.). In particular, the present disclosure teaches that transdermal delivery of such agents can be significantly enhanced through use of microneedling technologies without any other disrupting strategy. Provided technologies therefore can achieve effective delivery without inflammation, irritation, and/or allergic reaction that often accompanies use of skin disrupting agents. As will be appreciated by those skilled in the art reading the specification, the present disclosure teaches that transdermal delivery of such large agents can be significantly enhanced through use of microneedling technologies even when the large agent is not loaded into, coated on, and/or fabricated as part of the microneedles. Similarly, as will be appreciated by those skilled in the art reading the specification, the present disclosure teaches that delivery of large agents as described herein can be significantly enhanced through use of microneedling technologies (and specifically through use of MSC), without leaving microneedles in the skin (e.g., by having them break off and/or otherwise be retained and/or degraded in situ). For example, those skilled in the art will appreciate that provided technologies can avoid problems with the long-term stability of the large agent necessary for a commercially viable product, and can achieve effective delivery without inflammation, irritation, and/or allergic reaction that may result from the skin disrupting agents and/or the microneedles being left in the skin. Indeed, in the examples and elsewhere, the present disclosure explicitly teaches that MSC performed with microneedles that contain no botulinum toxin facilitates transdermal delivery of botulinum toxin from a topical (e.g., cream, ointment) composition, and particularly from a composition comprising a macro- or nano-emulsion.

In some embodiments, the present disclosure teaches that particularly advantageous results are achieved when microneedling technologies are combined with macroemulsion compositions. In some embodiments, microneedling technologies are combined with lotion, cream, or liquid compositions, which in turn may be or comprise macroemulsion compositions. In some embodiments, provided technologies do not utilize skin disrupting technologies, such as chemical penetration enhancing agents.

In some embodiments, the present invention utilizes macroemulsion compositions comprising large agents that are particularly effective and/or useful in medical contexts, e.g., for therapeutic purposes. In some embodiments, particular macroemulsion compositions are particularly effective and/or useful for topical administration of agents to a subject in need thereof. In some embodiments macroemulsion compositions may comprise of one or more large agents.

In some embodiments, a macroemulsion may be formulated into a composition suitable for topical administration on the skin. In some embodiments, a composition suitable for topical administration may be a lotion, cream, powder, ointment, liniment, gel, or drops.

In some embodiments, macroemulsion formulations comprise water, medium chain triglyceride, span 65, polysorbate 80, methylparaben, and propylparaben. In some embodiments, macroemulsion formulations comprise water, medium chain triglyceride, span 65, and polysorbate 80.

In some embodiments, provided compositions comprise a mixture of a provided macroemulsion composition and one or more pharmaceutically acceptable excipients. In some embodiments, cream and/or lotion formulations comprise a mixture of a provided macroemulsion composition and/or a saline solution.

In some embodiments, provided compositions comprise macroemulsion compositions comprising one or more large agents. In some embodiments, provided compositions are cream and/or lotion formulations. In some embodiments, provided cream and/or lotion formulations comprise macroemulsion compositions. In some embodiments, compositions comprise provided macroemulsion compositions but are not cream and/or lotion formulations. In some embodiments, suitable compositions are formulated into creams and/or lotions but do not comprise a macroemulsion composition.

In some embodiments, provided compositions comprise a mixture of a provided macroemulsion composition and one or more pharmaceutically acceptable excipients, e.g., for topical and/or transdermal (e.g., by lotions, creams, powders, ointments, liniments, gels, drops, etc.) administration.

2. Nanoemulsions

In some embodiments, the present disclosure provides strategies in which microneedling is used to "condition" skin to which a transdermal product has been, is being, or will be applied. The present disclosure provides an insight that such microneedle conditioning, surprisingly, can provide significant benefit in enhancing transdermal delivery of large agents (e.g., having molecular weights above about 100 KDa or more), notwithstanding prior reports that such strategies are only likely to be useful for small molecular weight agents because studies analyzing transdermal delivery of small molecules (specifically, short, hydrophilic peptides having molecular weights in the range of 400-1000 Da) found "[t]he skin permeation of peptides depends on their molecular weight and decreases as the molecular weight increases." Zhang, S., et al., "Enhanced delivery of hydrophilic peptides in vitro by transdermal microneedle pretreatment." Acta Pharmaceutica Sinica B. 4(1):100-104 (2014).

The present disclosure provides an insight that effective and rapid (i.e., administration over a few minutes) transdermal delivery of large molecules by such liquid nanoemulsion compositions can surprisingly be improved by combining nanoemulsion administration with microneedle skin conditioning (MSC).

The present disclosure particularly demonstrates that microneedling technologies (e.g., microneedle conditioning of skin) can significantly enhance transdermal delivery of large agents (e.g., botulinum and/or antibody agents), particularly when utilized in conjunction with nanoemulsion technologies. Particular nanoemulsion compositions of interest include water-in-oil and oil-in water nanoemulsions characterized by droplet sizes ranging from about 1 nm to about 300 nm in diameter, a ratio of aqueous dispersion media to oil ranging between about 0.01:1 to about 20:1; oil-to-surfactant ratio in the range of between about 0.1 to about 40 and/or zeta potential in the range of between about −80 mV to about +80 mV.

In some embodiments, provided nanoemulsion compositions comprise oil and surfactant at a ratio ranging between about 0.1:1 to about 2:1. In some embodiments, provided nanoemulsion compositions comprise oil and surfactant at a ratio of about 0.1:1 to about 1:1. In some embodiments, provided nanoemulsion compositions comprise oil and surfactant at a ratio of about 0.5:1 to about 1:1. In some embodiments, provided nanoemulsion compositions comprise oil and surfactant at a ratio of about 0.5:1 to about 1:1.5. In some embodiments, provided nanoemulsion compositions comprise oil and surfactant at a ratio of about 0.1:1, about 0.15:1, about 0.2:1, about 0.25:1, about 0.3:1, about 0.35:1, about 0.4:1, about 0.45:1, about 0.5:1, about 0.5:1, about 0.55:1, about 0.6:1, about 0.65:1, about 0.7:1, about 0.75:1, about 0.8:1, about 0.85:1, about 0.9:1, about 0.95:1, or about 1:1 In some embodiments, provided nanoemulsion compositions comprise oil and surfactant at a ratio of about 0.67:1.

In some embodiments, the aqueous dispersion medium (e.g., water, buffer, salt solution, etc.) and surfactant are utilized at a ratio ranging between 0.01 and 20. In some embodiments, the aqueous dispersion medium (e.g., water, buffer, salt solution, etc.) and surfactant are utilized at a ratio ranging between 0.1 and 20. In some embodiments, the aqueous dispersion medium (e.g., water, buffer, salt solution, etc.) and surfactant are utilized at a ratio ranging between 0.5 and 10. In some embodiments, the aqueous dispersion medium (e.g., water, buffer, salt solution, etc.) and surfactant are utilized at a ratio ranging between 0.5 and 1. In some embodiments, the ratio of aqueous dispersion medium (e.g., water, buffer, salt solution, etc.) to surfactant is approximately 0.01:1, approximately 0.02:1, approximately 0.03:1, approximately 0.04:1, approximately 0.05:1, approximately 0.06:1, approximately 0.07:1, approximately 0.08:1, approximately 0.0:1, approximately 0.1:1, approximately 0.2:1, approximately 0.3:1, approximately 0.4:1, approximately 0.5:1, approximately 1:1, approximately 2:1, approximately 3:1, approximately 4:1, approximately 5:1, approximately 6:1, approximately 7:1, approximately 8:1, approximately 9:1 or approximately 10:1. In some embodiments, the ratio of surfactant to water is approximately 0.5:1, approximately 1:1, approximately 2:1, approximately 3:1, approximately 4:1, approximately 5:1, approximately 6:1, approximately 7:1, approximately 8:1, approximately 9:1, approximately 10:1, approximately 11:1, approximately 12:1, approximately 13:1, approximately 14:1, approximately 15:1, approximately 16:1, approximately 17:1, approximately 18:1, approximately 19:1, or approximately 20:1. In some embodiments, aqueous dispersion medium (e.g., water, buffer, salt solution, etc.) and surfactant are utilized at a ratio ranging between 0.5 and 2. In some embodiments, the ratio of aqueous dispersion medium (e.g., water, buffer, salt solution, etc.) to surfactant is approximately 0.5:1, approximately 1:1, or approximately 2:1. In some embodiments, the ratio of surfactant to aqueous dispersion medium (e.g., water, buffer, salt solution, etc.) is approximately 0.5:1, approximately 1:1, or approximately 2:1. In some embodiments, the ratio of aqueous dispersion medium (e.g., water, buffer, salt solution, etc.) to surfactant is approximately 1:1. In some embodiments, compositions utilizing such ratios of aqueous dispersion medium (e.g., water, buffer, salt solution, etc.) to surfactant comprise water-in-oil emulsions.

In some embodiments, droplets within nanoemulsion compositions have diameters (e.g., average and/or median diameters) within a range of about 10 nm to about 300 nm, about 10 nm to about 200 nm, about 10 nm to about 150 nm, about 10 nm to about 130 nm, about 10 nm to about 120 nm, about 10 nm to about 115 nm, about 10 nm to about 110 nm, about 10 nm to about 100 nm, or about 10 nm to about 90 nm. In some embodiments, droplets within nanoemulsion compositions have diameters (e.g., average and/or median diameters) within a range of 1 nm to 300 nm, 1 nm to 200 nm, 1 nm to 150 nm, 1 nm to 120 nm, 1 nm to 100 nm, 1 nm to 75 nm, 1 nm to 50 nm, or 1 nm to 25 nm. In some embodiments, droplets within nanoemulsion compositions have diameters (e.g., average and/or median diameters) of 1 nm to 15 nm, 15 nm to 200 nm, 25 nm to 200 nm, 50 nm to 200 nm, or 75 nm to 200 nm.

In some embodiments, a total droplet distribution is encompassed within a specified range of droplet diameter size. In some embodiments, less than 50%, 25%, 10%, 5%, or 1% of a total droplet distribution is outside of a specified range of droplet diameter sizes. In some embodiments, less than 1% of a total droplet distribution is outside of a specified range of droplet diameter sizes. In some embodiments, a nanoemulsion composition is substantially free of droplets having a diameter larger than 300 nm, 250 nm, 200 nm, 150 nm, 120 nm, 100 nm, 75 nm, 50 nm, or 25 nm. In some embodiments, less than 50%, 25%, 10%, 5%, or 1% of a total droplet distribution have diameters larger than 300 nm, 250 nm, 200 nm, 150 nm, 120 nm, 100 nm, 75 nm, 50 nm, or 25 nm.

In some embodiments, droplets within nanoemulsion compositions have an average droplet size that is under about 300 nm, about 250 nm, about 200 nm, about 150 nm, about 130 nm, about 120 nm, about 115 nm, about 110 nm, about 100 nm, about 90 nm, or about 50 nm. In some embodiments, average droplet size is within a range of about 10 nm and about 300 nm, about 50 nm and about 250, about 60 nm and about 200 nm, about 65 nm and about 150 nm, or about 70 nm and about 130 nm. In some embodiments, average droplet size is about 80 nm and about 110 nm. In some embodiments, average droplet size is about 90 nm and about 100 nm.

In some embodiments, nanoemulsion droplets have a zeta potential ranging between −80 mV and +80 mV. In some embodiments, nanoemulsion droplets have a zeta potential ranging between −50 mV and +50 mV. In some embodiments, nanoemulsion droplets have a zeta potential ranging between −25 mV and +25 mV. In some embodiments, nanoemulsion droplets have a zeta potential ranging between n −10 mV and +10 mV. In some embodiments, nanoemulsion droplets have a zeta potential of about −80 mV, about −70 mV, about −60 mV, about 50 mV, about −40 mV, about −30 mV, about −25 mV, about −20 mV, about −15 mV, about −10 mV, or about −5 mV. In some embodiments, nanoemulsion droplets have a zeta potential of about +50 mV, about +40 mV, about +30 mV, about +25 mV, about +20 mV, about +15 mV, about +10 mV, or about +5 mV. In some embodiments, nanoemulsion droplets have a zeta potential that is about 0 mV.

The present disclosure provides surprisingly effective technologies for transdermal delivery of large agents (e.g., botulinum toxin, antibodies, etc.). In particular, the present disclosure teaches that transdermal delivery of such agents can be significantly enhanced through use of microneedling technologies without any other disrupting strategy. Provided technologies therefore can achieve effective delivery without inflammation, irritation, and/or allergic reaction that often accompanies use of skin disrupting agents. As will be appreciated by those skilled in the art reading the specification, the present disclosure teaches that transdermal delivery of such large agents can be significantly enhanced through use of microneedling technologies even when the large agent is not loaded into, coated on, and/or fabricated as part of the microneedles. Similarly, as will be appreciated by those skilled in the art reading the specification, the present disclosure teaches that delivery of large agents as described herein can be significantly enhanced through use of microneedling technologies (and specifically through use of MSC), without leaving microneedles in the skin (e.g., by having them break off and/or otherwise be retained and/or degraded in situ). For example, those skilled in the art will appreciate that provided technologies can avoid problems with the long-term stability of the large agent necessary for a commercially viable product, and can achieve effective delivery without inflammation, irritation, and/or allergic reaction that may result from the skin disrupting agents and/or the microneedles being left in the skin. Indeed, in the examples and elsewhere, the present disclosure explicitly teaches that MSC performed with microneedles that contain no botulinum toxin facilitates transdermal delivery of botulinum toxin from a topical (e.g., cream, ointment) composition, and particularly from a composition comprising a macro and nano-emulsion.

In some embodiments, the present disclosure teaches that particularly advantageous results are achieved when microneedling technologies are combined with nanoemulsion compositions. In some embodiments, microneedling technologies are combined with lotion, cream, or liquid compositions, which in turn may be or comprise nanoemulsion compositions. In some embodiments, provided technologies do not utilize skin disrupting technologies, such as chemical penetration enhancing agents.

Findings presented herein are particularly surprising given reports that transdermal delivery of solid nanoparticles of a size (e.g., 105±2.92 nm) comparable to that of the liquid droplets in the nanoemulsion composition utilized herein do not effectively deliver (or enhance delivery of) even small molecule agents transdermally across skin. For example, Gomaa et al described a study in which a solution of rhodamine dye (molecular weight 479 Da) encapsulated in PLGA nanoparticles was applied to skin that had been preconditioned by microneedling, and skin penetration was assessed. See Gomaa, Y., et al, "Effect of microneedle treatment on the skin permeation of a nanoencapsulated dye." J Pharm Pharmacol. 2012 November; 64(11): 1592-1602. The data showed that very small amounts of dye began to permeate the skin after 6 hours of continuous application; no significant increase in permeation was observed until skin had been treated continuously for 24 hours. The researchers explained that "there is an emerging consensus that NPs [nanoparticles] cannot usually penetrate the stratum corneum, although they may well deposit in hair follicles." Thus, prior to the present disclosure, those skilled in the art would expect that use of microneedling technologies with nano-sized vehicles could not effectively deliver even small molecule agents (e.g., rhodamine dye) transdermally; certainly delivery of large agents would have been considered impossible. The present disclosure, however, demonstrates that microneedling can significantly enhance transdermal delivery of large agents, particularly when utilized in conjunction with a nanoemulsion system.

Among other things, the present disclosure demonstrates that microneedling technologies can enhance transdermal delivery (e.g., of large agents, particularly from nanoemulsion compositions), when no other disrupting agent (i.e., no chemical penetration enhancing agent and no other technology that disrupts or punctures skin structure) is utilized. Prior studies of transdermal delivery of an agent as large as botulinum toxin (i.e., about 150 kDa) using microneedles have reported that delivery is unsuccessful unless additional treatment is applied to disrupt skin. For example, U.S. Patent Publication No. 2010/0196445 reports that botulinum toxin is not delivered effectively from pre-coated microneedles unless a skin-digesting enzyme is also applied, so that skin structure is disrupted at the site of microneedling.

The present disclosure demonstrates, among other things, that microneedling technologies can achieve transdermal delivery (e.g., of large agents, particularly from macroemulsion and nanoemulsion compositions), when no coating or loading of the microneedles is utilized and/or when the microneedles are not designed to be left in the skin. Among other things, as already noted, the present disclosure appreciates that such coating or loading of microneedles might not be commercially viable, at least due to the instability of the botulinum coating or loaded material. For example, per Johnson, E., et al., "Botulinum toxin is very susceptible to denaturation due to surface denaturation, heat, and alkaline conditions, Lyophilization or freeze-drying of botulinum toxin is the most economically sound and practical method of distributing the product in a form that is stable and readily used by the clinician." U.S. Pat. No. 5,512,547. Additionally, as will be appreciated by those skilled in the art reading the specification, technologies described herein have certain advantages including that it is not necessary that microneedles be left in or in association with tissue. For example, those skilled in the art will appreciate that leaving the microneedles in the skin can risk skin irritation, inflammation, allergic reaction, and/or cosmetically undesirable scarring. In contrast to the present invention, technologies such as that described in U.S. Patent No. 2017/0209553 utilize a microneedle array that is loaded with botulinum into the needles and is designed for the microneedles to break off into the skin (per U.S. Patent No. 2017/0209553 and 2016/0263362).

The present disclosure teaches that, notwithstanding the expectation that MSC is only helpful in facilitating transdermal delivery of small compounds, the already highly effective transdermal delivery of large agents by nanoemulsion compositions can be dramatically enhanced by combination with microneedle technology. In addition, this disclosure is particularly surprising given that microneedle conditioning in combination with encapsulation of even small molecule agents in solid nanoparticles, as described by Gomaa, provided for small amounts of penetration only after 6 hours of administration, and no material penetration was observed until 24 hours after administration.

In some embodiments, a nanoemulsion formulation comprising a large agent is administered in conjunction with microneedle conditioning with solid microneedles. In some embodiments, MSC of a site is performed before applying (e.g., before a particular application and/or before each application of) a nanoemulsion formulation comprising a large agent to the site. In some embodiments, MSC of a site is performed after applying a nanoemulsion formulation comprising a large agent to the site. In some embodiments, MSC of a site and applying a nanoemulsion formulation comprising a large agent to the site occur at substantially the same time. In some embodiments, the macroemulsion formulation comprising a large agent is not injected via one or more microneedles. In some embodiments, a microneedle is part of an array of microneedles. In some embodiments, a microneedle may have a length of between about 1 μm to about 4,000 μm. In some embodiments, a microneedle may have a length of between about 1 μm to about 2,000 μm. In some embodiments, a microneedle may have a length of between about 50 μm to about 400 μm. In some embodiments, a microneedle may have a length of between about 800 μm to about 1500 μm.

In some embodiments, the present invention utilizes nanoemulsion compositions comprising large agents that are particularly effective and/or useful in medical contexts, e.g., for therapeutic purposes. In some embodiments, particular nanoemulsion compositions are particularly effective and/or useful for topical administration of agents to a subject in need thereof. In some embodiments nanoemulsion compositions may comprise of one or more large agents. Exemplary nanoemulsion composition and methods of making are described in e.g., WO2012/103035, the disclosure of which is incorporated by reference in its entirety.

In some embodiments, a nanoemulsion may be formulated into a composition suitable for topical administration. In some embodiments, a composition suitable for topical administration may be a lotion, cream, powder, ointment, liniment, gel, or drops.

In some embodiments, nanoemulsion formulations comprise water, medium chain triglyceride, polysorbate 80, methylparaben, and propylparaben. In some embodiments, nanoemulsion formulations comprise water, medium chain triglyceride, and polysorbate 80. An exemplary premix, not meant to be limiting, is provided in Table 2.

TABLE 2

Exemplary Premix

| % w/w | Ingredient |
| --- | --- |
| 6.375 | 1349 Oil |
| 9.562 | Polysorbate 80 |
| 0.199 | Propylparaben |
| 63.75 | Isotonic Sodium Chloride Solution |
| 0.199 | Methylparaben |
| 19.92 | Buffer Solution* |
| ** | Large Agent |
| 100 | TOTAL |

*Buffer Solution contains (w/w) 0.199% gelatin, 0.398% sodium phosphate dibasic, 99.4% purified water, pH adjusted to 6.0 ± 0.2 with hydrochloric acid.
** A person of ordinary skill, in view of the instant specification, could make reasonable adjustments to this and other ingredients depending on the volume, weight, and/or dose of large agent to be utilized.

These compositions are particularly useful in that they can be used for delivery of agents to a subject in need thereof via topical and/or transdermal (e.g., by lotions, creams, powders, ointments, liniments, gels, drops, etc.) administration. In some embodiments, provided cream and/or lotion formulations may be administered to a subject in need thereof via topical and/or transdermal (e.g., by lotions, creams, powders, ointments, liniments, gels, drops, etc.) administration. In some embodiments, provided nanoemulsion compositions may be formulated into cream and/or lotion formulations. In some embodiments, provided cream and/or lotion formulations comprising nanoemulsion compositions may be useful and/or effective for topical administration to a subject. In some embodiments, provided nanoemulsion compositions may be admixed with one or more cream components in a cream formulation (e.g., a provided cream formulation) and/or a saline solution for preparation of a pharmaceutical composition.

The present invention encompasses the recognition that emulsion compositions (e.g., macroemulsion compositions and nanoemulsion compositions) may be formulated into cream and/or lotion formulations for administration to a subject. The present invention encompasses the recognition that provided cream and/or lotion formulations can be particularly useful for formulating emulsions, such as those described herein, for administration to a subject. An exemplary nanoemulsion formulation, not meant to be limiting, is provided in Table 3.

TABLE 3

Nanoemulsion Formulation

| Component | Weight (g) | Percent (by weight) |
| --- | --- | --- |
| 1349 oil | 3.2 | 3.19 |
| Tween-80 | 4.8 | 4.79 |
| Methylparaben | 0.2 | 0.2 |
| Propylparaben | 0.2 | 0.2 |
| Sodium chloride (a) | 0.63 | 0.63 |
| Sodium phosphate dibasic | 0.04 | 0.04 |
| Gelatin | 0.02 | 0.02 |
| Large Agent (e.g., botulinum toxin and/or antibody) | * | * |
| Mineral oil | 0.63 | 0.63 |
| Isopropyl myristate | 0.62 | 0.62 |
| White petrolatum | 0.25 | 0.25 |
| Emulsifying wax | 1.87 | 1.87 |
| Purified water (c) | 87.76 | 87.57 |
| Total | 100.22 | 100.00 |

* A person of ordinary skill, in view of the instant specification, could make reasonable adjustments to this and other ingredients depending on the volume, weight, and/or dose of large agent to be utilized.

In some embodiments, provided compositions comprise a mixture of a provided nanoemulsion composition and one or more pharmaceutically acceptable excipients. In some embodiments, cream and/or lotion formulations comprise a mixture of a provided nanoemulsion composition and/or a saline solution.

In some embodiments, provided compositions comprise provided nanoemulsion compositions. In some embodiments, provided compositions are cream and/or lotion formulations. In some embodiments, provided cream and/or lotion formulations comprise nanoemulsion compositions. In some embodiments, compositions comprise provided nanoemulsion compositions but are not cream and/or lotion formulations. In some embodiments, suitable compositions are formulated into creams and/or lotions but do not comprise a nanoemulsion composition.

In some embodiments, provided compositions comprise a mixture of a provided nanoemulsion composition and one or more pharmaceutically acceptable excipients, e.g., for topical and/or transdermal (e.g., by lotions, creams, powders, ointments, liniments, gels, drops, etc.) administration.

In some embodiments, for nanoemulsion compositions comprising a known therapeutic agent and/or independently active biologically active agent, such nanoemulsion compositions are arranged and constructed and administered in combination with MSC such that an amount of therapeutic agent is delivered to a desired target site (e.g., to epidermal and/or dermal structures) that is sufficient to treat a condition or disorder. In some embodiments, provided nanoemulsion compositions are arranged and constructed (e.g., through selection and/or combination of agents, structure of composition, etc.) such that they achieve a desired therapeutic effect upon administration to the skin. In some embodiments, provided nanoemulsion compositions are arranged and constructed such that they do not induce unwanted clinical effects inside and/or outside of a desired site of action (e.g., surface of skin, dermis, etc.). In some embodiments, provided nanoemulsion compositions are arranged and constructed and administered in combination with MSC such that they have systemic effects.

In some embodiments, provided compositions may be formulated and delivered in combination with MSC so that systemic delivery is achieved; in some embodiments, provided compositions may be formulated and/or delivered so that local, but not systemic, delivery is achieved.

The present disclosure specifically demonstrates effective and efficient delivery of a therapeutic agent (and, in particular, a large biologic agent, such as botulinum toxin or antibody agent) to the dermis using provided compositions in combination with MSC. For example, in some embodiments, the present invention provides methods comprising administration of a composition as described herein without clinically significant side effects. To give but one example, when topical delivery is contemplated, clinically significant side effects include, but are not limited to, unwanted systemic side effects, damage to nervous tissue underlying the dermis (e.g., neuronal paralysis), unwanted effects on muscles (e.g., muscle paralysis), and/or undesirable blood levels of therapeutic agent, etc. An exemplary formulation of a botulinum nanoemulsion premix, not meant to be limiting, is provided in Table 4.

TABLE 4

Botulinum Nanoemulsion Recipe (Premix)

| % w/w | Amount per 400-gram Batch | Ingredient |
|---|---|---|
| 6.375 | 25.50 | 1349 Oil |
| 9.562 | 38.248 | Polysorbate 80 |
| 0.200 | 0.800 (800 mg) | Propylparaben |
| 63.663 | 254.652 | Isotonic Sodium Chloride Solution |
| 0.20 | 0.800 (800 mg) | Methylparaben |
| 19.21 | 76.84 | GPB Buffer Solution |
| 0.79 | 3.16 | Botulinum toxin diluted in Buffer Solution |
| 100 | 400 | TOTAL THEORETICAL WEIGHT |

* Buffer Solution contains (w/w) 0.199% gelatin, 0.398% sodium phosphate dibasic, 99.4% purified water, pH adjusted to 6.0 ± 0.2 with hydrochloric acid.

Diseases, Disorders, and Conditions

The present invention provides technologies for treating and/or preventing any of a variety of systemic or dermatologic diseases, disorders, and/or conditions. In some embodiments, the present invention provides technologies for treating and/or preventing diseases, disorders, or conditions associated with activity of sweat and/or sebaceous glands. In some embodiments, the present invention provides technologies for treating and/or preventing diseases, disorders, or conditions associated with infection. In some embodiments, the present invention provides technologies for treating and/or preventing diseases, disorders, or conditions associated with inflammation. In some embodiments, the present invention provides technologies for the treating and/or preventing diseases, disorders, or conditions associated with inflammation. In some embodiments, the present invention provides technologies for treating and/or preventing diseases, disorders, or conditions associated with cancer. In some embodiments, the present invention provides technologies for treating and/or preventing diseases, disorders, or conditions which are systemic. In some embodiments, the present invention provides technologies for treating and/or preventing diseases, disorders, or conditions which are autoimmune. In some embodiments, the present invention provides technologies for treating and/or preventing diseases, disorders or conditions associated with the epidermal and/or dermal level of the skin.

In some embodiments, the present invention provides technologies for treating and/or preventing one or more of acne, unwanted sweating, body odor, hyperhidrosis, bromhidrosis, chromhidrosis, rosacea, hair loss, psoriasis, actinic keratosis, eczematous dermatitis (e.g., atopic dermatitis, etc.), excess sebum-producing disorders (e.g., seborrhea, seborrheic dermatitis, etc.), burns, Raynaud's phenomenon, lupus erythematosus, hyperpigmentation disorders (e.g., melasma, etc.), hypopigmentation disorders (e.g., vitiligo, etc.), skin cancer (e.g., squamous cell skin carcinoma, basal cell skin carcinoma, etc.), dermal infection (e.g., bacterial infection, viral infection, fungal infection, etc.), facial wrinkles, (e.g., wrinkles involving the forehead, glabellar, rhytids and/or periorbital regions), headache, unsightly facial expressions (e.g., due to overactivity of underlying facial musculature), neck lines, hyperfunctional facial lines, hyperkinetic facial lines, platysma bands, neuromuscular disorders and conditions involving muscular spasm and/or contracture (including various forms of facial palsy, cerebral palsy, blepharospasm, facial contracture), dystonia, prostate hyperplasia, headache, strabismus, hemifacial spasm, tremor, spasticity such as that resulting from multiple sclerosis, retroorbital muscle, various ophthalmologic and urologic conditions (e.g., penile and/or bladder disorders), and/or combinations thereof.

In some embodiments, the present invention provides technologies for treating and/or preventing rheumatoid arthritis. In some embodiments, the present invention provides technologies for treating and/or preventing psoriatic arthritis. In some embodiments, the present invention provides technologies for treating and/or preventing osteoarthritis.

In some embodiments, the present invention provides technologies for treating and/or preventing lupus erythematosus. In some embodiments, the lupus erythematosus is systemic, discoid, drug-induced, or neonatal.

In some embodiments, the present invention provides technologies for treating and/or preventing Crohn's disease. In some embodiments, the present invention provides technologies for treating and/or preventing inflammatory bowel disease. In some embodiments, the present invention provides technologies for treating and/or preventing ulcerative colitis.

In some embodiments, the present invention provides technologies for treating and/or preventing pulmonary disorders. In some embodiments, the pulmonary disorder may be asthma or chronic obstructive pulmonary disorder.

In some embodiments, the present invention provides technologies for treating and/or preventing amyloidosis. In some embodiments the amyloidosis is systemic or cutaneous.

In some embodiments, the present invention provides technologies for treating and/or preventing cancer. In some embodiments the cancer is of the skin, blood, breast, colon, or lung.

In some embodiments, the present invention provides technologies for treating and/or preventing dyslipidemia. In some embodiments the dyslipidemia is hypercholesterolemia.

In some embodiments, the present invention provides technologies for treating and/or preventing infection. In some embodiments, the infection is or is caused by *C. difficile* or *Staphylococcus*.

In some embodiments, the present invention provides technologies for treating and/or preventing pain. In some embodiments the pain is associated with arthritis. In some embodiments the arthritis is rheumatoid arthritis, psoriatic arthritis, or osteoarthritis.

In some embodiments, the present invention provides technologies for treating and/or preventing neurologic conditions. In some embodiments the neurological condition is Alzheimer's Disease, Parkinson's Disease, or stroke.

In some embodiments, the present invention involves administration of at least one provided composition, administered in combination with MSC, according to a dosing regimen sufficient to achieve a reduction in the degree and/or prevalence of a relevant dermatologic condition of at least about 20%; in some embodiments according to a dosing regimen sufficient to achieve a of at least about 25%; in some embodiments according to a dosing regimen sufficient to achieve a reduction of at least about 30%; in some embodiments according to a dosing regimen sufficient to achieve a reduction of at least about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, or more.

In some embodiments, the present invention involves administration of at least one provided composition, administered in combination with MSC, according to a dosing regimen sufficient to achieve a reduction in the degree and/or prevalence of a relevant dermatologic condition of at least about 20% in a specified percentage of a population of patients to which the composition was administered; in some embodiments according to a dosing regimen sufficient to achieve a of at least about 25% in a specified percentage of a population of patients to which the composition was administered; in some embodiments according to a dosing regimen sufficient to achieve a reduction of at least about 30% in a specified percentage of a population of patients to which the composition was administered; in some embodiments according to a dosing regimen sufficient to achieve a reduction of at least about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90% or more in a specified percentage of a population of patients to which the composition was administered. In some embodiments, the specified percentage of population of patients to which the composition was administered is at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. To give but a few illustrative examples, in some embodiments, the present invention involves administration of at least one provided composition according to a dosing regimen sufficient to achieve a reduction in the degree and/or prevalence of a relevant dermatologic condition of at least about 20% in at least about 50% of the population of patients to which the composition was administered. In some embodiments, the present invention involves administration of at least one provided composition according to a dosing regimen sufficient to achieve a reduction in the degree and/or prevalence of a relevant dermatologic condition of at least about 30% in at least about 50% of the population of patients to which the composition was administered.

The present invention provides technologies for treating and/or preventing a dermatologic condition comprising administration of a provided composition in combination with MSC to a subject suffering from, susceptible to, and/or displaying symptoms of the dermatologic condition. In some embodiments, provided compositions for treatment of a dermatologic condition as described herein are formulated for any route of administration described herein. In some embodiments, provided compositions are formulated for topical administration. In some embodiments, provided compositions are formulated into a cream, liniment, lotion, gel, shampoo, conditioner, sunscreen, deodorant, and/or antiperspirant (e.g., as a roll-on, solid stick, gel, cream, aerosol, etc.), etc., as appropriate to the condition being treated.

In some embodiments, such a provided composition is administered locally in combination with MSC to an affected site (e.g., axillae, hands, feet, scalp, hair follicle, face, neck, back, arms, chest, legs, groin, crotch, etc., as appropriate to a particular condition being treated). In some embodiments, local administration is achieved by topical administration in combination with MSC.

Compositions and Formulations

As noted herein, the present invention provides and/or utilizes compositions comprising one or more large agents for administration in combination with MSC. In some embodiments, provided compositions may be formulated for topical and/or transdermal delivery (e.g., as lotions, creams, liniments, ointments, powders, gels, drops, etc.). In some embodiments, provided compositions may be or include a nanoemulsion. In some embodiments, provided compositions may be or include a macroemulsion.

Formulations of provided compositions may be prepared by any appropriate method, for example as known or hereafter developed in the art of pharmacology. In general, such preparatory methods include a step of bringing an provided composition into association with one or more excipients, and then, if necessary and/or desirable, shaping and/or packaging into an appropriate form for administration, for example as or in a single- or multi-dose unit.

In some embodiments, compositions may be prepared, packaged, and/or sold in bulk, as a single unit dose, and/or as a plurality of single unit doses. As used herein, a "unit dose" is a discrete amount of a pharmaceutical composition comprising a predetermined amount of the provided composition. The amount of a provided composition is generally equal to the dosage of the provided composition which would be administered to a subject and/or a convenient fraction of such a dosage such as, for example, one-half or one-third of such a dosage.

In some embodiments, appropriate excipients for use in compositions (e.g., pharmaceutically and/or cosmetically acceptable compositions) may, for example, include one or more excipients such as solvents, dispersion media, granulating media, diluents, or other liquid vehicles, dispersion or suspension aids, surface active agents and/or emulsifiers, isotonic agents, thickening or emulsifying agents, preservatives, solid binders, lubricants, disintegrating agents, binding agents, preservatives, buffering agents and the like, as suited to the particular dosage form desired. In some embodiments, excipients such as cocoa butter and/or suppository waxes, coloring agents, coating agents, sweetening, flavoring, and/or perfuming agents can be utilized. Remington's *The Science and Practice of Pharmacy*, 21$^{st}$ Edition, A.

R. Gennaro (Lippincott, Williams & Wilkins, Baltimore, Md., 2005; incorporated herein by reference) discloses various excipients used in formulating pharmaceutical compositions and known techniques for the preparation thereof.

In some embodiments, an appropriate excipient (e.g., a pharmaceutically and/or cosmetically acceptable excipient) is at least 95%, at least 96%, at least 97%, at least 98%, at least 99%, or 100% pure. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or other International Pharmacopoeia.

In some embodiments, provided compositions are formulated as a cream, liniment, ointment, oil, foam, spray, lotion, liquid, powder, thickening lotion, or gel (e.g., formulated for transdermal delivery as described herein). Particular exemplary such formulations may be prepared, for example, as cosmetic formulation products such as skin softeners, nutritional lotion type emulsions, cleansing lotions, cleansing creams, skin milks, emollient lotions, massage creams, emollient creams, make-up bases, facial packs or facial gels, cleaner formulations such as shampoos, rinses, body cleansers, hair-tonics, or soaps, or dermatological compositions such as lotions, ointments, gels, creams, liniments, patches, deodorants, or sprays. In some embodiments, compositions for topical administration are not formulated for administration to mucous membranes (e.g., are inappropriate for application to mucous membranes and/or are not formulated to deliver an appropriate amount of large agent to or across mucous membranes).

Treatment Sites

The technologies of the invention are suitable for both human and veterinary use. Subjects suffering from any disorder which would benefit from topical application of an active agent may be treated with the disclosed technologies for transdermal drug delivery.

Any site suitable site for MSC is a suitable administration site. In some embodiments, an administration site is the skin overlying a muscle or muscle group of a subject. In some embodiments, the site is hairless. In some embodiments, the site is on the torso. In some embodiment the site is on the back. In some embodiments the site is on the chest. In some embodiments, the site is on the buttocks. In some embodiments, the site is on the crotch. In some embodiments, the site is on the groin. In some embodiments, the site is on the head. In some embodiments the site is on the scalp. In some embodiments, the site is on the face. In some embodiments the site is on the neck. In some embodiments the site is on the décolleté. In some embodiments, the site is in the armpit. In some embodiments, the site is on the axillae. In some embodiments the site is on the hands. In some embodiments the site is on the feet. In some embodiments the site is on the arms. In some embodiments the site is on the legs. In some embodiments, the site is not a mucous membrane.

In some embodiments the site is affected by a dermatologic condition. In some embodiments the site is the skin overlying a muscle or muscle group affected by a neuromuscular condition. In some embodiments, the length of the microneedles used in MSC is adjusted based on skin thickness of the treatment site.

In some embodiments, MSC comprises one impression of MN or MN array. In some embodiments, MSC comprises two impressions of MN or MN array. In some embodiments, MSC comprises three impressions of MN or MN array. In some embodiments, MSC comprises four impressions of MN or MN array. In some embodiments, MSC comprises five impressions of MN or MN array. In some embodiments, MSC comprises six impressions of MN or MN array. In some embodiments, MSC comprises seven impressions of MN or MN array. In some embodiments, MSC comprises eight impressions of MN or MN array. In some embodiments, MSC comprises nine impressions of MN or MN array. In some embodiments, MSC comprises ten impressions of MN or MN array. In some embodiments, MSC comprises eleven impressions of MN or MN array. In some embodiments, MSC comprises twelve impressions of MN or MN array. In some embodiments, MSC comprises thirteen impressions of MN or MN array. In some embodiments, MSC comprises fourteen impressions of MN or MN array. In some embodiments, MSC comprises fifteen impressions of MN or MN array. In some embodiments, MSC comprises sixteen impressions of MN or MN array. In some embodiments, MSC comprises seventeen impressions of MN or MN array. In some embodiments, MSC comprises eighteen impressions of MN or MN array. In some embodiments, MSC comprises nineteen impressions of MN or MN array. In some embodiments, MSC comprises twenty impressions of MN or MN array. In some embodiments, the MSC comprises rolling the MN or MN array over the skin one or more times. In some embodiments, an MN array is rotated between impressions. In some embodiments an MN array is not rotated between impressions. In some embodiments impressions are made on the same site. In some embodiments impressions are made on overlapping sites. In some embodiments, impressions are made on different sites. In some embodiments, impressions are made by stamping of a MN array. In some embodiments, impressions are made by rolling a microneedle roller over a site one or more times. In accordance with established MN practices, in some embodiments, the MN array skin impressions last under one second or, alternatively, in some embodiments, they last over one second and may, for example, last for 30 seconds or more, 60 seconds or more, two minutes or more, five minutes or more, ten minutes or more, thirty minutes or more, etc.

Administration

The present invention provides technologies for delivering emulsion compositions (e.g., botulinum emulsion compositions or antibody agent emulsion compositions) for various applications including, for example, cosmetic, nutraceutical, and medical applications. Such emulsion compositions may include one or more biologically active agents. In some embodiments, emulsion compositions include botulinum toxin. In some embodiments, emulsion compositions include antibody agents. In some embodiments the emulsion compositions are nanoemulsion compositions and/or macroemulsion compositions.

The present invention provides technologies for treating conditions or disorders using any of the provided compositions (e.g., provided emulsion compositions; cream and/or lotion formulations; combination of provided emulsion compositions and cream and/or lotion formulation; etc.) as described herein in combination with MSC.

In some embodiments, such methods involve administration of a provided composition in combination with MSC to a patient suffering from and/or susceptible to a disease, condition, or disorder. In some embodiments, such methods involve administration of a provided nanoemulsion composition in combination with MSC to a patient suffering from and/or susceptible to a disease, condition, or disorder associated with the dermal layer of the skin. In some embodiments, such methods involve administration of an emulsion composition in combination with MSC comprising at least one known therapeutic agent and/or independently active biologically active agent to a patient suffering from and/or susceptible to a disease, condition, or disorder. In some embodiments, such methods involve administration of an emulsion composition and/or at least one known therapeutic agent and/or independently active biologically active agent formulated with a provided cream and/or lotion formulation in combination with MSC to a patient suffering from and/or susceptible to a disease, condition, or disorder. In some embodiments, such methods involve administration of compositions via topical and/or transdermal (e.g., by lotions, creams, powders, ointments, liniments, gels, drops, etc.) administration in combination with MSC. Some embodiments further include administration of a penetration enhancing agent. Some embodiments further include administration of a non-irritating penetration enhancing agent.

In some embodiments, the present invention provides technologies for treating any conditions or disorders. In some embodiments, the present invention demonstrates that certain compositions as described herein in combination with MSC can achieve controlled delivery of active agents efficiently and specifically to biologically relevant target sites (e.g., particular tissues, locations within the skin, cells, etc.). In some embodiments, the present invention demonstrates controlled delivery and/or achievement of therapeutic effect in a certain biologically relevant target site without significant side effects associated with delivery to other areas.

In some embodiments, the present invention provides technologies for treating conditions or disorders associated with epidermal and/or dermal structures (e.g., sweat glands, sebaceous glands, hair follicles, etc.). In some embodiments, the present invention demonstrates that provided compositions as described herein (e.g., provided nanoemulsion composition; cream and/or lotion formulation; combination of provided nanoemulsion composition and cream and/or lotion formulation; etc.) in combination with MSC can deliver active agents efficiently and specifically to the dermis, and that provided compositions as described herein can have therapeutic effects upon administration to the skin of a subject. In some embodiments, the present invention demonstrates dermal delivery and/or achievement of therapeutic effect without significant side effects associated with delivery to other areas (e.g., to subdermal or extradermal structures and/or to tissues other than dermis). In some embodiments, provided compositions as described herein (e.g., provided emulsion compositions; cream and/or lotion formulations; combination of provided emulsion compositions and cream and/or lotion formulations; etc.) in combination with MSC can transdermally deliver active agents, such as therapeutic agents (e.g., botulinum toxins, antibody agents, etc.).

The present invention provides technologies for treating conditions or disorders by administering to a patient a provided composition as described herein (e.g., a provided emulsion composition; cream and/or lotion formulation; combination of provided emulsion composition and cream and/or lotion formulation; etc.) in combination with MSC. In some embodiments, the present invention provides technologies for treating conditions or disorders by topically administering to a patient a composition containing a provided emulsion composition in combination with MSC as described herein.

In some embodiments, a large agent penetrates the skin within about 1, 2, 3, 4, 5, 6, 7, 8, 9, or 10 minutes of administration. In some embodiments, a large agent penetrates the skin within about 5 to about 60 minutes of administration. In some embodiments, a large agent penetrates the skin within about 5 to about 12 minutes of administration. In some embodiments, a large agent penetrates the skin within about 5 to about 15 minutes of administration. In some embodiments, a large agent penetrates the skin within about 15 to about 30 minutes of administration. In some embodiments, a large agent penetrates the skin within about 1 hour of administration. In some embodiments, a large agent penetrates the skin within about 2 hours of administration. In some embodiments, a large agent penetrates the skin within about 3 hours of administration. In some embodiments, a large agent penetrates the skin within about 4 hours of administration. In some embodiments, a large agent penetrates the skin within about 5 hours of administration. In some embodiments, a large agent penetrates the skin within about 6 hours of administration.

In some embodiments, a large agent penetrates a layer of the skin within about 1, 2, 3, 4, 5, 6, 7, 8, 9, or 10 minutes of administration. In some embodiments, a large agent penetrates a layer of the skin within about 5 to about 60 minutes of administration. In some embodiments, a large agent penetrates a layer of the skin within about 5 to about 12 minutes of administration. In some embodiments, a large agent penetrates a layer of the skin within about 5 to about 15 minutes of administration. In some embodiments, a large agent penetrates a layer of the skin within about 15 to about 30 minutes of administration. In some embodiments, a large agent penetrates a layer of the skin within about 1 hour of administration. In some embodiments, a large agent penetrates a layer of the skin within about 2 hours of administration. In some embodiments, a large agent penetrates a layer of the skin within about 3 hours of administration. In some embodiments, a large agent penetrates a layer of the skin within about 4 hours of administration. In some embodiments, a large agent penetrates a layer of the skin within about 5 hours of administration. In some embodiments, a large agent penetrates a layer of the skin within about 6 hours of administration.

In some embodiments, a large agent penetrates the top layer of the skin within about 1, 2, 3, 4, 5, 6, 7, 8, 9, or 10 minutes of administration. In some embodiments, a large agent penetrates the top layer of the skin within about 5 to about 60 minutes of administration. In some embodiments, a large agent penetrates the top layer of the skin within about 5 to about 12 minutes of administration. In some embodiments, a large agent penetrates the top layer of the skin within about 5 to about 15 minutes of administration. In some embodiments, a large agent penetrates the top layer of the skin within about 15 to about 30 minutes of administration. In some embodiments, a large agent penetrates the top layer of the skin within about 1 hour of administration. In some embodiments, a large agent penetrates the top layer of the skin within about 2 hours of administration. In some embodiments, a large agent penetrates the top layer of the skin within about 3 hours of administration. In some embodiments, a large agent penetrates the top layer of the skin within about 4 hours of administration. In some embodiments, a large agent penetrates the top layer of the skin within about 5 hours of administration. In some embodiments, a large agent penetrates the top layer of the skin within about 6 hours of administration.

In some embodiments, a large agent penetrates the top layer of the skin, including the stratum corneum, dermal pores, and/or dermal glands within about 1, 2, 3, 4, 5, 6, 7, 8, 9, or 10 minutes of administration. In some embodiments, a large agent penetrates the top layer of the skin, including the stratum corneum, dermal pores, and/or dermal glands within about 5 to about 60 minutes of administration. In some embodiments, a large agent penetrates the top layer of the skin, including the stratum corneum, dermal pores, and/or dermal glands within about 5 to about 12 minutes of administration. In some embodiments, a large agent penetrates the top layer of the skin, including the stratum corneum, dermal pores, and/or dermal glands within about 5 to about 15 minutes of administration. In some embodiments, a large agent penetrates the top layer of the skin, including the stratum corneum, dermal pores, and/or dermal glands within about 15 to about 30 minutes of administration. In some embodiments, a large agent penetrates the top layer of the skin, including the stratum corneum, dermal pores, and/or dermal glands within about 1 hour of administration. In some embodiments, a large agent penetrates the top layer of the skin, including the stratum corneum, dermal pores, and/or dermal glands within about 2 hours of administration. In some embodiments, a large agent penetrates the top layer of the skin, including the stratum corneum, dermal pores, and/or dermal glands within about 3 hours of administration. In some embodiments, a large agent penetrates the top layer of the skin, including the stratum corneum, dermal pores, and/or dermal glands within about 4 hours of administration. In some embodiments, a large agent penetrates the top layer of the skin, including the stratum corneum, dermal pores, and/or dermal glands within about 5 hours of administration. In some embodiments, a large agent penetrates the top layer of the skin, including the stratum corneum, dermal pores, and/or dermal glands within about 6 hours of administration.

Kits

In some embodiments, the present invention provides pharmaceutical packs or kits including one or more emulsion compositions and one or more microneedle devices according to the present invention. In some embodiments, pharmaceutical packs or kits include preparations or pharmaceutical compositions containing provided compositions in one or more containers filled with optionally one or more additional ingredients of pharmaceutical compositions. In some embodiments, a pharmaceutical pack or kit includes an additional approved therapeutic agent (e.g., benzoyl peroxide for treatment of acne; aluminum compounds for treatment of hyperhidrosis; etc.) for use in combination therapies. In some embodiments, optionally associated with such container(s) can be a notice in the form prescribed by a governmental agency regulating the manufacture, use or sale of pharmaceutical products, which notice reflects approval by the agency of manufacture, use, or sale for human administration.

In some embodiments, kits are provided that include therapeutic reagents. As but one non-limiting example, provided compositions can be provided as topical formulations and administered as therapy in combination with use of a microneedling device. Pharmaceutical doses or instructions for self-administration therefor may be provided in a kit for administration to an individual suffering from or at risk for conditions or disorders, e.g., those associated with the dermal level of the skin.

In some embodiments, a kit may comprise (i) a provided composition; and (ii) at least one pharmaceutically acceptable excipient; and (iii) at least one device for microneedling the skin; and (iv) instructions for use.

The present invention provides, among other things, technologies for administering large agents, e.g., botulinum toxin or antibody agents, transdermally, by incorporating one or more large agents into one or more emulsion compositions which are then administered in combination with MSC. The present inventors have surprisingly found that transdermal permeation and bioavailability of botulinum toxin or antibody agents incorporated into nanoemulsion compositions is dramatically improved when used in combination with MSC. A benefit of the instant invention is the ability to administer such large agents intradermally while minimizing irritation or damage to the skin. Use of other agents or steps with the emulsion compositions and MSC are not necessarily precluded in all embodiments of the present invention, but also are not required.

The present invention therefore provides technologies for administering large agents through topical application of a superior emulsion composition (e.g., a macroemulsion composition and/or nanoemulsion composition) in combination with MSC. In some embodiments, a large agent is botulinum toxin. In some embodiments, a botulinum emulsion composition is applied directly to the skin and for absorption through the epidermal layers before MSC. In some embodiments, a botulinum emulsion composition is applied directly to the skin and for absorption through the epidermal layers after MSC. In some embodiments, a botulinum emulsion composition is applied directly to the skin and for absorption through the epidermal layers at substantially the same time as MSC.

In some embodiments, a botulinum emulsion composition in combination with MSC can penetrate the top layer of the skin, including the stratum corneum, dermal pores, and/or dermal glands, without the use of a penetration enhancing agent. In some embodiments, a botulinum emulsion composition in combination with MSC can penetrate the top layer of the skin, including the stratum corneum, dermal pores, and/or dermal glands, without the use of degradant, irritant, and/or abrasive agents.

In some embodiments, an antibody agent emulsion composition in combination with MSC can penetrate the top layer of the skin, including the stratum corneum, dermal pores, and/or dermal glands, without the use of a penetration enhancing agent. In some embodiments, a large agent is an antibody agent. In some embodiments, an antibody agent emulsion composition is applied directly to the skin and for absorption through the epidermal layers before MSC. In some embodiments, an antibody agent emulsion composition is applied directly to the skin and for absorption through the epidermal layers after MSC. In some embodiments, an antibody agent emulsion composition is applied directly to the skin and for absorption through the epidermal layers at substantially the same time as MSC. In some embodiments, an antibody agent emulsion composition is applied directly to the skin and for absorption systemically.

In some embodiments, an antibody agent emulsion composition in combination with MSC can penetrate the top layer of the skin, including the stratum corneum, dermal pores, and/or dermal glands, without the use of degradant, irritant and/or abrasive agents.

It will be appreciated by those of ordinary skill in the art that inventive compositions for topical administration may have a cosmetic formulation such as skin softener, nutrition lotion type emulsion, cleansing lotion, cleansing cream, skin milk, emollient lotion, massage cream, emollient cream, make-up base, facial pack or facial gel, cleaner formulation such as shampoos, rinses, body cleanser, hair-tonics, or soaps, or dermatological composition such as lotions, ointments, gels, creams, patches or sprays. In some embodiments, compositions for topical administration are not formulated for administration to mucous membranes (e.g., are inappropriate for application to mucous membranes and/or are not formulated to deliver an appropriate amount of large agent to or across mucous membranes).

Those of ordinary skill in the art will appreciate that units herein relate to Units that are biologically equivalent or bioactively equivalent to Units defined by commercial manufacturers of botulinum toxin.

In some embodiments, the therapeutic effects of botulinum toxin administered according to the present invention may persist as long as do the effects of injected solution. In some embodiments, the effects of such injected solution can persist for up to about 6 to 7 months. In some embodiments, the therapeutic effects of botulinum toxin administered according to the present invention may persist for up to 6 to 7 months. In some embodiments, use of a synthetic polymer carrier that can retain the botulinum toxin so that it is released slowly may prolong the effects for up to about five years (U.S. Pat. No. 6,312,708).

In some embodiments, the present invention provides a topical formulation of botulinum toxin that avoids potential complications including, but not limited to, systemic toxicity or botulism poisoning. In some embodiments, dosages of botulinum toxin (including types A, B, C, D, E, F, or G or botulinum that is genetically engineered or chemically modified to act longer or shorter in duration than botulinum toxin serotype A) can range from as low as about 1 unit to as high as about 20,000 units, with minimal risk of adverse side effects. The particular dosages may vary depending on the condition being treated and therapeutic regime being utilized. For example, treatment of subdermal, hyperactive muscles may require high transdermal dosages (e.g., 1000 units to 20,000 units) of botulinum toxin. In comparison, treatment of neurogenic inflammation or hyperactive sweat glands may require relatively small transdermal dosages (e.g. about 1 unit to about 1,000 units) of botulinum toxin.

Some embodiments of the present invention contemplate a pharmaceutical composition comprising a stabilized botulinum toxin for transdermal delivery into a human patient. The botulinum toxin can be selected from the group consisting of botulinum toxin types A, B, $C_1$, D, E, F and G, an isolated and/or purified (i.e. about 150 kDa) botulinum toxin, as well as a native or recombinantly made botulinum toxin. In some embodiments, a composition can comprise between about 1 unit to about 20,000 units of botulinum toxin, and the composition can comprise an amount of botulinum toxin sufficient to achieve a therapeutic effect lasting between 1 month and 5 years.

In some embodiments, the present invention provides topical formulations of botulinum toxin (e.g., of botulinum emulsion compositions) that allow the botulinum toxin to permeate through a subject's skin without permeating in significant amount through a blood vessel. For example, in some embodiments of the invention, less than about 25%, less than about 20%, less than about 15%, less than about 10%, less than about 5%, less than about 4%, less than about 3%, less than about 2%, or less than about 1% of the botulinum toxin present in the pharmaceutical composition permeates into a blood vessel upon application of an inventive topical and/or transdermal preparation.

In some embodiments, the present invention provides topical formulations of antibody agent (e.g., of antibody agent emulsion compositions) that allow the antibody agent to permeate through a subject's skin without permeating in significant amount through a blood vessel. For example, in some embodiments of the invention, less than about 25%, or even less than about 5% of the antibody agent present in the pharmaceutical composition permeates into a blood vessel upon application of an inventive topical and/or transdermal preparation.

In some embodiments, the present invention provides topical formulations of antibody agent (e.g., of antibody agent emulsion compositions) that allow the antibody agent to permeate through a subject's skin and permeate in significant amount through a blood vessel. In some embodiments, the present invention provides topical formulations of antibody agent (e.g., of antibody agent emulsion compositions) that allow the antibody agent to permeate through a subject's skin and permeate in a therapeutically effective amount through a blood vessel. For example, in some embodiments of the invention, greater than about 25%, 50%, 75%, 90%, or 95% of the antibody agent present in the pharmaceutical composition permeates into a blood vessel upon application of an inventive topical and/or transdermal preparation. In some embodiments, the present invention provides topical formulations of antibody agent (e.g., of antibody agent emulsion compositions) that allow the antibody agent to have systemic effect on a subject.

Those of ordinary skill in the art will appreciate that inventive compositions that achieve transdermal administration of botulinum toxin or antibody agents may be incorporated into a device such as, for example, a patch.

EXEMPLIFICATION

Example 1

Effect of Microneedle Skin Pre-Conditioning (MSC) Pre-Treatment on the Bioavailability of *Botulinum toxin*

A single dose topical study of the bioavailability of botulinum toxin after topical administration of a botulinum nanoemulsion was performed. The study was designed to test whether microneedle skin conditioning pre-treatment (i.e., as described herein, MSC performed prior to any administration of the botulinum treatment) significantly enhanced botulinum bioavailability.

The study included two test groups of eight rats each. Each group was treated once topically once with a fixed volume of the botulinum nanoemulsion at a fixed concentration of botulinum to the skin overlying the biceps femoris, gastrocnemius, and tibialis anterior of the right posterior limb. The administration of the topical preparation to the skin took about 10 minutes, at which time the topical preparation was fully absorbed into the skin. The effect of such treatment was measured using a scale that measures limb paralysis, which is a known effect of administration of botulinum to the limb. The scale is based on the digital abduction score (DAS score), a four-point scale developed by Aoki (2001, *Toxicon*, 39:1815; and 2002, *Toxicon*, 40:923) and can be readily assessed in the treated rats. A score of 0 is no paralysis and a score of 4 is full paralysis. It is also known that doses of botulinum that are administered at sufficient concentrations to induce paralysis may also go on to induce death in the animals. Therefore, death rates were also compared in the two treatment groups.

As described in Table 5, Group 1 had no skin preconditioning with MN. Group 2 was treated (i.e., had skin preconditioning) with five skin impressions of a microneedle array with 1400 mm needles of each area covering each of the biceps femoris, gastrocnemius, and tibialis anterior of the right posterior limb. The botulinum nanoemulsion topical treatment was fully rubbed into the skin with a gloved finger until no treatment was observed or felt on the skin.

TABLE 5

Summary of rat study groups

| Group | Skin Prep. | # of microneedle Impressions | Dose Volume (µl/rat) | Number of Animals Females |
|---|---|---|---|---|
| 1 | none | 0 | 400 | 8 |
| 2 | 1400 mm array | 5 | 400 | 8 |

Figure 2:
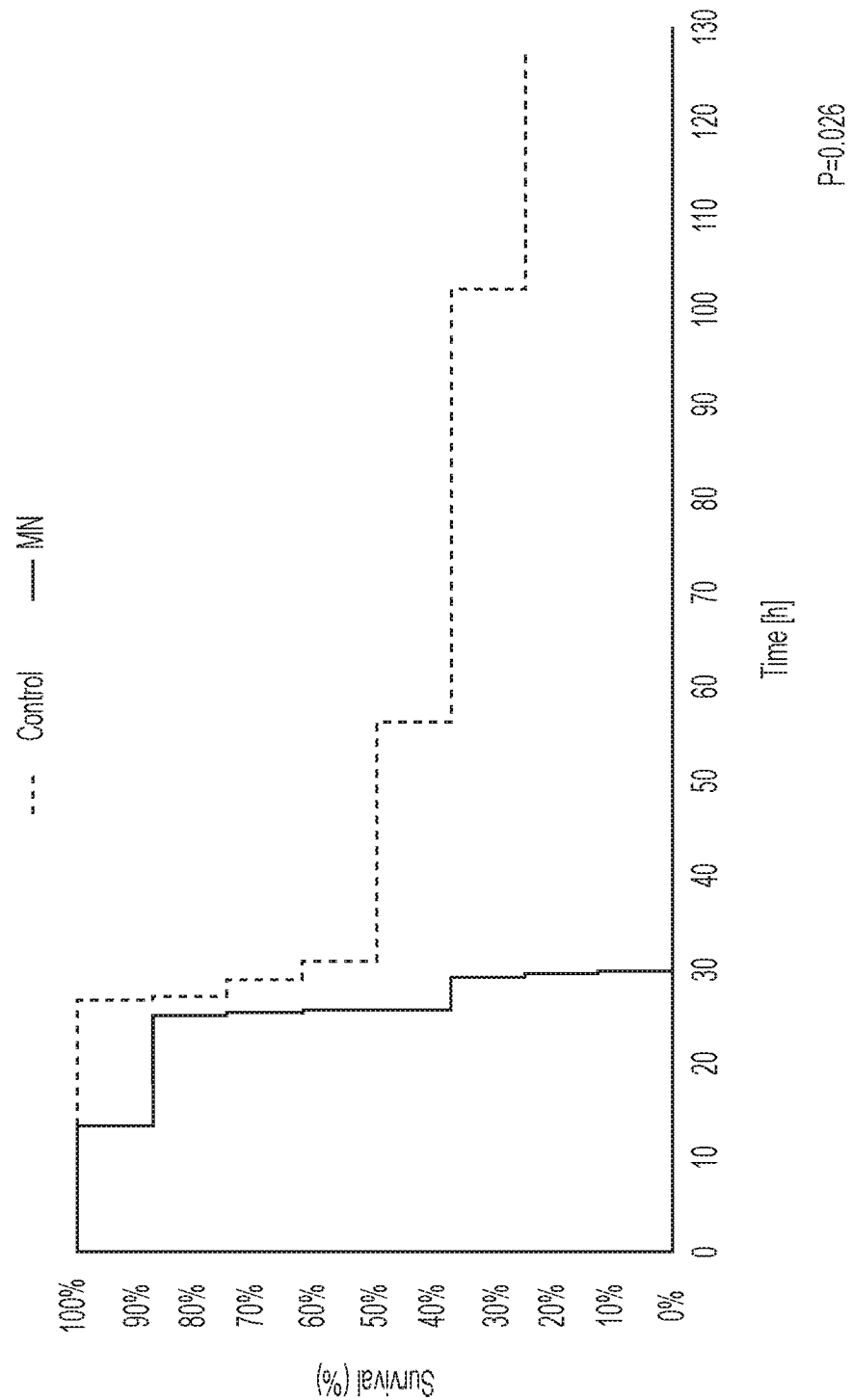
FIG. 2 depicts the survival rates of a rat study of the effect of MSC on the bioavailability of a botulinum nanoemulsion formulation.

As shown in FIG. 1, one day after treatment, the animals that had been subjected to MSC had approximately twice the DAS score of the control group which had no such pre-conditioning, establishing that MSC unexpectedly increases the bioavailability of a topical large agent nanoemulsion comprising botulinum toxin. Similarly, as shown in FIG. 2, it was found that the death rate in the animals subjected to MSC (100%) was approximately twice the death rate at 40 hours after treatment when compared to death rate in the control group which had no such pre-conditioning (50%), again establishing that MSC unexpectedly increases the bioavailability of a topical, large agent nanoemulsion comprising botulinum toxin.

In sum, the results of the study confirmed that MSC significantly enhances botulinum bioavailability.

Example 2

Effect of MSC Pre-Conditioning on the Bioavailability of Botulinum Toxin in Man: Effects on Sweat Reduction A single dose topical study of the bioavailability of botulinum toxin after topical administration of a topical botulinum nanoemulsion formulation in man is performed. The study is designed to test whether microneedle skin pre-conditioning significantly enhanced botulinum bioavailability in man by measuring sweat reduction in the skin following topical treatment with a botulinum nanoemulsion formulation.

The study includes one subject. Two spots, each on the abdomen, each approximately 2 cm squared in area, each 5 cm apart are from one another, are selected and marked with a marker. Each spot is treated once topically with a fixed volume of a botulinum nanoemulsion formulation that is at a fixed concentration of botulinum. The administration of the topical preparation to the skin takes about 5 minutes, at which time the topical preparation is fully absorbed into the skin. The first spot has no pre-conditioning with a microneedle array and is the Control Site. The second spot is pre-conditioned with three impressions of a microneedle array of 1400 micrometers in length prior to application of the botulinum formulation and is the Intervention Site.

The expected effect of such a treatment is reduced sweating at the site of the botulinum nanoemulsion treatment. The amount of sweating at the treatment sites is measured by two methods: 1) An Evaporimeter Test whereby an instrument used for measuring the rate of water evaporation from the skin is used to detect that rate of sweating (such that greater evaporation is detected with increased sweating); or 2) A Starch-Iodine Test whereby the subject has povidine applied to the treatment site; it is allowed to dry; corn starch is sprinkled over the treatment site; when the subject sweats into the white corn starch, it turns purple; if the subject does not sweat it remains white; this is called the Starch-Iodine Test. For either method of sweat detection, to induce sweating, the subject is placed under a heat lamp and then the sweat detection methods are employed.

The sweat detection methods are employed at baseline prior to a botulinum nanoemulsion treatment; at two weeks after treatment and at four weeks after treatment. The study finds that at Baseline, the average amount of sweat detected by either the Evaporimeter Test or Starch-Iodine Test is approximately equal across the Control and Intervention sites. At two weeks and four weeks after treatment, the average amount of sweat detected by either the Evaporimeter Test or Starch-Iodine Test at the Control site is more than is detected at the Intervention Site at these post-treatment weeks.

This study establishes that microneedle pre-conditioning unexpectedly increases the bioavailability of a topical, large agent nanoemulsion comprising botulinum toxin.

Example 3

Effect of MSC Pre-Conditioning on the Bioavailability of Btulinum Toxin in Man: Effects on Sweat Reduction A single dose topical study of the bioavailability of botulinum toxin after topical administration of a topical botulinum nanoemulsion formulation in man is performed. The study is designed to test whether microneedle skin pre-conditioning significantly enhanced botulinum bioavailability in man by measuring sweat reduction in the skin following topical treatment with a botulinum nanoemulsion formulation.

The study includes twelve subjects. Two spots, each on the back, each approximately 2 cm squared in area, each 5 cm apart are from one another, are selected and marked with a marker. Each spot is treated once topically with a fixed volume of a botulinum nanoemulsion formulation that is at a fixed concentration of botulinum. The administration of the topical preparation to the skin takes about 5 minutes, at which time the topical preparation is fully absorbed into the skin. The first spot has no pre-conditioning with a microneedle array and is the Control Site. The second spot is pre-conditioned with three impressions of a microneedle array of 1400 micrometers in length prior to application of the botulinum formulation and is the Intervention Site.

The expected effect of such a treatment is reduced sweating at the site of the botulinum nanoemulsion treatment. The amount of sweating at the treatment sites is measured by two methods: 1) An Evaporimeter Test whereby an instrument used for measuring the rate of water evaporation from the skin is used to detect that rate of sweating (such that greater evaporation is detected with increased sweating); or 2) A Starch-Iodine Test whereby the subject has povidine applied to the treatment site; it is allowed to dry; corn starch is sprinkled over the treatment site; when the subject sweats into the white corn starch, it turns purple; if the subject does not sweat it remains white; this is called the Starch-Iodine Test. For either method of sweat detection, to induce sweating, the subject is placed in a sauna and then the sweat detection methods are employed.

The sweat detection methods are employed at baseline prior to a botulinum nanoemulsion treatment; at two weeks after treatment and at four weeks after treatment. The study finds that at Baseline, the average amount of sweat detected by either the Evaporimeter Test or Starch-Iodine Test is approximately equal across the Control and Intervention sites. At two weeks and four weeks after treatment, the average amount of sweat detected by either the Evaporimeter Test or Starch-Iodine Test at the Control site is more than is detected at the Intervention Site at these post-treatment weeks.

This study establishes that microneedle pre-conditioning unexpectedly increases the bioavailability of a topical, large agent nanoemulsion comprising botulinum toxin.

Example 4

Effect of MSC Pre-Conditioning on the Bioavailability of Botulinum Toxin in Man: Effects on Sweat Reduction A single dose topical study of the bioavailability of botulinum toxin after topical administration of a topical botulinum nanoemulsion formulation in man is performed. The study is designed to test whether microneedle skin conditioning significantly enhanced botulinum bioavailability in man by measuring sweat reduction in the skin following topical treatment with a botulinum nanoemulsion formulation.

The study includes one subject. Two spots, each on the abdomen, each approximately 3 cm squared in area, each 5 cm apart are from one another, are selected and marked with a marker. Each spot is treated once topically with a fixed volume of a botulinum nanoemulsion formulation. The administration of the topical preparation to the skin takes about 5 minutes, at which time the topical preparation is fully absorbed into the skin. The first spot has no pre-conditioning with a microneedle array prior to application of the botulinum formulation and is the Control Site. The second spot is pre-conditioned with three impressions of a microneedle array of 1400 micrometers in length prior to application of the botulinum formulation, is the Intervention Site, and the concentration of the botulinum formulation administered to the Intervention Site is half that of the Control Site.

The expected effect of such a treatment is reduced sweating at the site of the botulinum nanoemulsion treatments. The amount of sweating at the treatment sites is measured by two methods: 1) An Evaporimeter Test whereby an instrument used for measuring the rate of water evaporation from the skin is used to detect that rate of sweating (such that greater evaporation is detected with increased sweating); or 2) A Starch-Iodine Test whereby the subject has povidine applied to the treatment site; it is allowed to dry; corn starch is sprinkled over the treatment site; when the subject sweats into the white corn starch, it turns purple; if the subject does not sweat it remains white; this is called the Starch-Iodine Test. For either method of sweat detection, to induce sweating, the subject is placed under a heat lamp and then the sweat detection methods are employed.

The sweat detection methods are employed at baseline prior to a botulinum nanoemulsion treatment; at two weeks after treatment and at four weeks after treatment. The study finds that at Baseline, the average amount of sweat detected by either the Evaporimeter Sweat Test or Starch-Iodine Test is approximately equal across the Control and Intervention sites. At two weeks and four weeks after treatment, the average amount of sweat detected by either the Evaporimeter Test or Starch-Iodine Test at the Control site is comparable to one another, despite the fact that the concentration of the botulinum formulation administered to the Intervention Site is half that of the Control Site. This study establishes that microneedle pre-conditioning unexpectedly increases the bioavailability of a topical, large agent nanoemulsion comprising botulinum toxin.

Example 5

Effect of Microneedling (MN) Skin Pre-Conditioning on the Bioavailability of Botulinum Toxin in Man: Effects on Sweat and Wrinkle Reduction A single dose topical study of the bioavailability of botulinum toxin after topical administration of a topical botulinum nanoemulsion formulation in man is performed. The study is designed to test whether microneedle skin pre-conditioning significantly enhanced botulinum bioavailability in man by measuring sweat reduction and wrinkle reduction in the skin following topical treatment with a botulinum nanoemulsion formulation.

The study includes one subject who has severe frontalis (or horizontal) wrinkles on her forehead. Two spots, each on the forehead of the subject, each approximately 2 cm squared in area, each 5 cm apart are from one another, are selected and marked with a marker. Each spot is treated once topically with a fixed volume of a botulinum nanoemulsion formulation that is at a fixed concentration of botulinum. The administration of the topical formulation to the skin takes about 5 minutes, at which time the topical formulation is fully absorbed into the skin. The first spot has no pre-conditioning with a microneedle array and is the Control Site. The second spot is pre-conditioned with three impressions of a microneedle array of 1400 micrometers in length prior to application of the botulinum formulation and is the Intervention Site.

The expected effect of such a treatment is reduced sweating at the site of the botulinum nanoemulsion treatment. The amount of sweating at the treatment sites is measured by two methods: 1) An Evaporimeter Test whereby an instrument used for measuring the rate of water evaporation from the skin is used to detect that rate of sweating (such that greater evaporation is detected with increased sweating); or 2) A Starch-Iodine Test whereby the subject has povidine applied to the treatment site; it is allowed to dry; corn starch is sprinkled over the treatment site; when the subject sweats into the white corn starch, it turns purple; if the subject does not sweat it remains white; this is called the Starch-Iodine Test. For either method of sweat detection, to induce sweating, the subject is placed in a sauna and then the methods are employed.

The expected effect of a botulinum nanoemulsion treatment is to reduce the frontalis wrinkles at the site of the botulinum nanoemulsion treatment. The severity of the wrinkles is measured using a four-point wrinkle scale (the Wrinkle Scale): 0=None, 1=Mild, 2=Moderate, 3=Severe.

The sweat detection methods are employed at baseline prior to a botulinum nanoemulsion treatment; at two weeks after treatment and at four weeks after treatment. The study finds that at Baseline, the average amount of sweat detected by either the Evaporimeter Test or Starch-Iodine Test is approximately equal across the Control and Intervention sites. At two weeks and four weeks after treatment, the average amount of sweat detected by either the Evaporimeter Test or Starch-Iodine Test at the Control site is more than is detected at the Intervention Site at these post-treatment weeks. The study finds that at Baseline, the average severity of the frontalis wrinkles as measured by the Wrinkle Scale is approximately equal across the Control and Intervention sites. At two weeks and four weeks after treatment, the average severity of the frontalis wrinkles measured by the Wrinkle Scale at the Control site is more than is detected at the Intervention Site at these post-treatment weeks.

This study establishes that microneedle pre-conditioning unexpectedly increases the bioavailability of a topical, large agent nanoemulsion comprising botulinum toxin.

Example 6

Effect of Microneedling (MN) Skin Pre-Conditioning on the Bioavailability of Botulinum Toxin in Man: Effects on Sweat Reduction in Hyperhidrosis Subjects A single dose topical study of the bioavailability of botulinum toxin after topical administration of a topical botulinum nanoemulsion formulation in man is performed. The study is designed to test whether microneedle skin pre-conditioning significantly enhanced botulinum bioavailability in man by measuring sweat reduction in the skin following topical treatment with a botulinum nanoemulsion formulation.

The study includes two treatment groups of twenty subjects each who have a condition axillary hyperhidrosis which is characterized by excessive sweating in the underarms: Group 1 is the Control group and has a botulinum nanoemulsion applied to each subject's underarms; Group 2 is the Intervention group and is pre-conditioned with three impressions of a microneedle array of 1400 micrometers in length to each part of the skin of underarm prior to application of the botulinum nanoemulsion formulation. Each subject in Groups 1 and 2 is treated once topically once with a fixed volume of a botulinum nanoemulsion formulation that is at a fixed concentration of botulinum. The administration of the topical formulation to the skin takes about 5 minutes, at which time the topical formulation is fully absorbed into the skin.

The expected effect of such a treatment is reduced sweating at the site of the botulinum nanoemulsion treatment which is the underarms. The amount of sweating at the treatment site is measured by gravimetric sweat measurement (GS Test): the underarm of the subject is dried with a paper towel; a filter paper is weighed; the filter paper is applied to the underarm for 5 minutes and then re-weighed; the excess weight after re-weighing the paper is the weight of the sweat that the subject produced in five minutes. The severity of the subject's hyperhidrosis condition is measured by the subject using the Hyperhidrosis Sweat Severity Scale (HDSS) which a four-point scale rated by the subject: 0=None, 1=Mild, 2=Moderate, 3=Severe.

The GS Test and HDSS are employed at baseline prior to a botulinum nanoemulsion treatment; at two weeks after treatment and at four weeks after treatment. The study finds that at Baseline, the average amount of sweat detected by the GS Test or disease severity measured by the HDSS is approximately equal across Groups 1-2. At two weeks and four weeks after treatment, the average amount of sweat detected or disease severity in Group 1 is more than is detected Group 2 at these post-treatment weeks.

This study establishes that microneedle pre-conditioning unexpectedly increases the bioavailability of a topical, large agent nanoemulsion comprising botulinum toxin.

Example 7

Effect of Microneedling (MN) Skin Pre-Conditioning on the Bioavailability of Botulinum Toxin in Man: Effects on Crow's Feet Wrinkle Reduction A single dose topical study of the bioavailability of botulinum toxin after topical administration of a topical botulinum nanoemulsion formulation in man was performed. The study was designed to test whether microneedle skin pre-conditioning significantly enhanced botulinum bioavailability in man by measuring wrinkle reduction in the skin following topical treatment with a botulinum nanoemulsion formulation.

The study included one subject who had severe Crow's Feet wrinkles to the side of her eyes. A botulinum nanoemulsion was applied to the subject's Crow's Feet wrinkles. The dose of botulinum applied to the skin was approximately 15% of the amount of the effective dose when the botulinum nanoemulsion was applied with no microneedle skin pre-conditioning. An effective dose was defined as a dose that would cause at least a two-point improvement in the appearance of the wrinkles when the subject was contracting the muscles that cause the Crow's Feet wrinkles as measured by a five-point wrinkle evaluation scale. The subject was pre-conditioned with two impressions of a microneedle array of 1400 micrometers in length to each part of the skin where the Crow's Feet wrinkles are located prior to application of the botulinum nanoemulsion formulation on one side of the face and was pre-conditioned with two impressions of a microneedle array of 800 micrometers in length to each part of the skin where the Crow's Feet wrinkles are located prior to application of the botulinum nanoemulsion formulation on the other side of the face. The administration of the topical formulation to the skin took about 5 minutes, at which time the topical formulation was fully absorbed into the skin.

The expected effect of a botulinum nanoemulsion treatment is reduced Crow's Feet wrinkles at the site of the botulinum nanoemulsion treatment. The severity of the wrinkles was measured using a five-point wrinkle scale (the Wrinkle Scale): 0=None, 1=Minimal, 2=Mild, 3=Moderate, 4=Severe.

The Wrinkle Scale was employed at baseline prior to a botulinum nanoemulsion treatment; at two weeks after treatment and at four weeks after treatment. The study found that at Baseline, the subject had severe wrinkles as assessed by the Wrinkle Scale, with a score of 4 of the 5-point Wrinkle Scale. At two weeks after treatment, the average severity of the wrinkles were diminished by one point on the Wrinkle Scale to a score of 3 (Moderate) on each side of the face. At four weeks after treatment, the average severity of the wrinkles were diminished by two points on the Wrinkle Scale to a score of 2 (Mild) of each side of the face.

This study established that microneedle pre-conditioning unexpectedly increased the bioavailability of a topical, large agent nanoemulsion comprising botulinum toxin.

Example 8

Effect of Microneedling (MN) Skin Pre-Conditioning on the Bioavailability of Botulinum Toxin in Man: Effects on Crow's Feet Wrinkle Reduction A single dose topical study of the bioavailability of botulinum toxin after topical administration of a topical botulinum nanoemulsion formulation in man is performed. The study is designed to test whether microneedle skin pre-conditioning significantly enhanced botulinum bioavailability in man by measuring wrinkle reduction in the skin following topical treatment with a botulinum nanoemulsion formulation.

The study includes two treatment groups of twenty subjects each who have severe Crow's Feet wrinkles to the side of their eyes: Group 1 is the Control group and has a botulinum nanoemulsion applied to each subject's Crow's Feet wrinkles; Group 2 is the Intervention group is pre-conditioned with three impressions of a microneedle array of 1400 micrometers in length to each part of the skin where the Crow's Feet wrinkles are located prior to application of the botulinum nanoemulsion formulation. Each subject in Groups 1 and 2 is treated once topically with a fixed volume of a botulinum nanoemulsion formulation that is at a fixed concentration of botulinum. The administration of the topical formulation to the skin takes about 5 minutes, at which time the topical formulation is fully absorbed into the skin.

The expected effect of a botulinum nanoemulsion treatment is reduced Crow's Feet wrinkles at the site of the botulinum nanoemulsion treatment. The severity of the wrinkles is measured using a four-point wrinkle scale (the Wrinkle Scale): 0=None, 1=Mild, 2=Moderate, 3=Severe.

The Wrinkle Scale is employed at baseline prior to a botulinum nanoemulsion treatment; at two weeks after treatment and at four weeks after treatment. The study finds that at Baseline, the average severity of wrinkles detected by the Wrinkle Scale is approximately equal across Groups 1-2. At two weeks and four weeks after treatment, the average severity of the wrinkles in Group 1 is more than is detected in Group 2 at these post-treatment weeks.

This study establishes that microneedle pre-conditioning unexpectedly increases the bioavailability of a topical, large agent nanoemulsion comprising botulinum toxin.

Example 9

Effect of Microneedling (MN) Skin Pre-Conditioning on the Bioavailability of Botulinum Toxin in Man: Effects of Dosing Variation on Crow's Feet Wrinkle Reduction A single dose topical study of the bioavailability of botulinum toxin after topical administration of a topical botulinum nanoemulsion formulation in man is performed. The study is designed to test whether microneedle skin pre-conditioning significantly enhanced botulinum bioavailability in man by measuring wrinkle reduction in the skin following topical treatment with a botulinum nanoemulsion formulation.

The study includes two treatment groups of twenty subjects each who have severe Crow's Feet wrinkles: Group 1 is the Control group and has a botulinum nanoemulsion to each subject's Crow's Feet wrinkles; Group 2 is the Intervention group is pre-conditioned with three impressions of a microneedle array of 1400 micrometers in length to each part of the skin where Crow's Feet wrinkles are located prior to application of the botulinum nanoemulsion formulation. Each subject is treated once topically with a fixed volume of a botulinum nanoemulsion formulation that is at a fixed concentration of botulinum except that Group 1's treatment is twice the concentration of botulinum as Group 2's treatment. The administration of the topical formulation to the skin takes about 5 minutes, at which time the topical formulation is fully absorbed into the skin.

The expected effect of a botulinum nanoemulsion treatment is reduced Crow's Feet wrinkles at the site of the botulinum nanoemulsion treatment. The severity of the wrinkles is measured using a four-point wrinkle scale (the Wrinkle Scale): 0=None, 1=Mild, 2=Moderate, 3=Severe.

The Wrinkle Scale is employed at baseline prior to a botulinum nanoemulsion treatment; at two weeks after treatment and at four weeks after treatment. The study finds that at Baseline, the average severity of wrinkles detected by the Wrinkle Scale is approximately equal across Groups 1 and 2. At two weeks and four weeks after treatment, the average severity of the wrinkles in Group 1 and 2 are reduced when compared to baseline by approximately the same amount despite Group 1 being treated with twice the concentration of Group 2.

This study establishes that microneedle pre-conditioning unexpectedly increases the bioavailability of a topical, large agent nanoemulsion comprising botulinum toxin such that lower doses of botulinum may be employed to get equivalent therapeutic effects when compared to patients who did not receive microneedle skin pre-conditioning.

Example 10

Effect of Microneedling (MN) Skin Pre-Conditioning on the Bioavailability of Botulinum Toxin in Man: Effects of Dosing Variation on Crow's Feet Wrinkle Reduction A single dose topical study of the bioavailability of botulinum toxin after topical administration of a topical botulinum macroemulsion formulation in man is performed. The study is designed to test whether microneedle skin pre-conditioning significantly enhanced botulinum bioavailability in man by measuring wrinkle reduction in the skin following topical treatment with a botulinum macroemulsion formulation.

The study includes two treatment groups of twenty subjects each who have severe Crow's Feet wrinkles: Group 1 is the Control group and has a botulinum macroemulsion to each subject's Crow's Feet wrinkles; Group 2 is the Intervention group is pre-conditioned with three impressions of a microneedle array of 1400 micrometers in length to each part of the skin where Crow's Feet wrinkles are located prior to application of the botulinum macroemulsion formulation. Each subject is treated once topically with a fixed volume of a botulinum nanoemulsion formulation that is at a fixed concentration of botulinum. The administration of the topical formulation to the skin takes about 5 minutes, at which time the topical formulation is fully absorbed into the skin.

The expected effect of a botulinum nanoemulsion treatment is reduced Crow's Feet wrinkles at the site of the botulinum nanoemulsion treatment. The severity of the wrinkles is measured using a four-point wrinkle scale (the Wrinkle Scale): 0=None, 1=Mild, 2=Moderate, 3=Severe.

The Wrinkle Scale is employed at baseline prior to a botulinum nanoemulsion treatment; at two weeks after treatment and at four weeks after treatment. The study finds that at Baseline, the average severity of wrinkles detected by the Wrinkle Scale is approximately equal across Groups 1 and 2. At two weeks and four weeks after treatment, the average severity of the wrinkles in Group 1 is greater than the average severity of wrinkles in Group 2.

This study establishes that microneedle pre-conditioning unexpectedly increases the bioavailability of a topical, large agent macroemulsion comprising botulinum toxin when compared to patients who did not receive microneedle skin pre-conditioning.

REFERENCES

Alkilani, A. Z., et al., "transdermal drug delivery: innovative pharmaceutical developments based on disruption of the barrier properties of the stratum corneum." Pharmaceutics. 7:438-470 (2015).

Gomaa, Y., et al, "Effect of microneedle treatment on the skin permeation of a nanoencapsulated dye." J Pharm Pharmacol. 2012 November; 64(11): 1592-1602.

Guo, L., et al., "Enhanced transcutaneous immunization via dissolving microneedle array loaded with liposome encapsulated antigen and adjuvant." International Journal of Pharmaceutics. 447:22-30 (2013)

Hiraishi, Y., et al., "Development of a novel therapeutic approach using a retinoic acid-loaded microneedle patch for seborrheic keratosis treatment and safety study in humans." Journal of Controlled Release. 171:93-103 (2013).

Ling, M. & Chen, M., "Dissolving polymer microneedle patches for rapid and efficient transdermal delivery of insulin to diabetic rats." Acta Biomaterialia, 9, 8952-8961 (2013).

Prausnitz, M. R. & Langer, R. "Transdermal drug delivery," Nat Biotechnol. 26(11): 1261-1268 (2008).

Qin, G., et al., "Simultaneous basal-bolus delivery of fast-acting insulin and its significance in diabetes management." Nanomedicine: NBM, 8:221-227 (2012).

Tang, H., et al., "Theoretical description of transdermal transport of hydrophilic permeants: Application to low-frequency sonophoresis." Journal of Pharmaceutical Sciences. 90(5):545-568 (2001).

Verbaan, F. J., et al., "Assembled microneedle arrays enhance the transport of compounds varying over a large range of molecular weight across human dermatomed skin." Journal of Controlled Release. 117: 238-245 (2007).

Wu, X., et al., "Effects of pretreatment of needle puncture and sandpaper abrasion on the in vitro skin permeation of fluorescein isothiocyanate (FITC)-dextran." International Journal of Pharmaceutics. 316:102-108 (2006).

Zhang, S., et al., "Enhanced bioavailability of L-carnitine after painless intradermal delivery vs. oral administration in rats." Pharm Res. 28:117-123 (2011).

Zhang, S., et al., "Enhanced delivery of hydrophilic peptides in vitro by transdermal microneedle pretreatment." Acta Pharmaceutica Sinica B. 4(1):100-104 (2014).

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

---

---

I claim:

1. A method of transdermally delivering a large agent to a subject, the method comprising:
    applying an emulsion composition comprising the large agent having a molecular weight of 100,000 Da or greater to a site of the subject in combination with microneedle skin conditioning (MSC) of the site, wherein the emulsion composition is formulated so that the large agent can penetrate the site without use of a penetration enhancing agent.

2. The method of claim 1, wherein the composition comprising a large agent comprises a nanoemulsion comprising the large agent.

3. The method of claim 1, wherein the composition comprising a large agent comprises a macroemulsion comprising the large agent.

4. The method of claim 1, wherein the MSC of the site is performed before applying the composition comprising a large agent to the site.

5. The method of claim 1, wherein the MSC of the site is performed after applying the composition comprising a large agent to the site.

6. The method of claim 1, wherein the MSC of the site and applying the composition comprising a large agent to the site occur at substantially the same time.

7. The method of claim 1, wherein the large agent is a botulinum toxin.

8. The method of claim 7, further comprising delivering botulinum toxin with a biologically active agent.

9. The method of claim 8, wherein the biologically active agent is selected from the group consisting of steroids, retinoids, anesthetics, fillers, silicone, and collagen.

10. The method of claim 9, wherein the biologically active agent is selected from the group consisting of hydrocortisone, retin A, and lidocaine.

11. The method of claim 1, wherein the large agent is an antibody agent.

12. The method of claim 11, wherein the antibody agent is selected from the group consisting of an anti-TNFα antibody, an anti-CD2 antibody, an anti-CD4 antibody, an anti-IL-12 antibody, an anti-IL-17 antibody, an anti-IL-22 antibody, and an anti-IL-23 antibody.

13. The method of claim 11, wherein the antibody agent is an antibody having epitope binding elements found in one or more of infliximab, adalimumab, golimumab, etanercept, etanercept-szzs, certolizumab pegol, siplizumab, zanolimumab, briakinumab, secukinumab, brodalumab, fezakinumab, ustekinumab and guselkumab.

14. The method of claim 11, further comprising delivering the antibody agent with a biologically active agent.

15. The method of claim 1, wherein the MSC of the site is accomplished with a device comprising a plurality of needles.

16. The method of claim 15, wherein the device is a patch, a roller, stamp, or pen.

17. The method of claim 1, wherein the site is a skin surface overlying a muscle or muscle group of the subject.

18. The method of claim 1, wherein the site is a skin surface that contains sweat glands.

19. The method of claim 1, wherein the site is a skin surface that contains sebaceous glands.

20. The method of claim 1, wherein the site is a skin surface that contains hair follicles.

21. The method of claim 15, wherein the needles have a length sufficient to project through the stratum corneum of the skin.

22. The method of claim 15, wherein the needles have a length insufficient to reach nerves in the dermis of the skin.

23. The method of claim 15, wherein the needles have a length between about 10 and about 4000 µm.

24. The method of claim 15, wherein the needles have a length equal to or greater than about 100 µm.

25. The method of claim 15, wherein the needles have a length equal to or greater than about 25 µm.

26. The method claim 15, wherein the needles have a length equal to or greater than about 300 µm, about 500 µm, about 800 µm, about 1000 µm, about 1500 µm, about 2000 µm, or about 4000 µm.

27. The method of claim 15, wherein the needles are composed of a biocompatible material.

28. The method of claim 15, wherein the needles are composed of a metal.

29. The method of claim 1, wherein the MSC comprises administration of 1, 2, 3, 4, 5, 6, 7, 8, 9, 10, 11, 12, 13, 14, 15, 16, 17, 18, 19, or 20 MN or MN array impressions.

30. The method of claim 29, wherein the MN array is rotated between one or more impressions.

31. The method of claim 29, wherein the MN array is not rotated between one or more impressions.

32. The method of claim 29, wherein the impressions are made on the same site.

33. The method of claim 29, wherein the impressions are made on overlapping sites.

34. The method of claim 29, wherein the impressions are made on different sites.

35. The method of claim 29, wherein the MN array is in the form of a stamp or roller.

36. The method of claim 35, wherein the impressions are made by stamping or rolling.

37. The method of claim 1, wherein the large agent penetrates the skin within about 1, 2, 3, 4, 5, 6, 7, 8, 9, or 10 minutes of administration.

38. The method of claim 1, wherein the large agent penetrates the skin within about 5 to about 60 minutes, about 5 to about 12 minutes, about 5 to about 15 minutes, or about 15 to about 30 minutes of administration.

39. The method of claim 1, wherein the large agent penetrates the skin within about 1, 2, 3, 4, 5, or 6 hours of administration.

40. The method of claim 15, wherein the needles are composed of a dissolving polymer.

41. The method of claim 1, wherein the administering comprises administering the composition comprising a large agent at a lower dose as compared to a reference topical treatment regimen where microneedles are not employed.

42. The method of claim 1, comprising administering more than one doses of the composition comprising a large agent over time.

43. The method of claim 42, wherein the administering comprises administering fewer doses of the composition comprising a large agent over a fixed treatment period as compared to a reference treatment regimen where microneedles are not employed to generate comparable treatment effects.

44. The method of claim 42, wherein each dose of the composition comprising a large agent is separated by a specified period of time.

45. The method of claim 44, wherein the specified period of time is longer as compared to the specified period of time for administering a reference treatment regimen where microneedles are not employed.

46. The method of claim 41, wherein the reference treatment regimen comprises administering the composition comprising a large agent without MSC.

47. A method of treating a dermatological disorder comprising the method of claim 1.

48. The method of claim 47, wherein the dermatological disorder is selected from the group consisting of acne, unwanted sweating, body odor, hyperhidrosis, bromhidrosis, chromhidrosis, rosacea, hair loss, psoriasis, actinic keratosis, eczematous dermatitis, excess sebum-producing disorders, burns, lupus erythematosus, hyperpigmentation disorders, hypopigmentation disorders, skin cancer, dermal infection, facial wrinkles, unsightly facial expressions, neck lines, hyperfunctional facial lines, hyperkinetic facial lines, platysma bands, and combinations thereof.

49. A method of treating or preventing a disorder selected from the group consisting of unwanted sweating, body odor, hyperhidrosis, bromhidrosis, chromhidrosis, hair loss, Raynaud's phenomenon, rheumatoid arthritis, psoriatic arthritis, osteoarthritis, lupus erythematosus, systemic lupus, discoid lupus, drug-induced lupus, neonatal lupus, Crohn's disease, inflammatory bowel disease, ulcerative colitis, pulmonary disorders, asthma, chronic obstructive pulmonary disorder, amyloidosis, systemic amyloidosis, cutaneous amyloidosis, cancer, skin cancer, blood cancer, breast cancer, colon cancer, lung cancer, prostate hyperplasia, dyslipidemia, hypercholesterolemia, infection, *C. difficile* infection, *Staphylococcus* infection, dystonia, headache, pain, arthritis associated pain, rheumatoid arthritis associated pain, psoriatic arthritis associated pain, osteoarthritis associated pain, certain ophthalmologic conditions, certain urologic conditions, neuromuscular disorders, conditions involving muscular spasm and/or contracture, strabismus, hemifacial spasm, tremor, spasticity resulting from multiple sclerosis, retroorbital muscle, neurologic conditions, Alzheimer's Disease, Parkinson's Disease, and stroke, comprising the method of claim 1.

50. The method of claim 1, wherein the composition comprising a large agent is formulated as a lotion, cream, powder, ointment, liniment, gel, or drops.

\* \* \* \* \*